United States Patent
Lesur et al.

(10) Patent No.: US 7,297,817 B2
(45) Date of Patent: Nov. 20, 2007

(54) THIO-SUBSTITUTED ARYLMETHANESULFINYL DERIVATIVES

(75) Inventors: Brigitte Lesur, Champs sur Marne (FR); Philippe Louvet, Montgeron (FR); Rabindranath Tripathy, Churchville, PA (US)

(73) Assignees: Cephalon France, Maisons-Alfort Cedex (FR); Cephalon, Inc., Frazer, PA (US)

( * ) Notice: Subject to any disclaimer, the term of this patent is extended or adjusted under 35 U.S.C. 154(b) by 2 days.

(21) Appl. No.: 11/104,074

(22) Filed: Apr. 12, 2005

(65) Prior Publication Data

US 2005/0256133 A1 Nov. 17, 2005

Related U.S. Application Data

(60) Provisional application No. 60/568,991, filed on May 7, 2004.

(30) Foreign Application Priority Data

Apr. 13, 2004 (EP) .................................. 04290983

(51) Int. Cl.
C07C 233/05 (2006.01)
A61K 31/18 (2006.01)

(52) U.S. Cl. ....................... 564/162; 564/154; 562/430; 560/11; 560/15; 558/392; 514/521; 514/532; 514/546; 514/555; 514/616; 514/618

(58) Field of Classification Search ................ 514/616, 514/618, 521, 555, 532, 546; 558/392; 560/11, 560/15; 562/426, 429, 430; 564/154, 162, 564/616, 618

See application file for complete search history.

(56) References Cited

U.S. PATENT DOCUMENTS

| | | | |
|---|---|---|---|
| 3,976,694 A | 8/1976 | Kaiser et al. | 260/570.5 C |
| 4,006,183 A | 2/1977 | Jackson | 260/558 S |
| 4,066,686 A | 1/1978 | Lafon | 260/500.5 |
| 4,177,290 A | 12/1979 | Lafon | 424/324 |
| 4,744,812 A * | 5/1988 | Parg et al. | 504/315 |
| 4,927,855 A | 5/1990 | Lafon | 514/618 |
| 4,935,240 A | 6/1990 | Nakai et al. | 424/400 |
| 4,980,372 A | 12/1990 | Nakai et al. | 514/510 |
| 5,180,745 A | 1/1993 | Lafon | 514/618 |
| 5,391,576 A | 2/1995 | Lafon | 514/618 |
| 5,401,776 A | 3/1995 | Laurent | 514/618 |
| 5,563,169 A | 10/1996 | Yoshida et al. | 514/454 |
| 5,612,379 A | 3/1997 | Laurent | 514/618 |
| 5,719,168 A | 2/1998 | Laurent | 514/357 |
| 6,346,548 B1 | 2/2002 | Miller et al. | 514/618 |
| 6,455,588 B1 | 9/2002 | Scammell et al. | 514/618 |
| 6,472,414 B1 | 10/2002 | Biller et al. | 514/395 |
| 6,488,164 B2 | 12/2002 | Miller et al. | 214/618 |
| 6,492,396 B2 | 12/2002 | Bacon et al. | 514/332 |
| 6,670,358 B2 | 12/2003 | Bacon et al. | 514/231.2 |
| 6,919,367 B2 | 7/2005 | Bacon et al. | 514/425 |
| 6,924,314 B2 * | 8/2005 | Sharma et al. | 514/675 |
| 7,119,214 B2 | 10/2006 | Lesur et al. | 549/460 |
| 2002/0045629 A1 | 4/2002 | Bacon et al. | 514/256 |
| 2002/0143020 A1 | 10/2002 | Adams et al. | 514/254.1 |
| 2005/0192313 A1 | 9/2005 | Bacon et al. | 514/297 |
| 2005/0228040 A1 | 10/2005 | Bacon et al. | 514/456 |
| 2005/0234040 A1 | 10/2005 | Bacon et al. | 514/212.04 |
| 2005/0245747 A1 | 11/2005 | Bacon et al. | 548/260 |
| 2006/0241119 A1 | 10/2006 | Lesur et al. | 514/252.13 |

FOREIGN PATENT DOCUMENTS

| | | |
|---|---|---|
| DE | 150366 | 4/2004 |
| EP | 04290983.8 | 4/2004 |
| FR | 2 385 693 | 10/1978 |
| GB | 1178279 | 1/1970 |

(Continued)

OTHER PUBLICATIONS

Lehninger, A.L., "The amino acid building blocks of proteins," *Biochemistry*, 2nd ed, Worth Publishers, NY, 1975, 71-77.

Annis, I., et al., "Novel solid-phase reagents for facile formation of intramolecular disulfide bonds in peptides under mild conditions," *Pept. Proc. Am. Pept. Symp. 15th*, meeting dated 1997, 1999, 343-344.

Balzarini, J., et al., "Pridine oxide derivatives: structure-activity relationship for inhibition of human immunodeficiency virus and cytomegalovirus replication in cell culture," *Helvetica Chimica Acta*, 2002, 85, 2961-2974.

(Continued)

*Primary Examiner*—Shailendra Kumar
(74) *Attorney, Agent, or Firm*—Woodcock Washburn LLP

(57) ABSTRACT

The present invention is related to chemical compositions, processes for the preparation thereof and uses of the composition. Particularly, the present invention relates to compositions of compounds of Formula (A):

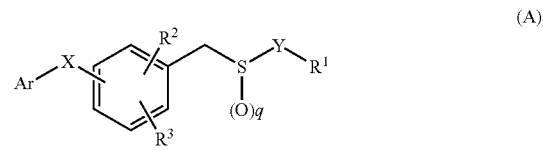

(A)

wherein Ar, X, Y, $R^1$, $R^2$, $R^3$, and q are as defined herein; and their use in the treatment of diseases, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder ("ADHD"), enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

46 Claims, No Drawings

FOREIGN PATENT DOCUMENTS

| | | |
|---|---|---|
| GB | 1 570 982 | 7/1980 |
| GB | 1 600 840 | 10/1981 |
| WO | WO 95/01171 A1 | 1/1995 |
| WO | WO 99/25329 A1 | 5/1999 |
| WO | WO 02/10125 A1 | 2/2002 |

OTHER PUBLICATIONS

Beattie, D.E., et al., "Anti-ulcer and gastric antisecretory activity of a series of thioethers and related sulphoxides," *Eur. J. Med. Chem.—Chim. Ther.*, 1983, 18(3), 277-285.

Chan, T.-L., et al., "Stereo- and oligo-controlled synthesis of oligo[*p*-phenylene-(E)-vinylene]-*p*-benzoic acid derivatives: basic building blocks for oligo[*p*-phenylene-(E)-vinylene]s," *J. Chem. Soc., Chem. Commun.*, 1994, 1919-1920.

2-(tosylamino)benzyltrimethylammonium halides as precursors of 2-substituted indoles, *Heterocycles*, 1996, 43(11), 2397-2407.

Edgar, D.M., "CCD-3693: an orally bioavailable analog of the endogenous neuroactive steroid, pregnanolone, demonstrates potent sedative hypnotic actions in the rat," *J. of Pharmacol. & Exp. Ther.*, 1997, 282(1), 420-429.

Edgar, D.M., et al., "Modafinil induces wakefulness without intensifying motor activity or subsequent rebound hypersomnolence in the rat," *J. of Pharm. & Experi. Therap.*, 1997, 283(2), 757-769.

El-Sakka, I.A., et al., "Reactions with thiaxanthen-9-ol: new thiaxanthene derivatives with molluscicidal and nematocidal activity," *Arch. Pharm. (Weinheim)*, 1994, 327, 133-135.

Han, Y., et al., "Novel S-Xanthenyl protecting groups for cysteine and their applications for the $N^a$-9-fluorenylmethyloxcarbonyl (Fmoc) strategy of peptide synthesis," *Org. Chem.*, 1997, 62, 3841-3848.

Hermant, J.-F., et al., "Awakening properties of modafinil: effect on nocturnal activity in monkeys (*Macaca mulatta*) after acute and repeated administration," *Psychopharmacology*, 1991, 103, 28-32.

Imeri, L., et al., "Blockade of 5-hydroxytryptamine (serotonin)-receptors alters interleukin-1-induced changes in rat sleep," *Neurosci.*, 1999, 92(2), 745-749.

Ishibashi, H., et al., "Synthesis of *ortho*-substituted arylacetic esters and related compounds by means of sommelet-hauser rearrangement of sulfur ylides," *Chem. Pharm. Bull.*, 1991, 39(11), 2878-2882.

Hirai, K., et al., "Amino acid amides of 2-[(2-aminobenzyl)sulfinyl}benzimidazole as acid-stable prodrugs of potential inhibitors of $H^+/K^+$ ATPase," *Eur. J. Med. Chem.*, 1991, 26, 143-158.

Lin, J.S., et al., "Role of catecholamines in the modafinil and amphetamine induced wakefulness, a comparative pharmacological study in the cat," *Brain Res.*, 1992, 591, 319-326.

Nezu, Y., et al., "Dimethoxypyrimidines as novel herbicides. Part 2. Synthesis and herbicidal activity of *O*-pyrimidinylsalicylates and analogues," *Pestic. Sci.*, 1996, 47, 115-124.

Opp, M.R., et al., "Anti-interleukin-1β reduces sleep and sleep rebound after sleep deprivation in rats," *Am. J. of Physiol.*, 1994, R688-R695.

Opp, M.R., et al., "Rat strain differences suggest a role for corticotrophin-releasing hormone in modulating sleep," *Physiol. & Behav.*, 1998, 63(1), 67-74.

Panckeri, K.A., et al., "Modafinil decreases hypersomnolence in the English bulldog, a natural animal model of sleep-disordered breathing," *Sleep*, 1996, 19(8), 626-631.

Sato, M., et al., "Preparation of anilide derivatives as acyl coenzyme A-cholestrol o-acyltransferase (ACAT) inhibitors and antiarteriosclerotics," *Chem. Abstracts* Service, Accession No. 1992:612159, 1992, 1 page.

Seidel, W.F., et al., "*Alpha*-2 adrenergic modulation of sleep: time-of-day dependent pharmacodynamic profiles of dexmedetomidine and clonidine in the rat," *J. of Pharmacol. Exp. Ther.*, 1995, 275(1), 263-273.

Shelton, J., et al., "Comparative effects of modafinil and amphetamine on daytime sleepiness and cataplexy of narcoleptic dogs," *Sleep*, 1995, 18(10), 817-826.

Takeuchi, H., et al., "Formation of sommelet-hauser-type products. 2-aminoarylmethyl sulphides, and nitrumium ion products, 2-and 4-aminoaryl sulphides, via an N-arylazasulphonium salt," *J. of Chem. Res.m Miniprint*, 1991, 12, 3156-3188.

Terauchi, H., et al., "Nicotinamide derivatives as a new class of gastric $H^+/K^+$-ATPase inhibitors. 1. Synthesis and structure-activity relationships of *N*-substituted 2-(benzhydryl- and benzylsufinyl)nicotinamides," *J. of Med. Chem.*, 1997, 40, 313-321.

Touret, M., et al., "Awakening properties of modafinil without paradoxical sleep rebound: comparative study with amphetamine in the rat," *Neurosc. Letts.*, 1995, 189, 43-46.

Van Gelder, R.N., et al., "Real-time automated sleep scoring: validation of a microcomputer-based system for mice," *Sleep*, 1991, 14(1), 48-55.

Welsh, D.K., et al., "A circadian rhythm of hippocampal theta activity in the mouse," *Physiol. & Behav.*, 1985, 35, 533-538.

Yamakawa, T., et al., "Synthesis and structure-activity relationships of *N*-substituted 2-[(2-imidazolylsulfinyl)methyl]anilines as a new class of gastric $H^+/K^+$-ATPase inhibitors," *Chem. Pharm. Bull.*, 1991, 39(7), 1746-1752.

Dostert, P. et al., "Composés tricycliques portent une chaîne alkylaminoalkylthio Synthése et activité pharmacologique," *J. Med. Chem.*, 1974, 9(3), 259-262.

Saenz, R.V. et al., "New Compounds: Amides Derived from [(10,11-Dihydro-5*1H*-dibenzo[*a,d*]cyclohepten-5-yl)thio]acetic Acid," *J. Pharm. Sci.*, 1972, 61(6), 978-980.

Portevin, B. et al., "New Prolyl Endopeptidase Inhibitors: In Vitro and in Vivo Activities of Azabicyclo[2.2.2]octane, Azabicyclo[2.2.1]heptane, and Perhydroindole Derivatives," *J. Med. Chem.*, 1996, 39, 2379-2391.

\* cited by examiner

THIO-SUBSTITUTED ARYLMETHANESULFINYL DERIVATIVES

CROSS-REFERENCE TO RELATED APPLICATIONS

This application claims priority of pending U.S. Provisional Application Ser. No. 60/568,991, filed May 7, 2004 and European Patent Application Number 04290983.8, filed Apr. 13, 2004. The disclosures of these prior applications is incorporated herein by reference in their entireties for all purposes.

FIELD OF THE INVENTION

The present invention is related to chemical compositions, processes for the preparation thereof and uses of the composition. Particularly, the present invention relates to compositions of compounds of Formula (A):

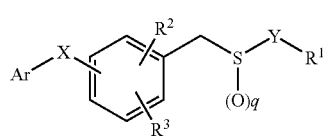

(A)

and their use in the treatment of diseases, including treatment of sleepiness, promotion and/or improvement of wakefulness, preferably improvement of wakefulness in patients with excessive sleepiness associated with narcolepsy, sleep apnea, preferably obstructive sleep apnea/hypopnea, and shift work disorder; treatment of Parkinson's disease; Alzheimer's disease; cerebral ischemia; stroke; eating disorders; attention deficit disorder ("ADD"), attention deficit hyperactivity disorder ("ADHD"); depression; schizophrenia; fatigue, preferably fatigue associated with cancer or neurological diseases, such as multiple sclerosis and chronic fatigue syndrome; stimulation of appetite and weight gain and improvement of cognitive dysfunction.

BACKGROUND OF THE INVENTION

The compounds disclosed herein are related to the biological and chemical analogs of modafinil. Modafinil, $C_{15}H_{15}NO_2S$, also known as 2-(benzhydrylsulfinyl) acetamide, or 2-[(diphenylmethyl) sulfinyl] acetamide, a synthetic acetamide derivative with wake-promoting activity, has been described in French Patent No. 78 05 510 and in U.S. Pat. No. 4,177,290 ("the '290 patent"). It has been approved by the United States Food and Drug Administration for use in the treatment of excessive daytime sleepiness associated with narcolepsy. Methods for preparing modafinil and several derivatives are described in the '290 patent. The levorotatory isomer of modafinil, along with additional modafinil derivatives are described in U.S. Pat. No. 4,927,855, and are reported to be useful for treatment of hypersomnia, depression, Alzheimer's disease and to have activity towards the symptoms of dementia and loss of memory, especially in the elderly.

Modafinil has also been described as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas and disorders of central origin (U.S. Pat. No. 5,612,379). In addition, modafinil may be used in the treatment of eating disorders, or to promote weight gain or stimulate appetite in humans or animals (U.S. Pat. No. 6,455,588), or in the treatment of attention deficit hyperactivity disorder (U.S. Pat. No. 6,346,548), or fatigue, especially fatigue associated with multiple sclerosis (U.S. Pat. No. 6,488,164). U.S. Pat. No. 4,066,686 describes various benzhydrylsulphinyl derivatives as being useful in therapy for treating disturbances of the central nervous system.

Several published patent applications describe derivative forms of modafinil and the use of modafinil derivatives in the treatment of various disorders. For example, PCT publication WO 99/25329 describes various substituted phenyl analogs of modafinil as being useful for treating drug-induced sleepiness, especially sleepiness associated with administration of morphine to cancer patients. U.S. Pat No. 5,719,168 and PCT Publication No. 95/01171 describe modafinil derivatives that are useful for modifying feeding behavior. PCT Publication No. 02/10125 describes several modafinil derivatives of modafinil, along with various polymorphic forms of modafinil.

Additional publications describing modafinil derivatives include U.S. Pat. No. 6,492,396, and PCT Publication No. WO 02/10125.

Terauchi, H, et al. described nicotinamide derivatives useful as ATP-ase inhibitors (Terauchi, H, et al, *J. Med. Chem.*, 1997, 40, 313-321). In particular, several N-alkyl substituted 2-(Benzhydrylsulfinyl) nicotinamides are described.

U.S. Pat. Nos. 4,980,372 and 4,935,240 describe benzoylaminophenoxybutanoic acid derivatives. In particular, sulfide derivatives of modafinil containing a phenyl and substituted phenyl linker between the sulfide and carbonyl, and a substituted aryl in the terminal amide position, are disclosed.

Other modafinil derivatives have been disclosed wherein the terminal phenyl groups are constrained by a linking group. For example, in U.S. Pat. No. 5,563,169, certain xanthenyl and thiaxanthenyl derivatives having a substituted aryl in the terminal amide position are reported.

Other xanthenyl and thiaxanthenyl derivatives are disclosed in Annis, I; Barany, G. *Pept. Proc. Am. Pept. Symp.* 15th (Meeting Date 1997) 343-344, 1999 (preparation of a xanthenyl derivative of Ellman's Reagent, useful as a reagent in peptide synthesis); Han, Y.; Barany, G. *J. Org. Chem.*, 1997, 62, 3841-3848 (preparation of S-xanthenyl protected cysteine derivatives, useful as a reagent in peptide synthesis); and El-Sakka, I. A., et al. *Arch. Pharm.* (Weinheim), 1994, 327, 133-135 (thiaxanthenol derivatives of thioglycolic acid).

Thus, there is a need for novel classes of compounds that possess the beneficial properties. It has been discovered that a class of compounds, referred to herein as substituted thioacetamides, are useful as agents for treating or preventing various diseases or disorders disclosed herein.

SUMMARY OF THE INVENTION

The present invention in one aspect is directed to various novel compounds of formula (A):

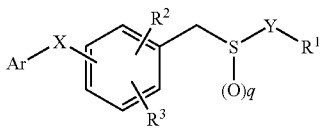

and its stereoisomeric forms, mixtures of stereoisomeric forms, or pharmaceutically acceptable salt forms thereof, wherein the constituent members are defined infra.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt or ester form thereof.

Another object of the present invention is to provide methods of treating or preventing diseases or disorders, including treatment of sleepiness, promotion and/or improvement of wakefulness, preferably improvement of wakefulness in patients with excessive sleepiness associated with narcolepsy, sleep apnea, preferably obstructive sleep apnea/hypopnea, and shift work disorder; treatment of Parkinson's disease; Alzheimer's disease; cerebral ischemia; stroke; eating disorders; attention deficit disorder ("ADD"), attention deficit hyperactivity disorder ("ADHD"); depression; schizophrenia; fatigue, preferably fatigue associated with cancer or neurological diseases, such as multiple sclerosis and chronic fatigue syndrome; stimulation of appetite and weight gain and improvement of cognitive dysfunction.

These and other objects, features and advantages of compounds of formula (A) will be disclosed in the following detailed description of the patent disclosure.

DETAILED DESCRIPTION OF THE INVENTION

In a first embodiment, the present invention provides novel compounds of formula (A):

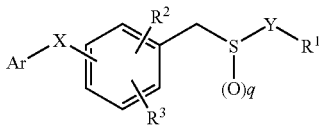

wherein:

Ar is independantly selected from $C_6$-$C_{10}$ aryl and 5 to 10-membered heteroaryl wherein:
  $C_6$-$C_{10}$ aryl and heteroaryl are optionally substituted with one to three groups selected from F, Cl, Br, I, $OR^{22}$, $OR^{25}$, $NR^{23}R^{24}$, NHOH, $NO_2$, CN, $CF_3$, $C_1$-$C_6$ alkyl $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR_{21}C(=O)R^{22}$, $NR_{21}CO_2R^{22}$, $OC(=O)NR^{23}R^{24}$, $NR^{21}C(=S)R^{22}$, and $S(O)_yR^{22}$;

X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2NR_{22}$, $NR_{22}S(O)_2$, $C(R^{22})_2C(R^{22})_2$, $CR^{21}=CR^{21}$, C≡C;

Y is $C_1$-$C_6$ alkylene; or
  $(C_1$-$C_4$ alkylene$)_m$—Z—$(C_1$-$C_4$ alkylene$)_n$;
  wherein said alkylene groups are optionally substituted with one to three $R^{20}$ groups;

Z is O, $NR^{10A}$, $S(O)_y$, $CR^{21}=CR^{21}$, C≡C, $C_6$-$C_{10}$ arylene, 5-10 membered heteroaryle, $C_3$-$C_6$ cycloalkylene, or 3-6 membered heterocycloalkylene; wherein said arylene, heteroarylene, cycloalkylene, and heterocycloalkylene groups are optionally substituted with one to three $R^{20}$ groups;

$R^1$ is selected from H, $C_6$-$C_{10}$ aryl, $NR^{12}R^{13}$, $NR_{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR_{21}S(O)_2R^{11}$, $NR^{21}C(=O)NR^{12}R^{13}$, and $NR^{21}S(O)_2NR^{12}R^{13}$; wherein said aryl groups are optionally substituted with one to three $R^{20}$ groups;

$R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

$R^{10}$ and $R^{10A}$ are each independently selected from H, $C_1$-$C_6$ alkyl, $C_6$-$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_1$-$C_6$ alkyl, preferably $C_3$-$C_7$ alkyl, and $C_6$-$C_{10}$ aryl; wherein said alkyl and aryl groups are optionally substituted with one to three $R^{20}$ groups;

$R^{12}$ and $R^{13}$ at each occurrence are each independently selected from H, $C_1$-$C_6$ alkyl, and $C_6$-$C_{10}$ aryl, or $R^{12}$ and $R^{13}$, together with the nitrogen to which they are attached, form a 3-7 membered heterocyclic ring;
  wherein said alkyl and aryl groups and heterocyclic ring are optionally substituted with one to three $R^{20}$ groups;

$R^{14}$ at each occurrence is independently selected from $C_1$-$C_6$ alkyl, $C_6$-$C_{10}$ aryl, and arylalkyl;
  wherein said alkyl, aryl and arylalkyl groups are optionally substituted with one to three $R^{20}$ groups;

$R^{20}$ at each occurrence is independently selected from F, Cl, Br, I, $OR^{22}$, $OR^{25}$, $NR^{23}R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, and $S(O)_yR^{22}$;

$R^{21}$ at each occurrence is independently selected from H and $C_1$-$C_6$ alkyl;

$R^{22}$ at each occurrence is independently selected from H, $C_1$-$C_6$ alkyl, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring;

$R^{25}$ at each occurrence is independently the residue of an amino acid after the hydroxyl group of the carboxyl group is removed;

m is 0 or 1;
n is 0 or 1;
q is 0, 1, or 2;
y is 0, 1, or 2;

with the exclusion of the compounds wherein:
  Y is $C_2$ alkylene substituted with one to three $C_1$-$C_6$ alkylene and/or $NR^{23}R^{24}$ and/or $NR^{21}CO_2R^{22}$; and $R^1$ is $C(=O)NR^{12}R^{13}$;
or
Y is $C_2$ alkylene substituted with one to three $(C_1-C_6)$ alkyl; and
$R^1$ is phenyl optionally substituted with one to three groups $R^{20}$;
or
Y is $CH_2-Z-(CH_2)_n$ wherein n=0 or 1, and Z is cyclopropyl or cyclobutyl optionally substituted; and
$R^1$ is H or phenyl optionally substituted with one to three groups $R^{20}$;
or
Y is $CH_2$; and
$R^1$ is phenyl optionally substituted with one to three groups $R^{20}$;
or
Ar is a 5-10 membered heteroaryl group or a phenyl optionally substituted with one to three groups selected from $CF_3$, $NR^{21}C(=O)R^{22}$, $NO_2$ or $CO_2H$; and/or
X is $S(O)_y$; and
Y=$CH_2$ or $CH_2CH_2$; and
$R^1$ is H.
and with the exclusion of the compounds:
N-[2,6-bis(1-methylethyl)phenyl]-2-[[4-(2-pyridinylmethoxy)phenyl]methyl]thio]-acetamide;
tetrahydro-2-[[{4-(phenylthio)phenyl]methyl}thio]acetyl]-2H-1,2-oxazine; and
2-chloro-1-[3-[(methylsulfonyl)methyl]-4-nitrophenoxy]-4-(trifluoromethyl)-benzene and the stereoisomeric forms, mixtures of stereoisomeric forms or pharmaceutically acceptable salts forms thereof.

In a second embodiment, the present invention provides a compound of formula (I),

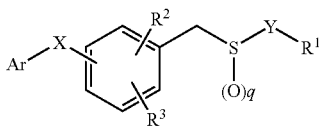

(I)

wherein:
Ar is independantly selected from $C_6-C_{10}$ aryl and 5 to 10-membered heteroaryl wherein:
$C_6-C_{10}$ aryl and heteroaryl are optionally substituted with one to three groups selected from F, Cl, Br, I, $OR^{22}$, $OR^{25}$, $NR^{23}R^{24}$, NHOH, $NO_2$, CN, $CF_3$, $C_1-C_6$ alkyl, $C_2-C_6$ alkenyl, $C_2-C_6$ alkynyl, $C_3-C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
X is O, $S(O)_y$, $N(R^{10})$, $OC(R^{22})_2$, $C(R^{22})_2O$, $C(R^{22})_2NR^{21}$, $NR^{21}C(R^{22})_2$, $C(=)N(R^{21})$, $NR^{21}C(=O)$, $S(O)_2NR^{22}$, $NR^{22}S(O)_2C(R^{22})_2$, $C(R^{22})_2$, $CR^{21}=CR^{21}$, $C\equiv C$;
Y is $C_1-C_6$ alkylene;
$(C_1-C_4$ alkylene$)_m-Z^1-(C_1-C_4$ alkylene$)_n$;
$C_1-C_4$ alkylene-$Z^2-C_1-C_4$ alkylene;
wherein said alkylene groups are optionally substituted with one to three $R^{20}$ groups;
$Z^1$ is $CR^{21}=CR^{21}$, $C\equiv C$, $C_6-C_{10}$ arylene, 5-10 membered heteroarylene,
$C_3-C_6$ cycloalkylene, or 3-6 membered heterocycloalkylene; wherein said arylene, heteroarylene, cycloalkylene, and heterocycloalkylene groups are optionally substituted with one to three $R^{20}$ groups;
$Z^2$ is O, $NR^{10A}$, or $S(O)_y$;
$R^1$ is selected from H, $C_6-C_{10}$ aryl, $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;
wherein said aryl groups are optionally substituted with one to three $R^{20}$ groups;
$R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1-C_6$ alkyl, $C_2-C_6$ alkenyl, $C_2-C_6$ alkynyl, $C_3-C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
$R^{10}$ and $R^{10A}$ are each independently selected from H, $C_1-C_6$ alkyl, $C_6-C_{10}$ aryl, $C(=O)R^{14}$, and $S(O)_yR^{14}$; wherein said alkyl and aryl groups are optionally substituted with one to three $R^{20}$ groups;
$R^{11}$ at each occurrence is independently selected from H, $C_1-C_6$ alkyl, and $C_6-C_{10}$ aryl;
wherein said alkyl and aryl groups are optionally substituted with one to three $R^{20}$ groups;
$R^{12}$ and $R^{13}$ at each occurrence are each independently selected from H, $C_1-C_6$ alkyl, and $C_6-C_{10}$ aryl, or $R^{12}$ and $R^{13}$, together with the nitrogen to which they are attached, form a 3-7 membered heterocyclic ring;
wherein said alkyl and aryl groups and heterocyclic ring are optionally substituted with one to three $R^{20}$ groups;
$R^{14}$ at each occurrence is independently selected from $C_1-C_6$ alkyl, $C_6-C_{10}$ aryl, and arylalkyl;
wherein said alkyl, aryl and arylalkyl groups are optionally substituted with one to three $R^{20}$ groups;
$R^{20}$ at each occurrence is independently selected from F, Cl, Br, I, $OR^{22}$, $OR^{25}$, $NR^{23}R^{24}$, NHOH, $NO_2$, CN, $CF_3$, $C_1-C_6$ alkyl optionally substituted by one to three OH, $C_2-C_6$ alkenyl, $C_2-C_6$ alkynyl, $C_3-C_7$ cycloalkyl, 3-7 membered heterocycloalkyl, phenyl, 5 or 6 membered heteroaryl, arylalkyl, =O, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
$R^{21}$ at each occurrence is independently selected from H and $C_1-C_6$ alkyl;
$R^{22}$ at each occurrence is independently selected from H, $C_1-C_6$ alkyl, and $C_6-C_{10}$ aryl;
$R^{23}$ and $R^{24}$ at each occurrence are each independently selected from H, $C_1-C_6$ alkyl, and $C_6-C_{10}$ aryl, or $R^{23}$ and $R^{24}$, together with the nitrogen to which they are attached, form a 3-7 membered heterocyclic ring;
$R^{25}$ at each occurrence is independently the residue of an amino acid after the hydroxyl group of the carboxyl group is removed;
m is 0 or 1;
n is 0 or 1;
q is 0, 1, or 2;
y is 0, 1, or 2;

and the stereoisomeric forms, mixtures of stereoisomeric forms or pharmaceutically acceptable salts forms thereof.

In another preferred embodiment of the invention, there are provided compounds of formula (Ia)

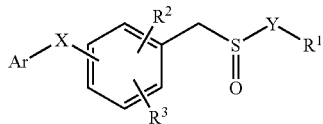

(Ia)

wherein:
Ar is independantly selected from $C_6$-$C_{10}$ aryl and 5 to 10-membered heteroaryl, wherein:
  $C_6$-$C_{10}$ aryl and heteroaryl are optionally substituted with one to three groups selected from F, Cl, Br, I, $OR^{22}$, $OR^{25}$, $NR^{23}R^{24}$, NHOH, $NO_2$, CN, $C_1$-$C_6$ alkyl, phenyl, arylalkyl, and $C(=O)R^{22}$;
X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2NR^{22}$, $NR^{22}S(O)_2$;
Y is $C_1$-$C_6$ alkylene;
  $C_1$-$C_4$ alkylene-$Z^1$—($C_1$-$C_4$ alkylene)$_n$; or
  $C_1$-$C_4$ alkylene-$Z^2$—$C_1$-$C_4$ alkylene;
  wherein said alkylene groups are optionally substituted with one to three $R^{20}$ groups;
$Z^1$ is $CR^{21}=CR^{21}$, $C{\equiv}C$, $C_6$-$C_{10}$ arylene, 5-10 membered heteroarylene,
  $C_3$-$C_6$ cycloalkylene, or 3-6 membered heterocycloalkylene;
$Z^2$ is O, $NR^{10A}$, or $S(O)_y$;
$R^1$ is selected from $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;
$R^2$ and $R^3$ are each independently selected from H, F, cl, Br, I, $OR^{22}$, $OR^{25}$, $NR^{23}R^{24}$, NHOH, $NO_2$, CN, $CF_3$, $C_1$-$C_6$ alkyl, phenyl, 5 or 6 membered heteroaryl, arylalkyl, $C(=O)R^{22}$;
$R^{10}$ and $R^{10A}$ are each independently selected from H, $C_1$-$C_6$ alkyl, $C(=O)R^{14}$, and $S(O)_yR^{14}$,
  wherein said alkyl groups are optionally substituted with one to three $R^{20}$ groups;
$R^{11}$ at each occurrence is independently selected from H, and $C_1$-$C_6$ alkyl; wherein said alkyl groups are optionally substituted with one to three $R^{20}$ groups;
$R^{12}$ and $R^{13}$ at each occurrence are each independently selected from H, and $C_1$-$C_6$ alkyl, or $R^{12}$ and $R^{13}$, together with the nitrogen to which they are attached, form a 3-7 membered heterocyclic ring;
  wherein said alkyl and aryl groups and heterocyclic ring are optionally substituted with one to three $R^{20}$ groups;
$R^{14}$ at each occurrence is independently selected from $C_1$-$C_6$ alkyl, $C_6$-$C_{10}$ aryl, and arylalkyl;
  wherein said alkyl, aryl and arylalkyl groups are optionally substituted with one to three $R^{20}$ groups;
$R^{20}$ at each occurrence is independently selected from F, Cl, Br, I, $OR^{22}$, $OR^{25}$, $NR^{23}R^{24}$, NHOH, $NO_2$, CN, $CF_3$, phenyl, benzyl, =O, $C(=O)R^{22}$, $CO_2R^{22}$, $OC(=O)R^{22}$, $C(=O)NR^{23}R^{24}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;
$R^{21}$ at each occurrence is independently selected from H and $C_1$-$C_6$ alkyl;
$R^{22}$ at each occurrence is independently selected from H, $C_1$-$C_6$ alkyl, and $C_6$-$C_{10}$ aryl;

$R^{23}$ and $R^{24}$ at each occurrence are each independently selected from H, and $C_1$-$C_6$ alkyl, or $R^{23}$ and $R^{24}$, together with the nitrogen to which they are attached, form a 3-7 membered heterocyclic ring;
$R^{25}$ at each occurrence is independently the residue of an amino acid after the hydroxyl group of the carboxyl group is removed;
n is 0 or 1;
y is 0, 1, or 2;

and the stereoisomeric forms, mixtures of stereoisomeric forms or pharmaceutically acceptable salts forms thereof.

An additional aspect of the present invention includes compounds of formula (A) and formulas (I) and (Ia) wherein Y is $C_1$-$C_6$ alkylene, $C_1$-$C_4$ alkylene-$Z^1$—$C_1$-$C_4$ alkylene, or $C_1$-$C_4$ alkylene-$Z^2$—$C_1$-$C_4$ alkylene, wherein said alkylene groups are optionally substituted with one to three $C_1$-$C_6$ alkyl groups; $Z^1$ is $CR^{21}=CR^{21}$, $C{\equiv}C$, or phenyl; $Z^2$ is O, $NR^{10A}$, or $S(O)_y$; $R^1$ is selected from $NR^{21}C(=O)R^{14}$, $C(=O)R^{14}$, $CO_2R^{11}$, $OC(=O)R^{11}$, and $C(=O)NR^{12}R^{13}$. In other aspects, Y is $C_1$-$C_6$ alkylene, or $C_1$-$C_4$ alkylene-$Z^1$—$C_1$-$C_4$ alkylene. In additional aspects, Y is $C_1$-$C_6$ alkylene. In further aspects, $R^1$ is $C(=O)NR^{12}R^{13}$.

In certain aspects of the present invention, there are included compounds of formula (A) and formulas (I) and (Ia) where Ar is phenyl. Other aspects include compounds where Ar is napthyl. Other aspects include compounds where Ar is thienyl. Other aspects include compounds where Ar is furyl.

In additional aspects of the present invention, there are included compounds of formula (A) and formulas (I) and (Ia) wherein Ar has any of the values of the previous embodiments and q is 1.

In other aspects of the present invention, there are included compounds of formula (A) and formulas (I) and (Ia) where X is O, $S(O)_y$, $N(R^{10})$, $OC(R^{22})_2$, $C(R^{22})_2NR^{21}$, $C(=O)N(R^{21})$, $S(O)_2NR^{22}$.

In additional aspects of the present invention, there are included compounds of formula (A) and formulas (I) and (Ia) where X is O, $S(O)_y$, $N(R^{10})$, $OC(R^{22})_2$, $C(R^{22})_2NR^{21}$, $C(=O)N(R^{21})$, $S(O)_2NR^{22}$ and q is 1.

Other aspects of the present invention include compounds of formula (A) and formulas (I) and (Ia) wherein Ar and X and q have any of the values of the previous embodiments, and Y is $C_1$-$C_6$ alkylene, particularly those where Y is $CH_2$ or $CH_2CH_2$, and most particularly those where Y is $CH_2$.

Additional aspects of the present invention include compounds of formula (A) and formulas (I) and (Ia) wherein Ar, X and q have any of the values of the previous embodiments, and Y is ($C_1$-$C_4$ alkylene)$_m$—$Z^1$—($C_1$-$C_4$ alkylene)$_n$ wherein $Z^1$ is $CR^{21}=CR^{21}$, $C{\equiv}C$, $C_6$-$C_{10}$ arylene, 5-10 membered heteroarylene, $C_3$-$C_6$ cycloalkylene, or 3-6 membered heterocycloalkylene. Other aspects include those compounds where Y is $C_1$-$C_4$ alkylene-$Z^1$. Other aspects include those where Y is $Z^1$—$C_1$-$C_4$ alkylene. Additional aspects include compounds where Y is $C_1$-$C_4$ alkylene-$Z^1$—$C_1$-$C_4$ alkylene.

Further aspects of the present invention include compounds of formula (A) and formulas (I) and (Ia) wherein Ar, X, Y, and q have any of the values of the previous embodiments, and $Z^1$ is $CR^{21}=CR^{21}$, or $C{\equiv}C$. Other aspects include compounds where $Z^1$ is $C_6$-$C_{10}$ arylene, or $C_3$-$C_6$ cycloalkylene, particularly those where $Z^1$ is phenyl. Other aspects include compounds where $Z^1$ is 5-10 membered heteroarylene, or 3-6 membered heterocycloalkylene.

Further aspects of the present invention include compounds of formula (A) and formulas (I) and (Ia) wherein Ar, X and q have any of the values of the previous embodiments, and Y is $(C_1\text{-}C_4 \text{ alkylene})_m\text{—}Z^2\text{—}(C_1\text{-}C_4 \text{ alkylene})$, wherein $Z^2$ is O, $NR^{10A}$, or $S(O)_y$. Other aspects include those compounds where Y is $C_1\text{-}C_4$ alkylene-$Z^2$, wherein $R^1$ cannot be H. Other aspects include those compounds where Y is $C_1\text{-}C_4$ alkylene-$Z^2$—$C_1\text{-}C_4$ alkylene. Additional aspects include any of the above embodiments of Y wherein $Z^2$ is O. Additional aspects include any of the above embodiments of Y wherein $Z^2$ is $NR^{10A}$.

Further aspects of the present invention include compounds of formula (A) and formulas (I) and (Ia) wherein Ar, Y, $Z^1$, and $Z^2$, and q have any of the values of the previous embodiments, and $R^1$ can be any value selected from the following 12 enumerated paragraphs:
1. H.
2. $NR^{12}R^{13}$.
3. $NR^{21}C(=O)R^{14}$.
4. $C(=O)R^{14}$.
5. $CO_2R^{11}$.
6. $OC(=O)R^{11}$.
7. $C(=O)NR^{12}R^{13}$.
8. $C(=NR^{11})NR^{12}R^{13}$.
9. $OC(=O)NR^{12}R^{13}$.
10. $NR^{21}S(O)_2R^{11}$.
11. $NR^{21}C(=O)NR^{12}R^{13}$.
12. $NR^{21}S(O)_2NR^{12}R^{13}$.

Other additional aspects of the present invention include compounds of formula (A) and formulas (I) and (Ia) wherein Ar, Y, $Z^1$, and $Z^2$, and q have any of the values of the previous embodiments, and $R^1$ can be a combination of the values selected from the previous 12 enumerated paragraphs. The preceding 12 enumerated paragraphs may be combined to further define additional preferred embodiments of compounds of the present invention. For example, one such combination includes $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$.

Another such combination includes $NR^{12}R^{13}$, wherein $R^{12}$ and $R^{13}$ are each independently selected from H and $C_1\text{-}C_6$ alkyl; $NR^{21}C(=O)R^{14}$; $C(=O)NR^{12}R^{13}$; $C(=NR^{11})NR^{12}R^{13}$; and $NR^{21}C(=O)NR^{12}R^{13}$.

A third such combination includes $C(=O)R^{14}$, $CO_2R^{11}$, $OC(=O)R^{11}$, $C(=O)NR^{12}R^{13}$, $OC(=O)NR^{12}R^{13}$, $NR^{21}S(O)_2R^{11}$, and $NR^{21}S(O)_2NR^{12}R^{13}$.

A fourth such combination includes $NR^{21}C(=O)R^{14}$, $C(=O)R^{14}$, $CO_2R^{11}$, $OC(=O)R^{11}$, and $C(=O)NR^{12}R^{13}$.

A fifth such combination includes $NR^{21}C(=O)R^{14}$ and $C(=O)NR^{12}R^{13}$.

In still further aspects of the present invention, there are included compounds of formula (Ib):

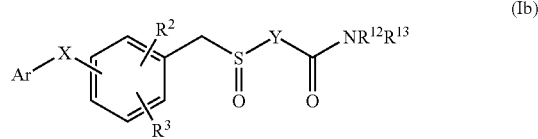

(Ib)

wherein Ar, X and Y have any of the values of the previous embodiments.

Additional aspects of the present invention include compounds of formula (A) and formulas (I), (Ia) and (Ib) wherein Ar, X, Y, $Z^1$, $Z^2$, $R^1$, and q have any of the values of the previous embodiments, and $R^{12}$ and $R^{13}$ are each independently selected from H and $C_1\text{-}C_6$ alkyl.

Other aspects of the present invention include compounds of formula (A) and formulas (I), (Ia) and (Ib) wherein Ar, Y, $Z^1$, $Z^2$, $R^1$, and q have any of the values of the previous embodiments, and $R^{12}$ and $R^{13}$ together with the nitrogen to which they are attached, form a 3-7 membered heterocyclic ring, particularly those where the heterocyclic ring is a heterocycloalkyl group, and more particularly those where the heterocyclic group is pyrrolidine or piperidine. In certain aspects, the heterocyclic ring is substituted with one $R^{20}$. In other aspects, the heterocyclic ring is unsubstituted.

Other aspects of the present invention include compounds of formula (A) and formulas (I), (Ia) and (Ib), wherein Y is $C_1\text{-}C_6$ alkylene and/or $R^1$ is selected from $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$.

In accordance with a preferred embodiment, Ar is a $C_6\text{-}C_{10}$ aryl, more preferably phenyl or naphthyl.

In accordance with another preferred embodiment, Ar is a 5-10 membered heteroaryl, notably a 5 or 6 membered heteroaryl such as thienyl or furyl.

Ar is optionally substituted with one to three groups, preferably selected from halogen atoms (F, Cl, Br, I), $OR^{22}$, or phenyl.

In that context, the following Ar substituents are particularly preferred.

Preferably, halogen atoms are Cl and F.

Preferably, $OR^{22}$ is $O(C_1\text{-}C_6)$ alkyl such as O-methyl, O-ethyl, O-isopropyl.

In accordance with a preferred embodiment, X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2NR^{22}$, $NR^{22}S(O)_2$.

Preferably, X is O, $S(O)_y$, NH, $OCH_2$, $CH_2O$, $CH_2NH$, $NHCH_2$, $C(=O)NH$, $NHC(=O)$, $S(O)_2NH$, $NHS(O)_2$, more preferably O, S, SO, NH, $OCH_2$, $CH_2NH$, $C(=O)NH$, $S(O)_2NH$.

In accordance with a preferred embodiment Y is $(C_1\text{-}C_6)$ alkylene, preferably unsubstituted $(C_1\text{-}C_6)$ alkylene and more preferably $CH_2$.

In accordance with a preferred embodiment, $R^1$ is selected from H, $CO_2R^{11}$, $C(=O)NR^{12}R^{13}$, and is more preferably a $C(=O)NR^{12}R^{13}$.

Preferably, $R^{12}$ and $R^{13}$, at each occurrence are each independently selected from H, $C_1\text{-}C_6$ alkyl, or $R^{12}$ and $R^{13}$ together with the nitrogen to which they are attached, form a 3-7 membered heterocyclic ring.

According to a preferred embodiment $R^{12}$ and $R^{13}$ together with the nitrogen to which they are attached, form a 3-7 membered heterocyclic ring, more preferably a 5-6 membered heterocyclic ring.

Preferably, the heterocyclic ring is a cycloalkyl group in which one or more ring atoms, more preferably one or two, are replaced by —N—.

Preferably, the heterocyclic ring is selected from the group consisting of pyrrolidinyl, piperidyl and piperazinyl.

The heterocyclic ring may be substituted with one to three $R^{20}$ groups, preferably independently selected from $C_1\text{-}C_6$ alkyl optionally substituted with one to three OH, $C(=O)R^{22}$, $CO_2R^{22}$, $C(=O)NR^{23}R^{24}$.

Examples of $R^{20}$ representing a $C(=O)R^{22}$ group are notably the groups wherein $R^{22}$ represents a $C_1\text{-}C_6$ alkyl group such as acetyl ($C(=O)CH_3$), or ethylcarbonyl ($C(=O)CH_2CH_3$).

Examples of $R^{20}$ representing a $CO_2R^{22}$ group are notably $CO_2R^{22}$ wherein $R^{22}$ is H or $C_1\text{-}C_6$ alkyl such as ter-butoxycarbonyl (Boc) ($CO_2(tBu)$).

Examples of $R^{20}$ representing a $C_1$-$C_6$ alkyl group optionally substituted with one to three OH are notably hydroxyethyl.

In accordance with another preferred embodiment, $R^{12}$ and $R^{13}$, at each occurrence are each independently selected from H or $C_1$-$C_6$ alkyl.

Examples of $R^{12}$, $R^{13}$ representing a $C_1$-$C_6$ alkyl group are notably methyl, ethyl, t-butyl, optionally substituted with one to three $R^{20}$ groups, notably OH or CN.

Examples of $C(=O)NR^{12}R^{13}$ wherein $R^{12}$ and $R^{13}$ are each independently selected from H or $C_1$-$C_6$ alkyl are notably $C(=O)NH_2$ or $C(=O)NMe_2$, $C(=O)NH(CH_2)_2OH$, $C(=O)NHCMe_3$.

In a prefered embodiment of the present invention there are provided compounds of formula (A) and formula (I):

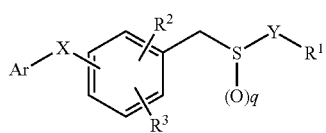

wherein Ar, X, $R^2$ and $R^3$, q, Y—$R^1$ are defined in the Table 1 below.

In Table 1, the term "position" refers to the position of the Ar—X lateral side chain as compared to —$CH^2$—$S(O)q$—Y—$R^1$ group on the central benzyl ring.

In addition, the positions of substituents on the Ar group and on the central core phenyl group are numbered as follows:

TABLE 1

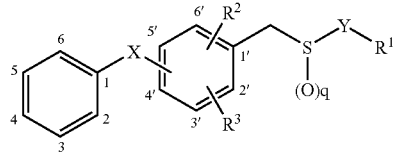

| Ex. n° | Ar | X | Position* | $R^2$ | $R^3$ | q | Y—$R^1$ |
|---|---|---|---|---|---|---|---|
| 13 | 3,4-DiClPh | O | para | H | H | 0 | $CH_2$CO-N-piperazinyl-N-Boc |
| 14 | 3,4-DiClPh | O | para | H | H | 0 | $CH_2$CO-N-piperazinyl |
| 19 | 3,4-DiClPh | O | para | H | H | 1 | $CH_2$CO-N-piperazinyl |
| 16 | 4-ClPh | S | para | H | H | 0 | $CH_2$CO-1-(4-acetyl)-piperazinyl |
| 23 | 4-ClPh | S | para | H | H | 1 | $CH_2$CO-1-(4-acetyl)-piperazinyl |
| 24 | 4-ClPh | SO | para | H | H | 1 | $CH_2$CO-1-(4-acetyl)-piperazinyl |
| 29 | Ph | O | para | H | H | 1 | $CH_2$CONHCHMe$_2$ |
|  | Ph | O | meta | H | H | 0 | $CH_2$CO-N-pyrrolidinyl |
| 31 | Ph | O | meta | H | H | 1 | $CH_2$CO-N-pyrrolidinyl |
|  | Ph | O | meta | H | H | 0 | $CH_2$CONH$_2$ |
| 32 | Ph | O | meta | H | H | 1 | $CH_2$CONH$_2$ |
|  | Ph | O | meta | H | H | 0 | $CH_2$CONMe$_2$ |
| 33 | Ph | O | meta | H | H | 1 | $CH_2$CONMe$_2$ |
|  | Ph | O | meta | H | H | 0 | $CH_2$CONHCHMe$_2$ |
| 34 | Ph | O | meta | H | H | 1 | $CH_2$CONHCHMe$_2$ |
|  | Ph | O | meta | H | H | 0 | $CH_2$CO-1-(4-acetyl)-piperazinyl |
| 35 | Ph | O | meta | H | H | 1 | $CH_2$CO-1-(4-acetyl)-piperazinyl |
|  | 4-OCH$_3$Ph | O | para | H | H | 0 | $CH_2$CONH$_2$ |
| 36 | 4-OCH$_3$Ph | O | para | H | H | 1 | $CH_2$CONH$_2$ |
|  | 4-OCH$_3$Ph | O | para | H | H | 0 | $CH_2$CO-1-(4-acetyl)-piperazinyl |
| 37 | 4-OCH$_3$Ph | O | para | H | H | 1 | $CH_2$CO-1-(4-acetyl)-piperazinyl |
|  | 4-OCH$_3$Ph | O | para | H | H | 0 | $CH_2$CO-N-piperazinyl |
| 38 | 4-OCH$_3$Ph | O | para | H | H | 1 | $CH_2$CO-N-piperazinyl |
|  | 3,4-DiClPh | O | para | H | H | 0 | $CH_2$CONH$_2$ |
| 39 | 3,4-DiClPh | O | para | H | H | 1 | $CH_2$CONH$_2$ |
| 11 | 3,4-DiClPh | O | para | H | H | 0 | $CH_2$CO-1-(4-acetyl)-piperazinyl |
| 22 | 3,4-DiClPh | O | para | H | H | 1 | $CH_2$CO-1-(4-acetyl)-piperazinyl |
| 27 | 3,4-DiClPh | O | para | H | H | 2 | $CH_2$CO-1-(4-acetyl)-piperazinyl |
| 30 | 3,4-DiClPh | O | para | H | H | 1 | $CH_2$COOH |
| 15 | 3,4-DiClPh | O | ortho | H | H | 0 | $CH_2$CONH$_2$ |
| 20 | 3,4-DiClPh | O | ortho | H | H | 1 | $CH_2$CONH$_2$ |
|  | 3,4-DiClPh | O | ortho | H | H | 0 | $CH_2$CO-1-(4-acetyl)-piperazinyl |

TABLE 1-continued

| Ex. n° | Ar | X | Position* | R² | R³ | q | Y—R¹ |
|---|---|---|---|---|---|---|---|
| 40 | 3,4-DiClPh | O | ortho | H | H | 1 | CH₂CO-1-(4-acetyl)-piperazinyl |
|  | 3,4-DiClPh | O | para | H | H | 0 | CH₂CO-1-(4-carboxamide)-piperazinyl |
| 41 | 3,4-DiClPh | O | para | H | H | 1 | CH₂CO-1-(4-carboxamide)-piperazinyl |
|  | 4-OCH₃Ph | O | ortho | H | H | 0 | CH₂CONH₂ |
| 42 | 4-OCH₃Ph | O | ortho | H | H | 1 | CH₂CONH₂ |
|  | 2-ClPh | O | para | H | H | 0 | CH₂CONH₂ |
| 43 | 2-ClPh | O | para | H | H | 1 | CH₂CONH₂ |
|  | 4-OHPh | O | ortho | H | H | 0 | CH₂CONH₂ |
| 44 | 4-OHPh | O | ortho | H | H | 1 | CH₂CONH₂ |
|  | 2-ClPh | O | ortho | H | H | 0 | CH₂CONH₂ |
| 45 | 2-ClPh | O | ortho | H | H | 1 | CH₂CONH₂ |
|  | 2-ClPh | O | para | H | H | 0 | CH₂CO-1-(4-acetyl)-piperazinyl |
| 46 | 2-ClPh | O | para | H | H | 1 | CH₂CO-1-(4-acetyl)-piperazinyl |
|  | 2-ClPh | O | para | H | H | 0 | CH₂CO-N-piperazinyl |
| 47 | 2-ClPh | O | para | H | H | 1 | CH₂CO-N-piperazinyl |
|  | 4-FPh | O | para | H | H | 0 | CH₂CO-1-(4-acetyl)-piperazinyl |
| 48 | 4-FPh | O | para | H | H | 1 | CH₂CO-1-(4-acetyl)-piperazinyl |
| 95 | 4-FPh | O | para | H | H | 2 | CH₂CO-1-(4-acetyl)-piperazinyl |
| 96 | 4-FPh | O | para | H | H | 1 | CH₂COOH |
|  | 4-FPh | O | ortho | H | H | 0 | CH₂CO-1-(4-acetyl)-piperazinyl |
| 49 | 4-FPh | O | ortho | H | H | 1 | CH₂CO-1-(4-acetyl)-piperazinyl |
|  | 4-FPh | O | para | H | H | 0 | CH₂CONH₂ |
| 50 | 4-FPh | O | para | H | H | 1 | CH₂CONH₂ |
|  | 4-FPh | O | ortho | H | H | 0 | CH₂CONH₂ |
| 51 | 4-FPh | O | ortho | H | H | 1 | CH₂CONH₂ |
|  | 2-Naphthyl | O | ortho | H | H | 0 | CH₂CONH₂ |
| 52 | 2-Naphthyl | O | ortho | H | H | 1 | CH₂CONH₂ |
|  | 2-Naphthyl | O | ortho | H | H | 0 | CH₂CO-1-(4-acetyl)-piperazinyl |
| 53 | 2-Naphthyl | O | ortho | H | H | 1 | CH₂CO-1-(4-acetyl)-piperazinyl |
|  | 2-Naphthyl | O | para | H | H | 0 | CH₂CONH₂ |
| 54 | 2-Naphthyl | O | para | H | H | 1 | CH₂CONH₂ |
|  | 2-BiPh | O | para | H | H | 0 | CH₂CONH₂ |
| 55 | 2-BiPh | O | para | H | H | 1 | CH₂CONH₂ |
|  | 2-BiPh | O | ortho | H | H | 0 | CH₂CONH₂ |
| 56 | 2-BiPh | O | ortho | H | H | 1 | CH₂CONH₂ |
|  | 2-ClPh | O | ortho | H | H | 0 | CH₂CO-1-(4-acetyl)-piperazinyl |
| 57 | 2-ClPh | O | ortho | H | H | 1 | CH₂CO-1-(4-acetyl)-piperazinyl |
|  | 2-Naphthyl | O | para | H | H | 0 | CH₂CO-1-(4-acetyl)-piperazinyl |
| 58 | 2-Naphthyl | O | para | H | H | 1 | CH₂CO-1-(4-acetyl)-piperazinyl |
|  | 2-BiPh | O | ortho | H | H | 0 | CH₂CO-1-(4-acetyl)-piperazinyl |
| 59 | 2-BiPh | O | ortho | H | H | 1 | CH₂CO-1-(4-acetyl)-piperazinyl |
|  | 2-BiPh | O | para | H | H | 0 | CH₂CO-1-(4-acetyl)-piperazinyl |
| 60 | 2-BiPh | O | para | H | H | 1 | CH₂CO-1-(4-acetyl)-piperazinyl |
|  | 4-ClPh | O | para | H | H | 0 | CH₂CO-1-(4-acetyl)-piperazinyl |

TABLE 1-continued

Structure: Ar-X-(phenyl with R2, R3)-CH2-S(O)q-Y-R1

| Ex. n° | Ar | X | Position* | R² | R³ | q | Y—R¹ |
|---|---|---|---|---|---|---|---|
| 61 | 4-ClPh | O | para | H | H | 1 | CH₂CO-1-(4-acetyl)-piperazinyl |
|  | 4-OCH₃Ph | O | para | H | H | 0 | CH₂CO-1-(4-methyl)-piperazinyl |
| 62 | 4-OCH₃Ph | O | para | H | H | 1 | CH₂CO-1-(4-methyl)-piperazinyl |
|  | 3,4-DiClPh | O | para | H | H | 0 | CH₂CO-1-(4-ethylcarboxylate)-piperazinyl |
| 63 | 3,4-DiClPh | O | para | H | H | 1 | CH₂CO-1-(4-ethylcarboxylate)-HHpiperazinyl |
|  | 4-FPh | O | para | H | H | 0 | CH₂CO-1-(4-hydroxyethyl)-piperazinyl |
| 64 | 4-FPh | O | para | H | H | 1 | CH₂CO-1-(4-hydroxyethyl)-piperazinyl |
|  | 3,4-DiClPh | O | ortho | H | H | 0 | CH₂CO-1-(4-hydroxyethyl)-piperazinyl |
| 65 | 3,4-DiClPh | O | ortho | H | H | 1 | CH₂CO-1-(4-hydroxyethyl)-piperazinyl |
|  | 4-FPh | O | para | H | H | 0 | CH₂CO-1-(4-methyl)-piperazinyl |
| 66 | 4-FPh | O | para | H | H | 1 | CH₂CO-1-(4-methyl)-piperazinyl |
|  | 4-ClPh | O | para | H | H | 0 | CH₂CONH2 |
| 67 | 4-ClPh | O | para | H | H | 1 | CH₂CONH2 |
|  | 4-FPh | O | para | H | H | 0 | CH₂CO-1-(4-ethylcarboxylate)-piperazinyl |
| 68 | 4-FPh | O | para | H | H | 1 | CH₂CO-1-(4-ethylcarboxylate)-piperazinyl |
|  | 4-OCH₃Ph | O | para | H | H | 0 | CH₂CO-1-(4-ethylcarboxylate)-piperazinyl |
| 69 | 4-OCH₃Ph | O | para | H | H | 1 | CH₂CO-1-(4-ethylcarboxylate)-piperazinyl |
|  | 4-ClPh | S | para | H | H | 0 | CH₂CO-1-(4-ethylcarboxylate)-piperazinyl |
| 70 | 4-ClPh | S | para | H | H | 1 | CH₂CO-1-(4-ethylcarboxylate)-piperazinyl |
| 71 | 4-ClPh | SO | para | H | H | 1 | CH₂CO-1-(4-ethylcarboxylate)-piperazinyl |
|  | 3,4-DiClPh | O | ortho | H | H | 0 | CH₂CO-1-(4-ethylcarboxylate)-piperazinyl |
| 72 | 3,4-DiClPh | O | ortho | H | H | 1 | CH₂CO-1-(4-ethylcarboxylate)-piperazinyl |
|  | Ph | O | ortho | H | H | 0 | CH₂CONH2 |
| 97 | Ph | O | ortho | H | H | 1 | CH₂CONH2 |
|  | Ph | O | ortho | H | H | 0 | CH₂CO-N-pyrrolidinyl |
| 98 | Ph | O | ortho | H | H | 1 | CH₂CO-N-pyrrolidinyl |
|  | Ph | O | ortho | H | H | 0 | CH₂CONMe₂ |
| 99 | Ph | O | ortho | H | H | 1 | CH₂CONMe₂ |
|  | Ph | O | para | H | H | 0 | CH₂CONMe₂ |

TABLE 1-continued

| Ex. n° | Ar | X | Position* | R² | R³ | q | Y—R¹ |
|---|---|---|---|---|---|---|---|
| 100 | Ph | O | para | H | H | 1 | CH₂CONMe₂ |
|  | Ph | O | para | H | H | 0 | CH₂CO-N-pyrrolidinyl |
| 101 | Ph | O | para | H | H | 1 | CH₂CO-N-pyrrolidinyl |
|  | Ph | O | para | H | H | 0 | CH₂CONH₂ |
| 102 | Ph | O | para | H | H | 1 | CH₂CONH₂ |
|  | Ph | O | ortho | H | H | 0 | CH₂CONHCH₂CN |
| 103 | Ph | O | ortho | H | H | 1 | CH₂CONHCH₂CN |
|  | Ph | O | ortho | H | H | 0 | CH₂CONHCHMe₂ |
| 104 | Ph | O | ortho | H | H | 1 | CH₂CONHCHMe₂ |
|  | Ph | O | ortho | H | H | 0 | CH₂CONHCMe₃ |
| 105 | Ph | O | ortho | H | H | 1 | CH₂CONHCMe₃ |
|  | Ph | O | ortho | H | H | 0 | CH₂CO-1-(4-hydroxy)-piperidinyl |
| 106 | Ph | O | ortho | H | H | 1 | CH₂CO-1-(4-hydroxy)-piperidinyl |
| 12 | Ph | O | ortho | H | H | 0 | CH₂CONH(CH₂)₂OH |
| 21 | Ph | O | ortho | H | H | 1 | CH₂CONH(CH₂)₂OH |
|  | Ph | O | ortho | H | H | 0 | CH₂CO-1-(4-acetyl)-piperazinyl |
| 107 | Ph | O | ortho | H | H | 1 | CH₂CO-1-(4-acetyl)-piperazinyl |
|  | Ph | O | meta | H | H | 0 | CH₂CONH(CH₂)₂OH |
| 108 | Ph | O | meta | H | H | 1 | CH₂CONH(CH₂)₂OH |
|  | Ph | O | meta | H | H | 0 | CH₂CO-1-(4-hydroxy)-piperidinyl |
| 109 | Ph | O | meta | H | H | 1 | CH₂CO-1-(4-hydroxy)-piperidinyl |
| 110 | Ph | O | para | H | H | 1 | CH₂CO-1-(4-acetyl)-piperazinyl |
| 111 | Ph | O | para | H | H | 1 | CH₂CONH(CH₂)₂OH |
| 112 | Ph | O | para | H | H | 1 | CH₂CO-1-(4-hydroxy)-piperidinyl |
| 113 | 4-ClPh | CONH | ortho | H | H | 1 | CH₂CONH2 |
| 114 | 3,4-DiOCH₃Ph | CONH | ortho | H | H | 1 | CH₂CONH2 |
| 115 | 2-Naphthyl | CONH | ortho | H | H | 1 | CH₂CONH2 |
| 116 | 4-ClPh | CONH | ortho | H | H | 1 | CH₂CO-1-(4-acetyl)-piperazinyl |
| 117 | 3,4DiFPh | CONH | ortho | H | H | 1 | CH₂CONH₂ |
| 118 | 2,4-DiOCH₃Ph | CONH | ortho | H | H | 1 | CH₂CONH₂ |
| 119 | 3,4,5-TriOCH₃Ph | CONH | ortho | H | H | 1 | CH₂CONH₂ |
| 120 | 3,4-DiOCH₃Ph | CONH | meta | H | H | 1 | CH₂CONH₂ |
| 121 | 2,4-DiOCH₃Ph | CONH | ortho | H | H | 1 | CH₂CO-1-(4-acetyl)-piperazinyl |
| 122 | 3,4-DiOCH₃Ph | CONH | ortho | H | H | 1 | CH₂CO-1-(4-acetyl)-piperazinyl |
| 123 | 4-FPh | CONH | ortho | H | H | 1 | CH₂CO-1-(4-acetyl)-piperazinyl |
| 124 | 3,4-DiClPh | CONH | ortho | H | H | 1 | CH₂CO-1-(4-acetyl)-piperazinyl |
| 125 | 2,4-DiOCH₃Ph | CONH | meta | H | H | 1 | CH₂CONH₂ |
| 126 | 4-FPh | CONH | meta | H | H | 1 | CH₂CONH₂ |
| 127 | 3,4-DiClPh | CONH | meta | H | H | 1 | CH₂CONH₂ |
| 7 | 4-ClPh | O | para | H | H | 0 | CH₃ |
| 8 | 4-ClPh | O | para | H | H | 1 | CH₃ |
| 9 | 4-ClPh | O | para | H | H | 1 | CH₂[4(4-ClPhenoxy)phenyl] |
|  | 3,4-DiClPh | O | para | H | H | 0 | CH₃ |
| 10 | 3,4-DiClPh | O | para | H | H | 1 | CH₃ |
|  | 4-ClPh | S | ortho | H | H | 0 | CH₂CO-N-piperazinyl |
| 73 | 4-ClPh | S | ortho | H | H | 1 | CH₂CO-N-piperazinyl |
|  | 2,3-DiClPh | O | ortho | H | H | 0 | CH₂CO-1-(4-acetyl)-piperazinyl |

TABLE 1-continued

Structure: Ar ring (positions 1-6) — X — phenyl ring (positions 1'-6' with R² at 6', R³ at 3') — CH₂ — S(O)q — Y — R¹

| Ex. n° | Ar | X | Position* | R² | R³ | q | Y—R¹ |
|---|---|---|---|---|---|---|---|
| 74 | 2,3-DiClPh | O | ortho | H | H | 1 | CH₂CO-1-(4-acetyl)-piperazinyl |
|  | 2,5-DiClPh | O | ortho | H | H | 0 | CH₂CO-1-(4-acetyl)-piperazinyl |
| 75 | 2,5-DiClPh | O | ortho | H | H | 1 | CH₂CO-1-(4-acetyl)-piperazinyl |
|  | 2,5-DiClPh | O | ortho | H | H | 0 | CH₂CONH₂ |
| 76 | 2,5-DiClPh | O | ortho | H | H | 1 | CH₂CONH₂ |
|  | 2,3-DiClPh | O | ortho | H | H | 0 | CH₂CONH₂ |
| 77 | 2,3-DiClPh | O | ortho | H | H | 1 | CH₂CONH₂ |
|  | 2,4-DiClPh | O | para | H | H | 0 | CH₂CO-1-(4-acetyl)-piperazinyl |
| 78 | 2,4-DiClPh | O | para | H | H | 1 | CH₂CO-1-(4-acetyl)-piperazinyl |
|  | 2,4-DiClPh | O | ortho | H | H | 0 | CH₂CO-1-(4-acetyl)-piperazinyl |
| 79 | 2,4-DiClPh | O | ortho | H | H | 1 | CH₂CO-1-(4-acetyl)-piperazinyl |
|  | 2,4-DiClPh | O | para | H | H | 0 | CH₂CONH₂ |
| 80 | 2,4-DiClPh | O | para | H | H | 1 | CH₂CONH₂ |
|  | 2,4-DiClPh | O | ortho | H | H | 0 | CH₂CONH₂ |
| 81 | 2,4-DiClPh | O | ortho | H | H | 1 | CH₂CONH₂ |
|  | 3,5-DiClPh | O | ortho | H | H | 0 | CH₂CO-1-(4-acetyl)-piperazinyl |
| 82 | 3,5-DiClPh | O | ortho | H | H | 1 | CH₂CO-1-(4-acetyl)-piperazinyl |
|  | 3,5-DiClPh | O | para | H | H | 0 | CH₂CO-1-(4-acetyl)-piperazinyl |
| 83 | 3,5-DiClPh | O | para | H | H | 1 | CH₂CO-1-(4-acetyl)-piperazinyl |
|  | 3,5-DiClPh | O | para | H | H | 0 | CH₂CONH₂ |
| 84 | 3,5-DiClPh | O | para | H | H | 1 | CH₂CONH₂ |
|  | 3,5-DiClPh | O | ortho | H | H | 0 | CH₂CONH₂ |
| 85 | 3,5-DiClPh | O | ortho | H | H | 1 | CH₂CONH₂ |
|  | 2,5-DiClPh | O | para | H | H | 0 | CH₂CO-1-(4-acetyl)-piperazinyl |
| 86 | 2,5-DiClPh | O | para | H | H | 1 | CH₂CO-1-(4-acetyl)-piperazinyl |
|  | 3,4-DiClPh | S | para | H | H | 0 | CH₂CO-1-(4-acetyl)-piperazinyl |
| 87 | 3,4-DiClPh | S | para | H | H | 1 | CH₂CO-1-(4-acetyl)-piperazinyl |
|  | 2,5-DiClPh | S | para | H | H | 0 | CH₂CONH₂ |
| 88 | 2,5-DiClPh | S | para | H | H | 1 | CH₂CONH₂ |
|  | 3,4-DiClPh | S | para | H | H | 0 | CH₂CONH₂ |
| 89 | 3,4-DiClPh | S | para | H | H | 1 | CH₂CONH₂ |
|  | 2,3-DiClPh | O | para | H | H | 0 | CH₂CO-1-(4-acetyl)-piperazinyl |
| 90 | 2,3-DiClPh | O | para | H | H | 1 | CH₂CO-1-(4-acetyl)-piperazinyl |
|  | 2,6-DiClPh | O | para | H | H | 0 | CH₂CO-1-(4-acetyl)-piperazinyl |
| 91 | 2,6-DiClPh | O | para | H | H | 1 | CH₂CO-1-(4-acetyl)-piperazinyl |
|  | 2,6-DiClPh | O | para | H | H | 0 | CH₂CONH₂ |
| 92 | 2,6-DiClPh | O | para | H | H | 1 | CH₂CONH₂ |
|  | 2,3-DiClPh | O | para | H | H | 0 | CH₂CONH₂ |
| 93 | 2,3-DiClPh | O | para | H | H | 1 | CH₂CONH₂ |
| 94 | 2,3-DiClPh | O | para | H | H | 2 | CH₂CONH₂ |
| 135 | Ph | NH | ortho | H | H | 1 | CH₂CO-1-(4-acetyl)-piperazinyl |
| 136 | Ph | NH | para | H | H | 1 | CH₂CO-1-(4-acetyl)-piperazinyl |
| 134 | 4-OCH₃Ph | NH | ortho | H | H | 1 | CH₂CO-1-(4-acetyl)-piperazinyl |
| 131 | 4-FPh | SO₂NH | para | H | H | 1 | CH₂CO-1-(4-acetyl)-piperazinyl |

TABLE 1-continued

| Ex. n° | Ar | X | Position* | R² | R³ | q | Y—R¹ |
|---|---|---|---|---|---|---|---|
| 137 | 4-OCH₃Ph | NH | para | H | H | 1 | CH₂CO-1-(4-acetyl)-piperazinyl |
| 138 | 4-FPh | NH | para | H | H | 1 | CH₂CO-1-(4-acetyl)-piperazinyl |
| 139 | 4-ClPh | NH | para | H | H | 1 | CH₂CO-1-(4-acetyl)-piperazinyl |
| 140 | 4-FPh | NH | para | H | H | 1 | CH₂CO-1-(4-acetyl)-piperazinyl |
| 128 | 3,4-DiClPh | CONH | para | H | H | 1 | CH₂CO-1-(4-acetyl)-piperazinyl |
| 129 | 4-FPh | CONH | para | H | H | 1 | CH₂CO-1-(4-acetyl)-piperazinyl |
| 141 | 3,4-DiClPh | NH | para | H | H | 1 | CH₂CO-1-(4-acetyl)-piperazinyl |
| 132 | 4-ClPh | SO₂NH | para | H | H | 1 | CH₂CO-1-(4-acetyl)-piperazinyl |
| 147 | 4-FPh | CH₂NH | para | H | H | 1 | CH₂CO-1-(4-acetyl)-piperazinyl |
| 133 | 3,4-DiClPh | SO₂NH | para | H | H | 1 | CH₂CO-1-(4-acetyl)-piperazinyl |
| 148 | 3,4-DiClPh | CH₂NH | para | H | H | 1 | CH₂CO-1-(4-acetyl)-piperazinyl |
| 149 | 4-FPh | CH₂NH | ortho | H | H | 1 | CH₂CO-1-(4-acetyl)-piperazinyl |
| 146 | 3,4-DiClPh | CH₂NH | ortho | H | H | 1 | CH₂CO-1-(4-acetyl)-piperazinyl |
| 130 | 3,4-DiClPh | SO₂NH | ortho | H | H | 1 | CH₂CO-1-(4-acetyl)-piperazinyl |
| 145 | 2-Furyl | CH₂NH | ortho | H | H | 1 | CH₂CO-1-(4-acetyl)-piperazinyl |
| 144 | 2-Thienyl | CH₂NH | ortho | H | H | 1 | CH₂CO-1-(4-acetyl)-piperazinyl |
| 142 | 2-Thienyl | CONH | ortho | H | H | 1 | CH₂CO-1-(4-acetyl)-piperazinyl |
| 143 | 2-Furyl | CONH | ortho | H | H | 1 | CH₂CO-1-(4-acetyl)-piperazinyl |
| 152 | Ph | OCH₂ | ortho | H | H | 0 | CH₂CONH2 |
| 153 | Ph | OCH₂ | ortho | H | H | 1 | CH₂CONH2 |
| 17 | 4-ClPh | O | para | 2'-Cl | H | 0 | CH₂CO-1-(4-acetyl)-piperazinyl |
| 18 | 4-ClPh | O | para | 2'-Cl | H | 0 | CH₂CONH₂ |
| 25 | 4-ClPh | O | para | 2'-Cl | H | 1 | CH₂CO-1-(4-acetyl)-piperazinyl |
| 26 | 4-ClPh | O | para | 2'-Cl | H | 1 | CH₂CONH₂ |
| 149a | 3,4-DiClPh | CONH | para | H | H | 1 | CH₂CONH₂ |
| 109a | 4-ClPh | O | ortho | H | H | 1 | CH₂CONH₂ |
| 109b | 3-Cl-4-FPh | O | ortho | H | H | 1 | CH₂CONH₂ |
| 109c | 4-Cl-3-FPh | O | ortho | H | H | 1 | CH₂CONH₂ |
| 109d | 3-Cl-4-FPh | O | ortho | H | H | 2 | CH₂CONH₂ |
| 10a | 4-ClPh | O | ortho | 4'-Cl | H | 0 | CH₂COOH |
| 18a | 4-ClPh | O | ortho | 4'-Cl | H | 0 | CH₂CONH₂ |
| 27a | 4-ClPh | O | ortho | 4'-Cl | H | 1 | CH₂CONH₂ |
| 27b | 4-ClPh | O | ortho | 4'-Cl | H | 2 | CH₂CONH₂ |
| 109e | 3,4-DiFPh | O | ortho | 4'-Cl | H | 1 | CH₂CONH₂ |
| 109f | 3,4-DiClPh | O | ortho | H | H | 2 | CH₂CONH₂ |
| 30a | 3,4-DiClPh | O | ortho | H | H | 1 | CH₂COOH |
| 30d | 3,4-DiClPh | O | ortho | H | H | 0 | CH₂COOMenthyl (1R,2S,5R) |
| 30e | 3,4-DiClPh | O | ortho | H | H | 1 (−) | CH₂CO0H |
| 30f | 3,4-DiClPh | O | ortho | H | H | 1 (+) | CH₂COOH |
| 20a | 3,4-DiClPh | O | ortho | H | H | 1 (−) | CH₂CONH₂ |
| 20b | 3,4-DiClPh | O | ortho | H | H | 1 (+) | CH₂CONH₂ |
| 30b | 3,4-DiClPh | O | ortho | H | H | 2 | CH₂COOH |
| 112a | 3,4-DiClPh | O | ortho | H | H | 1 | CH₂CONHCH₃ |

TABLE 1-continued

[Structure: Ar-X-phenyl-CH2-S(O)q-Y-R1 with positions 2', 3', 4' and R2, R3 substituents]

| Ex. n° | Ar | X | Position* | $R^2$ | $R^3$ | q | Y—$R^1$ |
|---|---|---|---|---|---|---|---|
| 112b | 3,4-DiClPh | O | ortho | H | H | 1 | $CH_2CON(C_2H_5)_2$ |
| 30f | 3,4-DiClPh | O | ortho | H | H | 0 | $CH_2CON(CH_3)_2$ |
| 30g | 3,4-DiClPh | O | ortho | H | H | 1 | $CH_2CON(CH_3)_2$ |

Ph = phenyl, ClPh = chlorophenyl, DiClPh = di-chlorophenyl, FPh = Fluoroprophenyl.
*Position: Ortho is position 2', meta is position 3' and para is position 4'.

In a second embodiment, the present invention provides a method for treatment of diseases comprising administering to a subject in need thereof a therapeutically effective amount of a compound of formula (A) and formula (I), or a pharmaceutically acceptable salt thereof. In a preferred embodiment, the present invention is to provide methods of treating or preventing diseases or disorders, including treatment of sleepiness, promotion and/or improvement of wakefulness, preferably improvement of wakefulness in patients with excessive sleepiness associated with narcolepsy, sleep apnea, preferably obstructive sleep apnea/hypopnea, and shift work disorder; treatment of Parkinson's disease; Alzheimer's disease; cerebral ischemia; stroke; eating disorders; attention deficit disorder ("ADD"), attention deficit hyperactivity disorder ("ADHD"); depression; schizophrenia; fatigue, preferably fatigue associated with cancer or neurological diseases, such as multiple sclerosis and chronic fatigue syndrome; stimulation of appetite and weight gain and improvement of cognitive dysfunction.

In a third embodiment, the present invention provides a pharmaceutical compositions comprising the compounds of formula (A) and formula (I) wherein the compositions comprise one or more pharmaceutically acceptable excipients and a therapeutically effective amount of at least one of the compounds of the present invention, or a pharmaceutically acceptable salt or ester form thereof.

In a fourth embodiment, the present invention provides for the use of compounds of formula (A) and formula (I) or pharmaceutically acceptable salts thereof for the manufacture of a medicament for the treatment of a disease or disorder.

These and other objects, features and advantages of the benzyl-thioalkyl derivatives will be disclosed in the following detailed description of the patent disclosure.

Definitions

The following terms and expressions contained herein are defined as follows:

As used herein, the term "about" refers to a range of values from ±10% of a specified value. For example, the phrase "about 50 mg" includes ±10% of 50, or from 45 to 55 mg.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" refers to a straight chain, or branched hydrocarbon chains of 2 to 8 carbon atoms having at least one carbon-carbon triple bond. A designation "$C_2$-$C_8$ alkynyl" refers to an alkynyl radical containing from 2 to 8 carbon atoms. Examples include ethynyl, propynyl, isopropynyl, 3,5-hexadiynyl, etc.

As used herein, the term "alkylene" refers to a substituted or unsubstituted, branched or straight chained hydrocarbon of 1 to 8 carbon atoms, which is formed by the removal of two hydrogen atoms. A designation such as "$C_1$-$C_4$ alkylene" refers to an alkylene radical containing from 1 to 4 carbon atoms. Examples include methylene (—$CH_2$—), propylidene ($CH_3CH_2CH$=), 1,2-ethandiyl (—$CH_2CH_2$—), etc.

As used herein, the term "phenylene" refers to a phenyl group with an additional hydrogen atom removed, i.e. a moiety with the structure of:

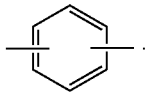

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_5$-$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include such groups as cyclopropyl, cyclobutyl, cyclopentyl, cyclohexl, cycloheptyl, cyclooctyl, pinenyl, and adamantanyl.

As used herein, the term "aryl" refers to a substituted or unsubstituted, mono- or bicyclic hydrocarbon aromatic ring system having 6 to 12 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the terms "heterocycle", "heterocyclic" or "heterocyclyl" refer to a substituted or unsubstituted carbocyclic group in which the ring portion includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

As used herein, the term "heterocycloalkyl" refers to a cycloalkyl group in which one or more ring carbon atoms are replaced by at least one hetero atom such as —O—, —N—, or —S—. Examples of heterocycloalkyl groups include pyrrolidinyl, pyrrolinyl, imidazolidinyl, imidazolinyl, pirazolidinyl, pirazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include pyrrolyl, furanyl, thienyl, pirazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl, etc.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-$NH_2$. In certain embodiments, substituent groups for the compounds of the present invention include the residue of an amino acid after removal of the hydroxyl moiety of the carboxyl group thereof; i.e., groups of formula —C(=O)CH($NH_2$)-(side chain). The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, $2^{nd}$ ed.; Worth Publishers: New York, 1975; 71-77, the disclosure of which is incorporated herein by reference. Non-naturally occurring amino acids also include α-amino acids wherein the side chains are replaced with synthetic derivatives. Representative side chains of naturally occurring and non-naturally occurring a-amino acids are shown below in Table 2.

TABLE 2

| | | |
|---|---|---|
| H | $CH_3$ | $CH(CH_3)_2$ |
| $CH_2CH(CH_3)_2$ | $CH(CH_3)CH_2CH_3$ | $CH_2OH$ |
| $CH_2SH$ | $CH(OH)CH_3$ | $CH_2CH_2SCH_3$ |
| $CH_2C_6H_5$ | $(CH_2)_4NH_2$ | $(CH_2)_3NHC(=NH)NH_2$ |
| $CH_2COOH$ | $CH_2CH_2COOH$ | $CH_2CONH_2$ |
| $CH_2CH_2CONH_2$ | $CH_2CH_3$ | $CH_2CH_2CH_3$ |
| $CH_2CH_2CH_2CH_3$ | $CH_2CH_2SH$ | $CH_2CH_2OH$ |
| $CH_2CH_2SCH_3$ | $(CH_2)_3NH_2$ | $(CH_2)_2CH(OH)CH_2NH_2$ |
| $(CH_2)_3NHC(=O)NH_2$ | $(CH_2)_2ONHC(=NH)NH_2$ | $CH_2C(=O)NHCH_2COOH$ |

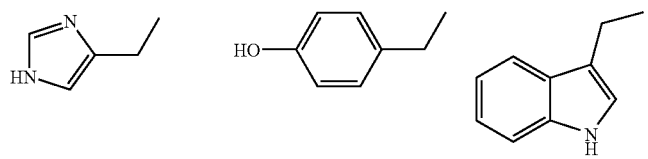

TABLE 2-continued

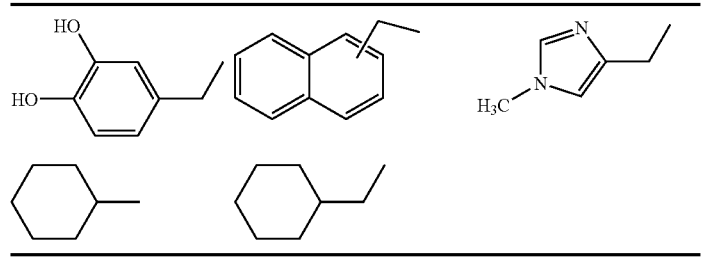

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J., et al. *Enantiomers, Racemates, and Resolutions*; Wiley: New York, 1981, each incorporated by reference herein in their entireties.

It is further recognized that functional groups present on the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., "Protective Groups in Organic Synthesis" 2d. Ed., Wiley & Sons, 1991.

Synthesis

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

As will be readily understood, functional groups present on the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., *Protective Groups in Organic Synthesis*, 2d. Ed., Wiley & Sons, 1991.

The general routes to prepare the examples shown in Table 1 of the present invention are shown in the Scheme A, Scheme B, Scheme C and Scheme D. The reagents and starting materials are commercially available, or readily synthesized by well-known techniques by one of ordinary skill in the arts. All substituents in the synthetic Schemes, unless otherwise indicated, are as previously defined.

Compounds of general structure (A) and/or (I) were prepared according to Scheme A.

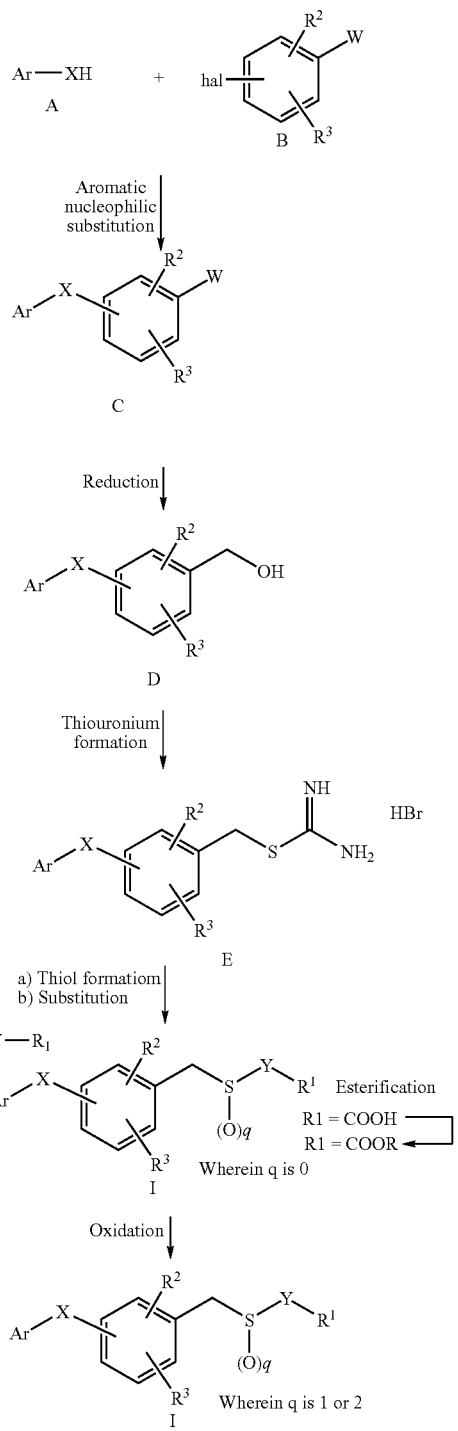

Step 1: Synthesis of Compounds of General Structure C:

An appropriate aromatic or heteroaromatic alcohol or thiol of general formula A is reacted with an appropriate halo-aryl or halo-heteroaryl aldehyde or acid of general formula B, in a polar aprotic solvent as DMF and like at reflux temperature to give the corresponding aldehyde or acid compound C wherein Ar, X, $R^2$ and $R^3$ are as defined in the final product and W represents the acid or the aldehyde group. An appropriate aromatic or heteroaromatic alcohol or thiol of general formula A is one where Ar is as defined in the final product and X represents oxygen or sulfure atoms. An appropriate halo-aryl or halo-heteroaryl aromatic aldehyde or acid of general formula B is one where $R^2$ and $R^3$ are as defined in the final product, W is an acid or an aldehyde group and hal is an halogen atom: F, Cl, Br. Upon completion, the reaction mixture is quenched by an appropriate quenching agent and the product, compound C, is isolated by conventional methods commonly employed by those skilled in the art. Compounds of general formula C may also be commercially available.

Step 2: Synthesis of Compounds of General Structure D:

The appropriate compound C of the preceding step, dissolved in a protic polar solvent as isopropanol and like, may be treated with a suitable reducing agent such as metallic hydrides. For example, the compound C may be treated with sodium borohydride (or other standard reductive conditions as LiAlH4, diisobutylaluminium hydride and like) in order to provide the corresponding alcohol of general formula D. When the starting material is a compound C bearing an acidic function (W is COOH), the reduction reaction might be performed after activation of the carboxy moiety with an activating agent as isobutylchloroformate and like, or by conventional methods commonly employed by those skilled in the art.

Step 3: Synthesis of Compounds of General Structure E:

In step 3, the alcohol moiety of compound D is converted to the corresponding thiouronium salt.

In a particular embodiment, the compound E is formed by reacting the compound D with a suitable acid. In certain aspects, the suitable acid is selected from the group consisting of hydrobromic acid, hydrochloric acid or sulfuric acid.

For example, an appropriate amount of thiourea in 48% HBr and water is warmed (preferably to 60-70° C.), followed by addition of compound D. The reaction mixture is refluxed and the stirring is continued for an additional period of time for completion of the reaction. The reaction mixture is cooled to room temperature (in some cases, an ice-bath might be needed) and the precipitated solid is optionally filtered and thoroughly washed with water to generate compound E. Sometimes there is an oil in place of the solid: in that case, the oil is thoroughly washed with water by decantation and used directly in step 4.

Step 4: Synthesis of Compounds of General Structure I Wherein q=0

The thiouronium salt of general structure E is first converted into the corresponding thiol which further undergoes a substitution reaction with an appropriate reactant of generic structure LG-Y—$R^1$ wherein Y is as defined in the final product and LG is a suitable leaving group (for example an halogen atom as Cl, Br) to generate compound I wherein q is 0.

In step 4, the wet solid (or the oil with some remaining water) from the previous step is taken into additional water and treated with an aqueous base, preferably sodium hydroxide solution. The mixture is warmed preferably to 70-80° C., but in some cases a higher temperature might be needed and to it an appropriate amount of LG-Y—$R^1$ in water (or in some cases, an alcoholic solvent) is added. The reaction mixture is refluxed for an appropriate period of time, cooled, taken into water and sometimes washed with an organic solvent (preferably ether). The basic aqueous layer is acidified with an inorganic acid solution (e.g. aqueous HCl solution). The aqueous (acidic) solution is then extracted several times into an organic solvent (e.g. ether or ethyl acetate). The combined organic layer is washed with brine, dried (MgSO$_4$ or Na$_2$SO$_4$) and concentrated to give the crude product that may be used directly in the next step. However, purification could be achieved by employing known purification techniques (e.g. recrystallization or column chromatography) to provide pure compound I wherein q is O, Ar, X, $R^1$, Y, $R^2$ and $R^3$ are as defined in the final product.

In addition, at Step 4, when the obtained compound I is an acid ($R^1$ is COOH), appropriately, it may be converted into the corresponding alkyl ester by conventional methods commonly employed by those skilled in the art.

Step 5: Synthesis of Compounds of General Structure I Wherein q is 1 or 2:

Compounds of structure I wherein q is 0 may optionally be oxidized to generate compounds of structure I wherein q is 1 or 2. Compound I wherein q is 1 is prepared under mild conditions by reacting compound I wherein q is 0 in an appropriate solvent with an appropriate oxidizing agent. An appropriate oxidizing agent is one that oxidizes the sulphide group of compound I (wherein q is 0). The corresponding product is isolated and purified by methods well known in the art.

For example, to solution of compound I (wherein q is 0) in acetic acid, an appropriate oxidizing agent (e.g. 30% wt H$_2$O$_2$, 1 equivalent) in the acetic acid is slowly added. Stirring is continued at low temperature until the disappearance of the starting material, as evidenced by various analytical techniques. The reaction mixture is concentrated. The desired product (compound I wherein q is 1) is purified, if needed, by employing known purification techniques (preferably by column chromatography and/or crystallization). In some cases, the oxidation is performed by employing 50% H$_2$O$_2$ in glacial acetic acid solvent.

Compound of formula I wherein q is 2, may be obtained from the appropriate compound of formula I wherein q is either 0 or 1 under more drastic reaction conditions such as H$_2$O$_2$ (more than 2 equivalents) in acidic medium, under heating, at temperature comprise between room temperature and the boiling temperature of the solvent, preferably between 40 and 60° C., for a time sufficient to obtain the desired product, approximately between 2 and 10 hours, preferably approximately 8 hours.

The following scheme (Scheme B) corresponds to the synthesis of compounds of general structure I wherein $R^1$ is C(=O)NR$^{12}$R$^{13}$.

Scheme B,
Synthesis of compounds of general structure I

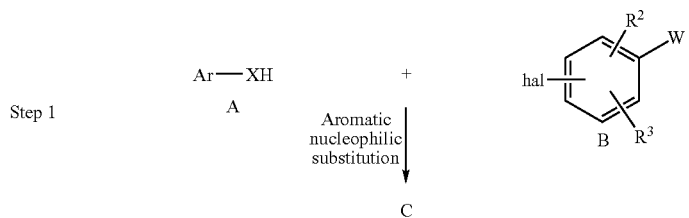

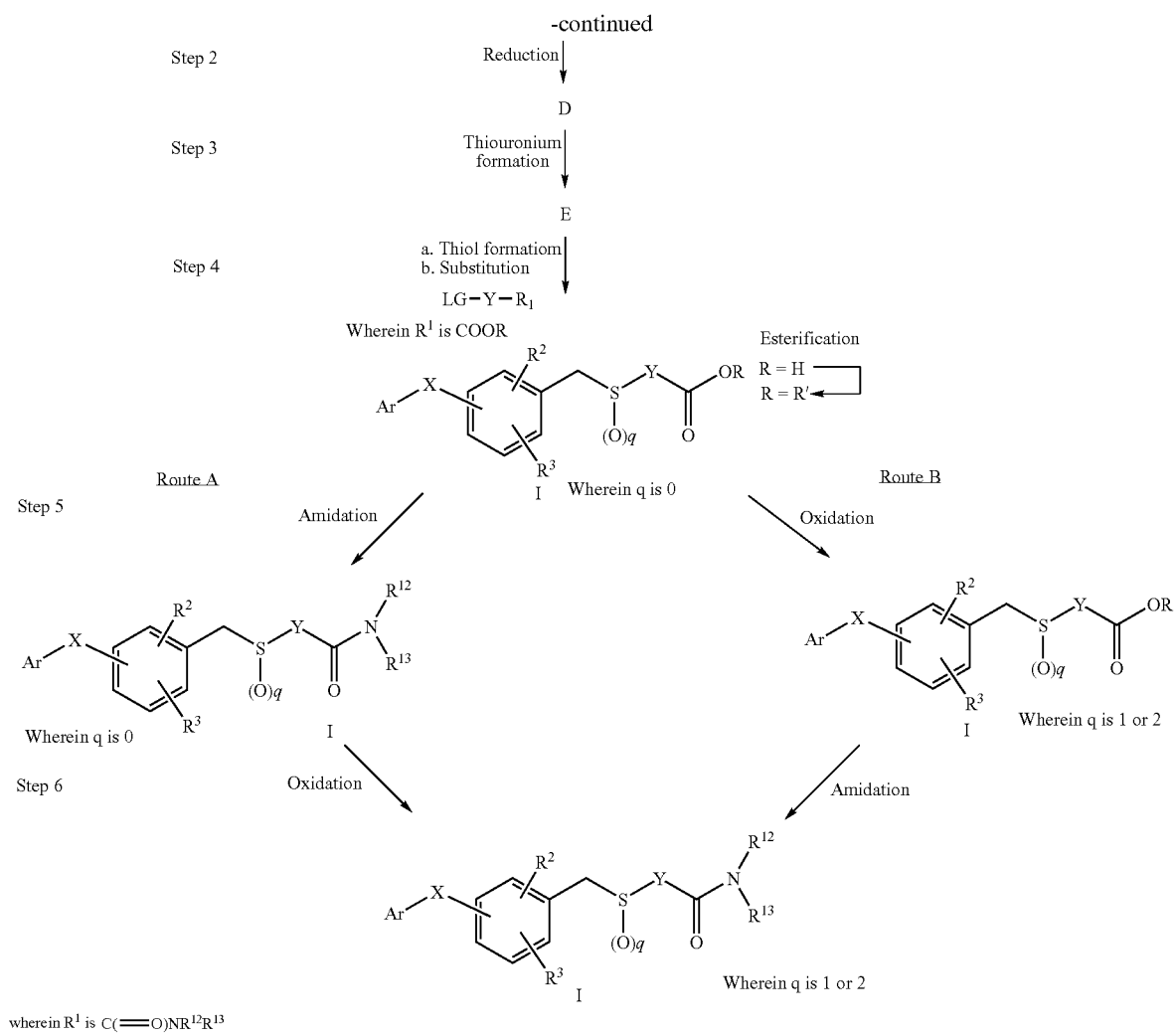

The different steps 1, 2, 3 and 4 were as described in scheme A.

In addition, at Step 4, when the obtained compound I is an acid (R is H), appropriately, it may be converted into the corresponding alkyl ester by conventional methods commonly employed by those skilled in the art.

Then, two different synthetic routes may optionally be used to generate compounds I wherein $R^1$ is C(=O)NR$^{12}$R$^{13}$.

Route A

Step 5: Synthesis of Compounds of General Formula I Wherein q is 0:

In step 5, the appropriate carboxylic acid or ester of general formula I (wherein q is 0) is reacted with an appropriate amine of general structure NHR$^{12}$R$^{13}$ and converted into the corresponding amide of general formula I wherein q is 0 and Ar, X, $R^2$, $R^3$, Y, $R^{12}$ and $R^{13}$ are as defined in the final product.

Compound I (wherein q is 0 and R1 is COOMe) may be reacted with Ammonium hydroxide (28% aqueous solution as example) or ammonia gas to give the desired compound I (wherein q is 0 and $R^{12}$ and $R^{13}$ are H). Alternatively, compound I (wherein q is 0 and R1 is COOH) may be reacted with an appropriate amine of general formula NHR$^{12}$R$^{13}$, a coupling reagent such as EDCI or DCCI, or a polymer supported coupling reagent (N-cyclohexyl carbodiimide), and optionally HOBT in an aprotic solvent as methylene chloride and like to provide amide of general formula I wherein q is 0. An appropriate amine is one which correlates to $R^{12}$ and $R^{13}$ as defined in the final product. In some cases, when the appropriate amide bears a protecting group as the tert-butyloxycarbonyl ("Boc") and like on a second nitrogen group, N-boc amine is de-protected in a subsequent step. De-protection may be performed at room temperature by acid treatment such as 4N HCl in 1,4-dioxane or trifluoroacetic acid in $CH_2Cl_2$.

Step 6: Synthesis of Compounds of General Structure I Wherein q is 1 or 2:

Compounds of structure I wherein q is 0 may optionally be oxidized to generate compounds of structure I wherein q is 1 or 2 according to the procedure described previously in Scheme A (step 5).

Route B

Route B may alternatively be used to process appropriately compound I wherein $R^1$ is C(=O)NR$^{12}$R$^{13}$.

In step 5, the process consisted, in oxidizing an appropriate compound I wherein q is 0 to generate the corresponding sufoxide or sulfone as described above in step 6, which, in turn, is reacted with an appropriate amine of general formula $NHR^{12}R^{13}$, in the next step, to give raise to the corresponding amide (compound I wherein q is 1 or 2) as described above in step 5.

Scheme C, corresponds to an alternative pathway to generate compounds of general structure I wherein X is different from O or S.

Step 1: Synthesis of Compounds of General Structure J:

An appropriate aromatic or heteroaromatic halide of general formula H substituted with a nitro group in a suitable position as defined in the final product is reacted with an appropriate thiol-substituted alkylcarboxylic acid or ester of structure $HS-Y-R^1$ (wherein $R^1$ is H or alkyl, and Y is defined as in the final compound) in an aprotic solvent such as acetone and like and in the presence of an inorganic base as

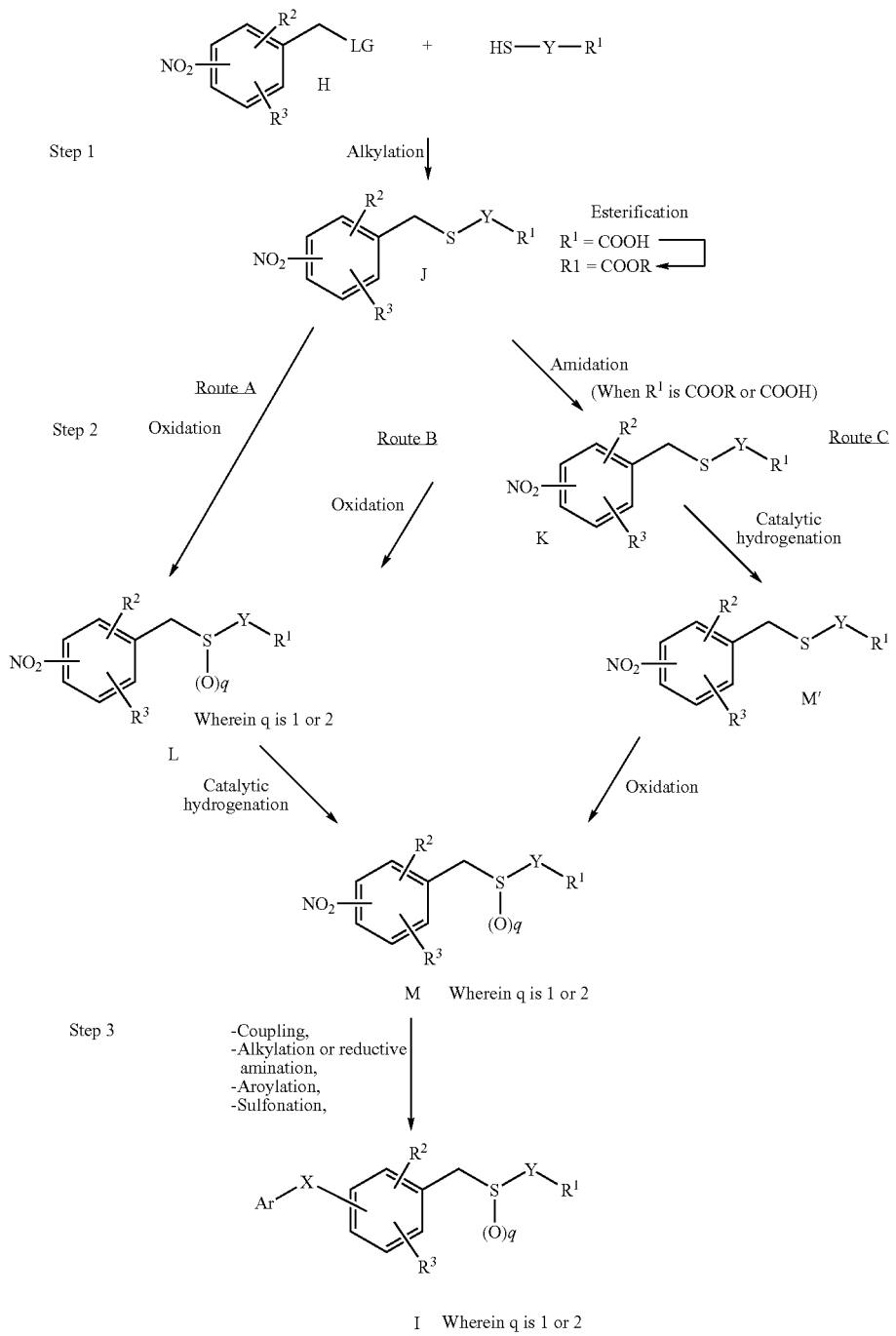

potassium carbonate and a catalyst as potassium iodine and like to generate compound J. The reaction is performed at reflux temperature.

Step 2: Synthesis of Compounds of General Structure M:
Route A
i) Oxidation Reaction: Synthesis of Compound of General Formula L Then, appropriate compounds of general formula J wherein $R^1$, $R^2$ and $R^3$ and Y are as defined in the final product are prepared by reacting compound J in an appropriate solvent with an appropriate oxidizing agent. An appropriate oxidizing agent is one that oxidizes the sulfide group of compound J. The corresponding product is isolated and purified by methods well known in the art.

For example, to solution of compound J in acetic acid, an appropriate oxidizing agent (e.g. 30% bw $H_2O_2$, 1 equivalent) in the same solvent is slowly added. Stirring is continued until the disappearance of the starting material, as evidenced by various analytical techniques. The reaction mixture is concentrated. The desired product (compound L wherein q is 1) is purified, if needed, by employing known purification techniques (preferably by column chromatography and/or crystallization). In some cases, the oxidation is performed by employing 50% $H_2O_2$ in glacial acetic acid solvent.

Compound of formula L wherein q is 2, may be obtained under more drastic reaction conditions such as $H_2O_2$ (more than 2 equivalents) in acidic medium, under heating, preferably at temperature comprise between room temperature and the boiling temperature of the solvent, preferably between 40 and 60° C., for a time sufficient to obtain the desired product, usually approximately between 2 and 10 hours, preferably approximately 8 hours.

ii) Catalytic Hydrogenation

Appropriate amino compound of general formula M may be produced by catalytic hydrogenation from the appropriate nitro compound of formula L. The hydrogenation reaction is performed under pressure in a hydrogen atmosphere and catalytic conditions using a catalyst as palladium on carbon or platinium oxide and like in an alcoholic solvent such as methanol and like.

Route B
i) Synthesis of Compound of General Formula K

Before undergoing oxidation reaction, appropriately, compound J wherein $R^1$ is a carboxylic acid may be reacted with an appropriate amine of structure $NHR^{12}R^{13}$. The amidation reaction is performed using a coupling such as EDCI or DCCI, or a polymer supported coupling reagent (N-cyclohexyl carbodiimide) and optionally HOBT in an aprotic solvent as methylene chloride and like to give the desired amide of general formula K.

Alternatively, compound J wherein $R^1$ is a carboxylic acid may be converted into the corresponding alkyl ester by conventional methods commonly employed by those skilled in the art. Then, the ester is reacted with an appropriate amine of general structure $NHR^{12}R^{13}$ in the presence of trimethyl aluminium hydride for instance or with ammonium hydroxide (28% aqueous solution as example) or ammonia gas to give the desired compound K.

ii) Oxidation and Catalytic Hydrogenation of Compound K

Compounds K wherein $R^1$ is an amide are then oxidized according to the process described above for Route A to generate the corresponding compound of formula L which, in turn, is reduced in compound M according to the process described above in Route A.

Route C

The compound of general formula K wherein $R^1$ is the appropriate amide $C(=O)NHR^{12}R^{13}$, $R^2$ and $R^3$ and Y are as defined in the final product prepared by amidation of compound J is reduced in compound M' according to the process described above in route A. Then the corresponding compound M wherein q is 1 or 2 is generated as according to the oxidation process described in Route A.

Step 3: Synthesis of Compounds of General Structure I Wherein X is NH, $C(R^{22})_2NH$, $C(=O)NH$, $S(O)_2NH$.

Compounds of general formula I, wherein Ar, X, q, $R^2$, $R^3$, Y and $R^1$ are as defined in the final product may be prepared in a one step procedure in suitable experimental conditions as to obtain the target X definition.

For exemple, compound of formula I wherein X is NH may be obtained by coupling an appropriate amine M with an appropriate boronic acid in an aprotic solvent as dichloromethane and the like. The reaction is carried out in the presence of a base such as 2,6-lutidine and like as pyridine, triethylamine, diisopropylethylamine and in catalytic conditions using copper(II) acetate. An appropriate boronic acid is one which correlates to Ar as defined in the final product.

Compounds of general formula I, wherein X is $C(R^{22})_2$ NH may be prepared in a one step procedure by alkylation an appropriate amine M with a suitable alkylating agent in an aprotic solvent as DMF, dichloromethane and the like. A suitable alkylating agent is one which correlates to Ar and $R^{22}$ as defined in the final product.

Compounds of formula I wherein X is an amide may be obtained by aroylation of an appropriate amine M with an appropriate aromatic or heteroaromatic halide in an aprotic solvent as dichloromethane and the like. The reaction is carried out in the presence of a base such as pyridine, and the like triethylamine, diisopropylethylamine. An appropriate aromatic or heteroaromatic halide is one which correlates to Ar as defined in the final product.

Compounds of general formula I, wherein X is $S(O)_2NH$ may be prepared in a one step procedure by sulfonation of an appropriate amine M with an appropriate aromatic or heteroaromatic sulfonyl chloride in an aprotic solvent. The reaction is carried out in the presence of a base such as pyridine, and like triethylamine, diisopropylethylamine. An appropriate aromatic or heteroaromatic sulfonyl chloride is one which correlates to Ar as defined in the final product.

Compounds of general structure I were also generated according to Scheme D.

Scheme D,
Synthesis of compounds of general structure I

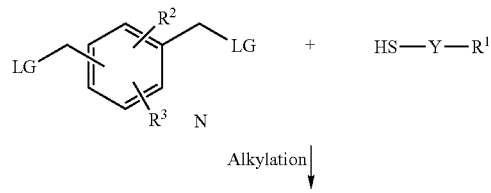

Step 1  Alkylation

-continued

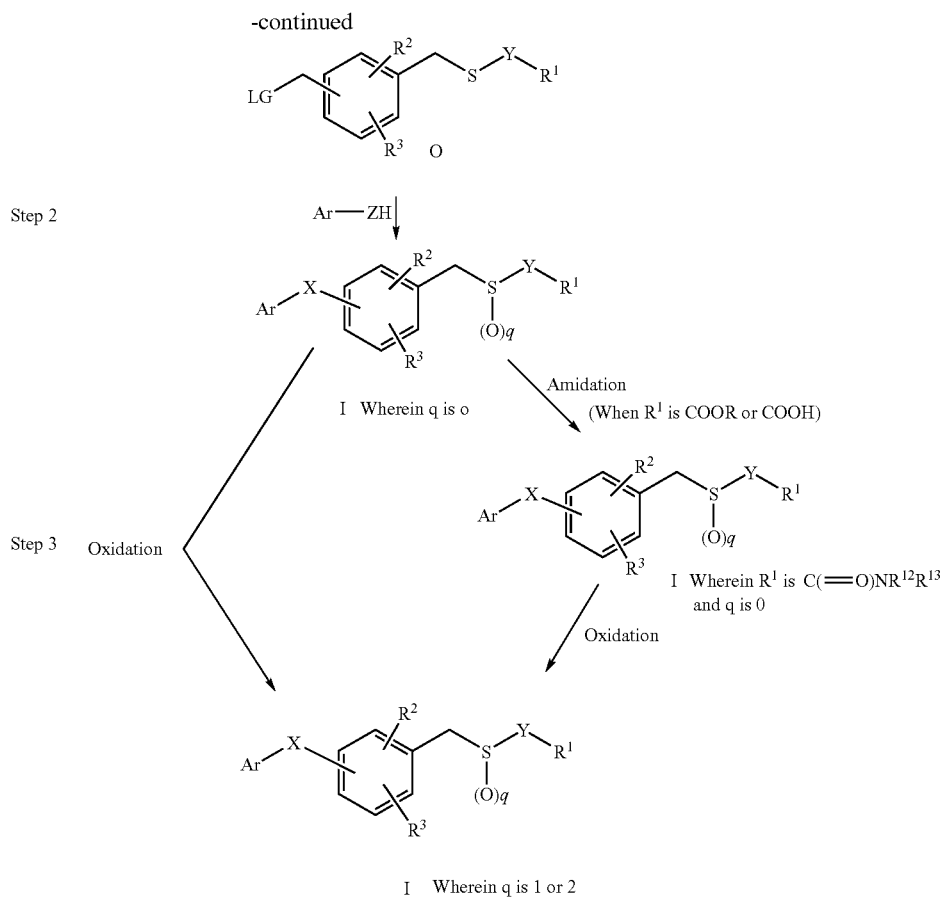

Scheme D, Synthesis of Compounds of General Structure I

Step 1: Synthesis of Compounds of General Structure O

An appropriate xylene of general formula N bearing two leaving groups in a suitable position as defined in the final product is reacted with appropriate thiol of structure HS—Y—R$^1$ wherein Y and R1 are as defined in the final product to generate compound of general formula O. The reaction is carried out in an aprotic solvent such as DMF and like and in the presence of an inorganic base as potassium carbonate and at room temperature in an argon atmosphere.

Step 2: Synthesis of Compounds of General Structure I wherein q is 0:

Then compound O is reacted with an appropriate aryl or heteroaryl alcohol, amine or thiol to generate compound of general formula I wherein q is 1 and Ar, X, R$^1$, R$^2$ and R$^3$ are as defined in the final product.

In addition, when R$^1$ is an ester function, compound I may be hydrolysed at solvent reflux temperature and in the presence of an inorganic base before the amidification step.

Step one and step 2 may be processed without isolation of the intermediate O (one pot procedure).

Step 3: Synthesis of Compounds of General Structure I wherein q is 1 or 2 i) Oxidation Reaction

Then, appropriate compounds of general formula I wherein R$^1$, R$^2$, R$^3$, X, q and Y are as defined in the final product are prepared by reacting compound I in an appropriate solvent with an appropriate oxidizing agent. An appropriate oxidizing agent is one that oxidizes the sulfide group of compound I. The corresponding product is isolated and purified by methods well known in the art.

For example, to solution of compound I in acetic acid, an appropriate oxidizing agent (e.g. 30% wt H$_2$O$_2$, 1 equivalent) in the same solvent is slowly added. Stirring is continued until the disappearance of the starting material, as evidenced by various analytical techniques. The reaction mixture is concentrated. The desired product (compound I wherein q is 1) is purified, if needed, by employing known purification techniques (preferably by column chromatography and/or crystallization). In some cases, the oxidation is performed by employing 50% H$_2$O$_2$ in glacial acetic acid solvent.

Compound of formula I wherein q is 2, may be obtained under more drastic reaction conditions such as H$_2$O$_2$ (more than 2 equivalents) in acidic medium, under heating, preferably at temperature comprise between room temperature and the boiling temperature of the solvent, preferably between 40 and 60° C., for a time sufficient to obtain the desired product, usually approximately between 2 and 10 hours, preferably approximately 8 hours.

ii) Synthesis of Compound of General Formula I Wherein R$^1$ is C(=O)NHR$^{12}$R$^{13}$ Before undergoing oxidation reaction, appropriately, compound I wherein q is 0 and R$^1$ is an ester or an acid function may be reacted with an appropriate amine of structure NHR$^{12}$R$^{13}$. as already described in schema B, route A.

Compounds I wherein $R^1$ is an amide are then oxidized according to the processes described above to generate the corresponding compound of formula I wherein q is 1 or 2.

EXAMPLES

Other features of the invention will become apparent in the course of the following descriptions of exemplary embodiments. These examples are given for illustration of the invention and are not intended to be limiting thereof.

I-Compounds Prepared According to Schemes A and B.

The following Examples 1 to 112 were synthesized according to Schemes A and B.

A-Preparation of Compounds C

Compound 1

Compound C wherein Ar is 3,4-DiClPhenyl, X is O, Substitution in para Position, W is C(=O)H.

To a stirred solution of A (aldehyde wherein Ar is 3,4-DiClPhenyl, X is O, 39 g, 239 mmol) in DMF (200 mL), parafluorobenzaldehyde (compound B; 26 mL; 242 mmol) and cesium carbonate (80 g; 250 mmol) were added. The mixture was refluxed for 3 hours and then cooled to room temperature. After dilution with brine (800 mL), the resulting precipitate was extracted with $Et_2O$ (4×250 mL). The organic layer was washed with brine (3×300 mL), water (2×300 mL), and then dried over $MgSO_4$ and concentrated in vacuo. Trituration of the resulting residue with cold $Et_2O$, filtration and drying under vacuum gave 42 g (157 mmol) of compound 1 as an off-white solid.

Yield=66%.

$R_f$=0.94 (95:5 methylenechloride/methanol).

According to the procedure as described for compound 1, the following compounds were prepared.

Compound 2

Compound C wherein Ar is 3,4-DiClPhenyl, X is O, Substitution in ortho Position, W is C(=O)H.

Reagents: compound A (wherein Ar is 3,4-DiClPhenyl, X is O, 39 g, 239 mmol) and orthofluorobenzaldehyde (compound B; 26 mL; 242 mmol).

Yield=35% (22.3 g; 83 mmol of compound 2).

$R_f$=0.73 (eluent: 8:2 cyclohexane/ethylacetate).

Compound 3

Compound C wherein Ar is 4-ClPhenyl, X is S, Substitution in para Position, W is C(=O)H.

Reagents: compound A (wherein Ar is 4-ClPhenyl, X is S, 26.3 g, 182 mmol) and parafluorobenzaldehyde (compound B; 20 mL; 242 mmol).

Yield=88% (40 g; 160 mmol of compound 3 as a yellow powder).

$R_f$=0.57 (eluent: 8:2 cyclohexane/ethylacetate).

Compound 4

Compound C wherein Ar is 4-ClPhenyl, $R^2$ is 3-Cl, X is O, Substitution in para Position, W is C(=O)H.

To a stirred solution of A (wherein Ar is 4-ClPhenyl, X is O, 23.4 g, 182 mmol) in DMF (150 mL), 2-chloro-4-fluorobenzaldehyde (compound B; 28.8 g; 182 mmol) and cesium carbonate (61 g; 187 mmol) were added. The mixture was refluxed for 4 hours and then cooled to room temperature. After dilution with brine (800 mL), the resulting precipitate was extracted with $Et_2O$ (4×250 mL). The organic layer was washed with brine (3×300 mL), water (2×300 mL), and then dried over $MgSO_4$ and concentrated in vacuo. The crude product was purified by flash chromatography (eluent:cyclohexane/ethylacetate 9/1) to afford compound 4 (20.5 g; 77 mmol)

Yield=42%.

$R_f$=0.75 (9:1 cyclohexane /ethylacetate).

Compound 4a

Compound C wherein Ar is 4-ClPhenyl, X is O, $R^2$ is 4'—Cl, $R^3$ is H, Substitution in ortho Position, W is C(=O)H.

To a stirred solution of 4-chlorophenol (compound A wherein Ar is 4-ClPhenyl, X is O, 20.3 g, 155 mmol) in DMF (150 mL), 4-chloro-2-fluorobenzaldehyde (compound B; 25 g; 158 mmol) and potassium carbonate (30 g; 217 mmol) were added. The mixture was stirred for 15 hours. After dilution with brine (300 mL), the resulting precipitate was extracted with $Et_2O$ (4×250 mL). The organic layer was washed with brine (3×300 mL), water (2×300 mL), and then dried over $MgSO_4$ and concentrated in vacuo to give compound 4a as an oil.

Yield=100% (41.4 g; 155 mmol)

$R_f$=0.61 (8:2 cyclohexane/ethylacetate).

B-Preparation of Compounds D

Compound 5

Compound D wherein Ar is 3,4-DiClPhenyl, X is O, Substitution in ortho Position.

To a stirred solution of compound 2 (22.3 g, 83 mmol) in isopropanol (120 mL), sodium borohydride (3.16 g; 83 mmol) was added. The mixture was stirred at room temperature for one hour, before adding water (350 mL). After stirring for additional 3 hours, the aqueous layer was extracted with $Et_2O$ (2×300 mL). The combined organic layer was washed with water (3×300 mL), dried over $MgSO_4$ and concentrated in vacuo to give compound 5 as an orange oil.

Yield=95% (21.3 g; 79 mmol).

$R_f$=0.35 (eluent:methylenechloride).

The following compound were prepared according to the procedure described for compound 5:

Compound 6

Compound D wherein Ar is 3,4-DiClPhenyl, X is O, Substitution in para Position.

Reagents: compound 1 (38 g; 142 mmol) and sodium borohydride (5.37 g; 142 mmol).

Yield=43% (16.6 g; 62 mmol).

$R_f$=0.56 (eluent: 95:5 methylenechloride/methanol).

Compound 7

Compound D wherein Ar is 4-ClPhenyl, X is S, substitution in para position;

Reagents: compound 3 (40 g; 161 mmol) and sodium borohydride (6.09 g; 161 mmol). Compound 7 was generated as a yellow powder.

Yield=99% (40 g; 160 mmol).

$R_f$=0.21 (eluent: methylenechloride).

Compound 8

Compound D wherein Ar is Phenyl, X is O, Substitution in ortho Position.

To an ice cold solution of compound C (wherein Ar is Phenyl, X is O, substitution in ortho position, W is C(=O)OH; 25 g; 117 mmol) and N-methylmorpholine (20 ml; 180 mmol) in THF (100 mL) under $N_2$, isobutylchloroformate (17 ml; 131 mmol) was added. After stirring for 15 minutes, sodium borohydride (12.5 g; 330 mmol) was added, followed by 50 mL of water. The ice bath was removed and stirring was continued overnight. After cooling, the mixture was made acidic with hydrochloric acid and extracted with Et$_2$O (2×200 mL). The combined organic layer was washed with water (2×200 mL), dried (MgSO$_4$) and evaporated to dryness. The crude product was purified by flash column chromatography (eluent:ethyl acetate/cyclohexane (1/9) to produce compound 8 as an colorless oil.

Yield=70% (16.4 g; 82 mmol).

R$_f$=0.50 (eluent: 7:3 cyclohexane/ethylacetate).

The following compound was prepared according to the procedure as described for compound 8:

Compound 9

Compound D wherein Ar is Phenyl, X is O, Substitution in para Position.

Reagents: compound C (wherein Ar is Phenyl, X is O, substitution in para position, W is C(=O)OH; 38 g; 142 mmol), isobutylchloroformate (13.6 mL; 105 mmol) and sodium borohydride (10 g; 264 mmol).

Yield=46% (8.6 g; 43 mmol).

R$_f$=0.58 (eluent: 1:1 ethylacetate/cyclohexane).

Compound 10

Compound D (wherein Ar is 4-ClPhenyl, R$^2$ is 3-Cl, X is O, Substitution in para Position)

To a stirred solution of compound 4 (20.5 g, 77 mmol) in isopropanol (100 mL), sodium borohydride (2.9 g; 77 mmol) was added. The mixture was stirred at room temperature for one night, before adding water (350 mL). After stirring for additional 3 hours, the solvent was removed by decantation. The resulting residue was taken into a mixture of water (400 mL) and ether (400 mL). The organic layer was washed with water (2×150 mL), dried over MgSO$_4$ and concentrated in vacuo to furnish an oil that was purified by column chromatography (eluent methyleneckloride) to afford compound 10 as a yellow oil after solvent evaporation.

Yield=30% (6.3 g; 23 mmol).

R$_f$=0.45 (eluent:methylenechloride).

Compound 10a

Compound D wherein Ar is 4-ClPhenyl, X is O, R$^2$ is 4'-Cl, R$^3$ is H, Substitution in ortho Position.

To a stirred solution of compound 4a (41.4 g, 155 mmol) in isopropanol (250 mL), sodium borohydride (6.8 g; 180 mmol) was added. The mixture was stirred at room temperature for one night, before adding water (1.5 L). After stirring for additional 3 hours, the resulting precipitated solid was filtered off, washed with water and dried in vacuo to generate compound 10a as a white powder.

Yield=63% (26.2 g; 97 mmol).

R$_f$=0.61 (eluent: 98:2 methylenechloride/methanol).

C-Preparation of Compounds E

Compound 11

Compound E wherein Ar is 4-ClPhenyl, X is O, Substitution in para Position.

To a stirred mixture of thiourea (6 g; 79 mmol), 48% HBr (34 mL) and water (6 mL) at 60° C., compound D (Ar is 4-ClPhenyl, X is O, substitution in para position; 14.6 g; 62 mmol) prepared according to scheme A, step 1 and 2, was added portionwise. The reaction mixture was refluxed for one hour, cooled and filtered. The resulting residue was washed with water (3×30 mL) and dried under vacuum to generate 21 g of compound 11 as the major product. It was used in the next step without any further purification.

D-Preparation of Compounds I-Scheme A

Example 1

Compound I wherein Ar is 3,4-DiClPhenyl, X is O, q is 0, Substitution in para Position, Y—R$^1$ is CH$_2$ COOH.

To a stirred mixture of thiourea (6 g; 79 mmol), 48% HBr (34 mL) and water (6 mL) at 60° C., compound 6 (16.6 g; 62 mmol) was added fractionwise. The reaction mixture was refluxed for one hour, and then cooled to room temperature and filtered. The resulting residue was washed with water (3×30 mL) and then poured into aqueous NaOH (32%, 30 mL). The resulting aqueous mixture was stirred and heated to 70° C. before adding dropwise a solution of chloracetic acid (6.8 g, 72 mmol) in aqueous sodium hydrogenocarbonate (16 mL). The mixture was then refluxed for one hour, cooled to room temperature, diluted with water (150 mL), acidified to pH 2 with 4N aqueous HCl and then extracted into Et$_2$O (250 mL). The dried (MgSO4) organic phase was evaporated to dryness to give a residue. The crude product was purified by flash chromatography (eluent: methylenechloride/methanol (9/1) to afford Example 1 (13.2 g; 38.5 mmol) as an orange oil.

Yield=62%.

R$_f$=0.47 (eluent: 9:1 methylenechloride/methanol).

According to the process as described above, the following compounds were prepared:

Example 2

Compound I wherein Ar is 3,4-DiClPhenyl, X is O, q is 0, Substitution in ortho Position; Y—R$^1$ is CH$_2$ COOH.

Reagents: compound 5 (21.3 g; 79 mmol) following the same procedure and chloracetic acid (6.8 g, 72 mmol).

Yield=49% (16.8 g; 49 mmol).

R$_f$=0.53 (eluent: 9:1 methylenechloride/methanol).

Example 3

Compound I wherein Ar is 4-ClPhenyl, X is S, q is 0, Substitution in para Position, Y—R$^1$ is CH$_2$ COOH.

Reagents: compound 7 (15.6 g, 62 mmol) and chloracetic acid (4.16 g, 44 mmol).

Yield=82% (16.5 g; 51 mmol of compound 12 obtained as an off-white solid)

R$_f$=0.44 (eluent: 90:10 methylenechloride/methanol).

Example 4

Compound I wherein Ar is Phenyl, X is O, q is 0, Substitution in para Position, Y—R$^1$=CH$_2$ COOH.

Reagents: compound 9 (8 g, 40 mmol) and chloracetic acid (4.16 g, 44 mmol).

Yield=90% (9.9 g; 36 mmol).

R$_f$=0.42 (eluent: 90:10 methylenechloride/methanol).

Example 5

Compound I wherein Ar is Phenyl, X is O, q is 0, Substitution in ortho Position, Y—R$^1$ is CH$_2$ COOH.

Reagents: compound 8 (8 g, 40 mmol) and chloracetic acid (4.16 g, 44 mmol).

Yield=64% (8.4 g; 31 mmol).

$R_f$=0.49 (eluent: 90:10 methylenechloride/methanol).

Example 6

Compound I wherein Ar is 4-ClPhenyl, $R^2$ is 3-Cl, X is O, q is 0, Substitution in para Position, Y—$R^1$=$CH_2COOH$.

To a stirred mixture of thiourea (2.2 g; 29 mmol), 48% HBr (12 mL) and water (2 mL) at 60° C., compound 10 (6.3 g; 23.4 mmol) was added fractionwise. The reaction mixture was refluxed for fifteen minutes, and then cooled to room temperature and filtered. The resulting residue was washed with water (3×30 mL) and then poured into aqueous NaOH (32%, 12 mL). The resulting aqueous mixture was stirred and heated to 70° C. before adding dropwise a solution of sodium chloracetate (3 g, 26 mmol). The mixture was then refluxed for one hour, cooled to room temperature, diluted with water (150 mL), acidified to pH 2 with 4N aqueous HCl and then extracted into $Et_2O$ (250 mL). The dried (MgSO4) organic phase was evaporated to dryness to afford Example 6 (13.2 g; 38.5 mmol) as an yellow oil after solvent evaporation.

Yield=69% (6.9 g; 20 mmol)

$R_f$=0.36 (eluent: 93:7 methylenechloride/methanol).

Example 7

Compound I wherein Ar is 4-ClPhenyl, X is O, q is 0, Substitution in para Position, Y—$R^1$ is $CH_3$.

To a stirred mixture of compound 11 (7.3 g; 19.5 mmol) in 0.6N aqueous sodium hydroxyde (20 mL), dimethylsulfate (2 mL, 18 mmol) was added. The reaction mixture was then refluxed for two hours, cooled and acidified with 1N aqueous hydrochloride. The precipitate was extracted with a mixture of ether (50 mL) and ethylacetate (50 mL). The organic layer was washed with water (2×100 mL) and concentrated under vacuum. The resulting residue was purified by column chromatography (eluent:methylene chloride) to produce 2.2 g of Example 7 as the major product (oil). It was used in the next step without any further purification.

Example 8

1-Methanesulfinylmethyl-4-(4-chlorophenoxy)-benzene

Compound I wherein Ar is 4-ClPhenyl, X is O, q is 1, substitution in para position, Y—$R^1$ is $CH_3$.

To a solution of Example 7 (2.2 g; 8.3 mmol) in acetic acid (30 mL), a 30% by wt hydrogen peroxide solution (0.99 mL; 9.7 mmol) was added. The mixture was stirred until no more starting material was detected (HPLC), concentrated under high vacuum. The resulting residue was purified by column chromatography (eluent:methylene chloride/methanol 95/5) to produce an oil which is taken up into methylene chloride (100 mL). The organic phase was washed with an aqueous solutiuon of sodium hydroxide (2×50 mL), water (1×50 mL), dried ($MgSO_4$) and concentrated in vacuo to produce Example 8 as a white powder.

Yield=39% (0.9 g; 3.2 mmol)

$^1$H-NMR (DMSO-$d_6$) δ: 7.45 (d, 2H), 7.3 (d, 2H), 7.0 (m, 4H), 4.2 (d, 1H), 3.9 (d, 1H), 2.45 (s, 3H).

MS: 303 (M+Na).

Example 9 di[4-(4-Chloro-phenoxy)-phenylmethyl]sulfoxyde

Compound I Wherein Ar is 4-ClPhenyl, X is O, q is 1, Substitution in Para Position, Y—$R^1$ is $CH_2$[4(4-ClPhenoxy)phenyl].

0.6 g of Example 9 was obtained as a by product during the preparation process of example 8 as white powder.

$^1$H-NMR (DMSO-$d_6$) δ: 7.45 (d, 2H), 7.3 (d, 2H), 7.0 (m, 4H), 4.2 (d, 1H), 3.8 (d, 1H).

MS 483 (M+H).

Example 10

1-Methanesulfinylmethyl-4-(3,4-dichlorophenoxy)-benzene

Compound I Wherein Ar is 3,4-DiClPhenyl, X is O, q is 1, Substitution in Para Position, Y—$R^1$ is $CH_3$ was prepared following the same multistep general method as described in scheme A for Example 8 utilizing the appropriate substituted aryl alcohol.

MS: 337 (M+Na).

Example 10a

Compound I Wherein Ar is 4-ClPhenyl, X is O, $R^2$ is 4'-Cl, $R^3$ is H, q is 0, Substitution in Ortho Position, Y—$R^1$ is $CH_2$COOH.

To a stirred mixture of thiourea (6 g; 79 mmol), 48% HBr (34 mL) and water (6 mL) at 60° C., compound 10a (17.4 g; 65 mmol) was added portionwise. The reaction mixture was refluxed for one hour, cooled and filtered. The resulting residue was washed with water (3×30 mL) and then poured into aqueous NaOH (32%, 30 mL). The resulting aqueous mixture was stirred and heated to 70° C. before adding dropwise a solution of sodium chloracetate (8.4 g, 72 mmol) in water (16 mL). The mixture was then refluxed for one hour, cooled to room temperature, diluted with water (150 mL), acidified to pH 2 with 4N aqueous HCl and then extracted into $Et_2O$ (250 mL). The dried (MgSO4) organic phase was evaporated to dryness to give a residue. The crude product was purified by flash chromatography (eluent: methylenechloride/methanol (9/1) to afford Example 10a as an orange powder.

Yield=57% (12.6 g; 37 mmol).

$^1$H-NMR (DMSO-$d_6$) δ: 7.0 (m, 3H), 6.75 (broad d, 1H), 6.65 (broad d, 2H), 6.5 (broad s, 1H), 3.4 (s, 2H), 2.8 (s, 1H).

MS: 341 (M−1).

E-Synthesis of Compound I (q is 0)-Scheme B, Route A

Example 11

Compound I Wherein Ar is 3,4-DiClPhenyl, X is O, q is 0, Substitution in Para Position, Y—$R^1$ is $CH_2$CO-1-(4-acetyl)-piperazinyl.

To a cooled solution of Example 1 (2.27 g; 6.6 mmol) in $CH_2Cl_2$ (50 mL), N-acetylpiperazine (0.94 g; 7.3 mmol) and EDCI (1.4 g; 7.3 mmol) were added. The reaction mixture was stirred until no more starting material was detected. The organic layer was washed with 1N HCN, water, dried ($MgSO_4$) and concentrated in vacuo. The crude product was purified by column chromatography (eluent:methylenechloride/methanol 98.5/1.5) to produce Example 11 as an oil.

Yield=76% (2.3 g; 5 mmol)

$R_f$=0.26 (eluent: 96:4 methylenechloride/methanol)

The following examples were prepared according to the process as described for example 11:

Example 12

Compound I Wherein Ar is Phenyl, X is O, q is 0, Substitution in Ortho Position, Y—$R^1$ is $CH_2$ CO NH$(CH_2)_2$OH.

Reagents: Example 5 (0.7 g, 2.6 mmol) and ethanolamine (0.18 g; 2.9 mmol).

Yield=56% (0.46 g; 1.4 mmol)

$R_f$=0.5 (eluent: 90:10 methylenechloride/methanol)

Example 13

Compound I Wherein Ar is 3,4-DiClPhenyl, X is O, q is 0, Substitution in Para Position, Y—$R^1$ is $CH_2$ CO-1-(4-Boc)-piperazinyl.

To a cooled solution of example 1 (8.8 g; 25.6 mmol) in $CH_2Cl_2$ (150 mL) N-Bocpiperazine (4.8 g; 25.8 mmol), EDCI (4.9 g; 25.6 mmol) and HOBT (3.5 g; 26 mmol) were added. The reaction mixture was stirred until no more starting material was detected. The organic layer was washed with 1N HCl (2×100 mL), water (100 mL), dried ($MgSO_4$) and concentrated in vacuo. Trituration of the resulting residue with cold $Et_2O$, filtration and drying under vacuum gave Example 13 as a white solid.

Yield=70% (9 g; 18 mmol)

$R_f$=0.13 (eluent: 99:1 methylenechloride/methanol)

Example 14

Compound I Wherein Ar is 3,4-DiClPhenyl, X is O, q is 0, Substitution in Para Position, Y—$R^1$ is $CH_2$ CO-N-piperazinyl.

To a solution of Example 13 (2 g; 3.9 mmol) in 1,4-dioxane (20 mL), hydrogenchloride in 1,4-dioxane (4N solution; 20 mL) was added. The reaction mixture was stirred for one hour at room temperature, then ether (200 mL) was added. Filtration and drying under vacuum gave a powder which is dissolved in water (100 mL). The aqueous layer was basified with NaOH (1N) and the resulting precipitate was extracted with ether (150 mL). The dried ($MgSO_4$) organic layer was evaporated to dryness to furnish Example 14 as an oil.

Yield=87% (1.4 g; 3.4 mmol)

$^1$H-NMR (DMSO-$d_6$) δ:9.5 (s, 2H), 7.7 (d, 1H), 7.4 (d, 1H), 7.3 (d, 1H), 7.05 (d, 1H), 6.95 (dd, 1H), 3.75 (s, 2H), 3.7 (broad, 4H), 3.4 (s, 2H), 3.15 (broad, 2H), 3.0 (broad, 2H)

Example 15

Compound I Wherein Ar is 3,4-DiClPhenyl, X is O, q is 0, Substitution in ortho Position, Y—$R^1$ is $CH_2$ $CONH_2$.

To a cold solution of Example 2 (3 g, 8.7 mmol) in methanol (50 mL), thionylchloride (4.2 ml; 57 mmol) was added dropwise. After 1 hour stirring at room temperature, the solvent was removed in vacuo. The oily residue was taken by mixture of MeOH (50 mL) and 28% $NH_4OH$ (50 mL) and the reaction mixture stirred overnight. The methanol was evaporated and water (200 mL) added. The precipitated solid was filtered, washed with water (4×50 mL) and dried in vacuo to generate Example 15 as an off-white solid.

Yield=77% (2.3 g; 6.7 mmol).

$R_f$=0.38 (eluent: 95:5 methylenechloride/methanol).

Example 16

Compound I Wherein Ar is 4-ClPhenyl, X is S, q is 0, Substitution in Para Position, Y—$R^1$ is $CH_2$ CO-1-(4-acetyl)-piperazinyl.

To a cooled solution of Example 3 (2.14 g; 6.6 mmol) in $CH_2Cl_2$ (50 mL), N-acetylpiperazine (0.9 g; 7 mmol), EDCI (1.4 g; 7.3 mmol) and HOBT (1 g; 7.4 mmol) were added. The reaction mixture was stirred until no more starting material was detected. The organic layer was washed with 1N HCl (2×100 mL), water (100 mL), dried ($MgSO_4$) and concentrated in vacuo. Trituration of the resulting residue with $Et_2O$, filtration and drying under vacuum gave Example 16 as a white powder.

Yield=74% (2.15 g; 4.9 mmol)

$R_f$=0.27 (eluent: 95:5 methylenechloride/methanol).

Example 17

Compound I Wherein Ar is 4-ClPhenyl, $R^2$ is 3-Cl, X is O, q is 0, Substitution in Para Position, Y—$R^1$ is $CH_2$CO-1-(4-acetyl)-piperazinyl.

To a cooled solution of Example 6 (3.18 g; 9.3 mmol) in $CH_2Cl_2$ (60 mL), N-acetylpiperazine (1.33 g; 10.4 mmol), EDCI (2 g; 10.4 mmol) and HOBT (1.41 g; 10.4 mmol) were added. The reaction mixture was stirred until no more starting material was detected. The organic layer was washed with 1N HCl, water, dried ($MgSO_4$) and concentrated in vacuo. The crude product was purified by column chromatography (eluent: methylenechloride/methanol 98/2) to produce Example 17 as an oil.

Yield=75% (1.6 g; 3.5 mmol)

$R_f$=0.33 (eluent: 95:5 methylenechloride/methanol)

Example 18

Compound I Wherein Ar is 4-ClPhenyl, $R^2$ is 3-Cl, X is O, q is 0, Substitution in Para Position, Y—$R^1$ is $CH_2CONH2$.

To a cooled solution of Example 6 (3.6 g; 10.5 mmol) in methanol (100 mL), thionylchloride (2.2 ml; 30 mmol) was added dropwise. After 1 hour stirring at room temperature, the solvent was removed in vacuo. The oily residue was taken by mixture of MeOH (75 mL) and 28% $NH_4OH$ (75 mL) and the reaction mixture stirred overnight. The methanol was evaporated and water (200 mL) added. The precipitated solid was filtered, washed with water (2×50 mL) and purified by column chromatography (eluent: methylenechloride/methanol 98/2) to produce Example 18 as a white solid.

Yield=58% (2.07 g; 6.0 mmol).

$R_f$=0.52 (eluent: 95:5 methylenechloride/methanol).

Example 18a

Compound I Wherein Ar is 4-ClPhenyl, X is O, $R^2$ is 4'-Cl, $R^3$ is H, q is 0, Substitution in Ortho Position, Y—$R^1$ is $CH_2$ $CONH_2$.

To a cold solution of Example 10a (6.3 g, 18.3 mmol) in methanol (100 mL), thionylchloride (3.8 ml; 52 mmol) was added dropwise. After 1 hour stirring at room temperature, the solvent was removed in vacuo. The oily residue was taken by mixture of MeOH (100 mL) and 28% $NH_4OH$ (100 mL) and the reaction mixture stirred overnight. The methanol was evaporated and the residue was purified by flash chromatography (eluent: methylenechloride/methanol (95/5) to afford Example 18a as a white powder.

Yield=56% (3.5 g; 10.2 mmol).

$R_f$=0.44 (eluent: 95:5 methylenechloride/methanol).

F-Preparation of Compound I (q is 1 or 2)—Scheme B, Route A

Example 19

2-[4-(3,4-dichloro-phenoxy)-phenylmethanesulfinyl]-1-piperazin-1-yl-ethanone

Compound I Wherein Ar is 3,4-DiClPhenyl, X is O, q is 1, Substitution in Para Position, Y—$R^1$ is $CH_2$CO-N-piperazinyl.

To a solution of Example 14 (1.4 g; 3.4 mmol) in acetic acid (10 mL), a 30% by wt hydrogen peroxide solution (0.4 mL; 4 mmol) was added. The mixture was stirred until no more starting material was detected (HPLC), concentrated under high vacuum. Then water (100 mL) was added to the residue. The aqueous solution was basified with NaOH (1N) and the precipitate extracted with ethyl acetate (150 mL). The organic phase was dried over MgSO4 and evaporated to dryness to give an oil. Ethanol (30 mL) was added and the solution stirred before adding fumaric acid (0.11 g; 0.95 mmol). The reaction mixture was stirred overnight and filtered. The resulting solid was dried under vacuum to give Example 19.

Yield=38% (0.63 g; 1.3 mmol).

$^1$H-NMR (DMSO-$d_6$) δ: 7.7 (d, 1H), 7.4 (d, 2H), 7.3 (d, 1H), 7.2 (d, 2H), 7.1 (dd, 1H), 6.5 (s, 1H), 4.25 (d, 1H), 4.05 (d, 1H), 3.9 (m, 2H), 3.5 (broad, 4H), 2.9 (broad, 4H).

MS: 427 (M+H)

According to the oxidation procedure as described for example 19, the following compounds were prepared:

Example 20

2-[4-(3,4-dichloro-phenoxy)-phenylmethanesulfinyl]-acetamide

Compound I Wherein Ar is 3,4-DiClPhenyl, X is O, q is 1, Substitution in Ortho Position, Y—$R^1$ is $CH_2CONH_2$.

Reagent: Example 15 (2.3 g; 6.7 mmol) and a 30% by wt hydrogen peroxide (0.7 mL; 6.9 mmol).

Yield=79% (1.9 g; 5.3 mmol).

$^1$H-NMR (DMSO-$d_6$) δ: 7.7 (broad s, 1H), 7.65 (d, 1H), 7.5 (broad d, 1H), 7.40 (broad t, 1H), 7.35 (broad s, 1H), 7.25 (broad s, 1H), 7.20 (t, 1H), 7.0 (broad, 2H), 4.30 (d, 1H), 4.05 (d, 1H), 3.75 (d, 1H), 3.55 (d, 1H).

MS: 358 (M+H)

Example 20a

Compound I Wherein Ar is 3,4-DiClPhenyl, X is O, q is 1, (−) enantiomer, Substitution in Ortho Position, Y—R1 is $CH_2$ $CONH_2$.

The two enantiomers of Example 20 were separated by LC-Prep.

The HPLC analysis was performed as described here:
Column Chiralpak AS (10 μm, 250×4.6 mm, D068)
Mobile phase: Methanol/ethanol 1/1
Flow rate 0.5 mL/min
UV detection 220 nm Retention time: 8.8 min Optical rotation $[α_D]^{20}$ =−47.

Example 20b

Compound I Wherein Ar is 3,4-DiClPhenyl, X is O, q is 1, (+) Enantiomer, Substitution in Ortho Position, Y—R1 is $CH_2$ $CONH_2$.

The two enantiomers of Example 20 were separated by LC-Prep.

The HPLC analysis was performed as described here:
Column Chiralpak AS (10 μm, 250×4.6 mm, D068)
Mobile phase: Methanol/ethanol 1/1
Flow rate 0.5 mL/min
UV detection 220 nm Retention time: 10.9 min Optical rotation $[α_D]^{20}$=+43.

Example 21

N-(2-Hydroxy-ethyl)-2-(2-phenoxy-phenylmethanesulfinyl)-acetamide

Compound I Wherein Ar is Phenyl, X is O, q is 1, Substitution in Ortho Position, Y—$R^1$ is $CH_2$ $CONH(CH_2)_2OH$.

Reagents: Example 12 (0.46 g, 1.45 mmol) and a 30% by wt hydrogen peroxide solution (0.18 mL; 1.8 mmol).

Yield=62% (0.3 g; 0.9 mmol).

$^1$H-NMR (DMSO-$d_6$) δ: 8.25 (t, 1H), 7.45-7.25 (m, 4H), 7.2 (t, 2H), 7.0 (d, 2H), 6.8 (d, 1H), 4.7 (t, 1H), 4.3 (d, 1H), 4.05 (d, 1H), 3.75 (d, 1H), 3.6 (d, 1H), 3.4 (q, 2H), 3.2 (m, 2H).

MS: 356 (M+Na)

Example 22

1-(4-Acetyl-piperazin-1-yl)-2-[4-(3,4-dichloro-phenoxy)-phenylmethanesulfinyl]-ethanone Compound I Wherein Ar is 3,4-DiClPhenyl, X is O, q is 1, Substitution in Para Position, Y—$R^1$ is $CH_2$ CO-1-(4-acetyl)-piperazinyl).

Reagents: Example 11 (2.3 g, 5.1 mmol) and a 30% by wt hydrogen peroxide solution (0.6 mL; 5.9 mmol).

Yield=84% (2 g; 4.3 mmol).

$^1$H-NMR (DMSO-$d_6$) δ: 7.65 (d, 1H), 7.4 (d, 2H), 7.3 (broad s, 1H), 7.1 (d, 2H), 7.0 (broad d, 1H), 4.25, (d, 1H), 4.1 (d, 1H), 4.0 (m, 2H), 3.6-3.35 (broad, 8H), 2.0 (s, 3H).

MS: 469 (M+H).

Example 23

1-(4-Acetyl-piperazin-1-yl)-2-[4-(4-chloro-phenylsulfanyl)-phenylmethanesulfinyl]-ethanone Compound I Wherein Ar is 4-ClPhenyl, X is S, q is 1, Substitution in Para Position, Y—$R^1$ is $CH_2$ CO-1-(4-acetyl)-piperazinyl).

Reagents: Example 16 (1 g; 2.3 mmol), 30% by wt hydrogen peroxide solution (0.25 mL; 2.5 mmol).

Yield=61% (0.65 g; 1.4 mmol of Example 23 as a powder)

$^1$H-NMR (DMSO-$d_6$) δ: 7.45 (broad d, 2H), 7.3 (m, 6H), 4.25 (d, 1H), 4.05 (d, 1H), 3.95 (m, 2H), 3.5 (broad, 8H), 2 (s, 3H).

MS: 473 (M+Na).

Example 24

1-(4-Acetyl-piperazin-1-yl)-2-[4-(4-chloro-benzenesulfinyl)-phenylmethanesulfinyl]-ethanone Compound I Wherein Ar is 4-ClPhenyl, X is SO, q is 1, Substitution in Para Position, Y—$R^1$ is $CH_2$CO-1-(4-acetyl)-piperazinyl.

Reagents: Example 16 (1 g, 2.3 mmol), a 30% by wt hydrogen peroxide solution (0.25 mL; 2.5 mmol).

Yield=19% (0.2 g; 0.43 mmol of Example 24 as a powder).

$^1$H-NMR (DMSO-$d_6$) δ: 7.75 (broad d, 4H), 7.7 (d, 2H), 7.5 (d, 2H), 4.3 (d, 1H), 4.1 (d, 1H), 4.0 (broad s, 2H), 3.4 (broad, 8H), 2.05 (s, 3H).

MS:489 (M+Na).

Example 25

1-(4-Acetyl-piperazin-1-yl)-2-[2-chloro-4-(4-chloro-phenoxy)-phenylmethanesulfinyl]-ethanone Compound I Wherein Ar is 4-ClPhenyl, $R^2$ is 3-Cl, X is O, q is 1, Substitution in Para Position, Y—$R^1$ is $CH_2$ CO-1-(4-acetyl)-piperazinyl;

To a solution of Example 17 (3.15 g; 6.9 mmol) in acetic acid (20 mL), a 30% by wt hydrogen peroxide solution (0.82 mL; 8.1 mmol) was added. The mixture was stirred until no more starting material was detected (HPLC), and then concentrated under high vacuum. The resulting residue was taken into a mixture of water solution of sodium bicarbonate (200 mL) and ethyl acetate (200 mL). The organic layer was washed with water (1×100 mL), dried over $MgSO_4$ and concentrated in vacuo to afford compound 25 as a white powder.

Yield=83% (2.7 g; 5.8 mmol).

$^1$H-NMR (DMSO-$d_6$) δ: 7.5 (dd, 2H), 7.3 (m, 2H), 7.1 (dd, 2H), 6.8 (broad, 1H), 4.5 (d, 1H), 4.3 (d, 1H), 4.2 (m, 2H), 3.5 (broad, 8H), 2 (s, 3H).

MS 469 (M+H).

Example 26

2-[2-Chloro-4-(4-chloro-phenoxy)-phenylmethanesulfinyl]-acetamide

Compound I Wherein Ar is 4-ClPhenyl; $R^2$ is 3-Cl, X is O, q is 1, Substitution in Para position, Y—$R^1$ is $CH_2CONH2$.

Reagents: Example 18 (2.07 g; 6.0 mmol) and a 30% by wt hydrogen peroxide (0.7 mL; 6.9 mmol).

Yield=91% (1.95 g; 5.4 mmol).

$^1$H-NMR (DMSO-$d_6$) δ: 7.75 (broad s, 1H), 7.5 (broad d, 2H), 7.3 (m, 3H), 7.15 (broad d, 2H), 6.8 (broad m, 1H), 4.35 (d, 1H), 4.30 (d, 1H), 3.8 (d, 1H), 3.6 (d, 1H).

MS: 380 (M+Na).

Example 27

1-(4-Acetyl-piperazin-1-yl)-2-[4-(3,4-dichloro-phenoxy)-phenylmethanesulfonyl]-ethanone Compound I Wherein Ar is 3,4-DiClPhenyl, X is O, q is 2, Substitution in Para Position, Y—$R^1$ is $CH_2$ CO-1-(4-acetyl)-piperazinyl.

To a solution of Example 22 (0.85 g; 1.8 mmol) in acetic acid (20 mL), a 30% by wt hydrogen peroxide solution (0.56 mL; 5.5 mmol) was added. The mixture was stirred at 55° C. until no more starting material was detected (HPLC), and then concentrated under high vacuum. The resulting residue was taken into a mixture of water solution of sodium bicarbonate (200 mL) and ethyl acetate (200 mL). The organic layer was washed with water (1×100 mL), dried over $MgSO_4$ and concentrated in vacuo. The resulting residue was purified by column chromatography (eluent:methylenechloride/methanol 95/5) to generate Example 27 as a white powder.

Yield=71% (0.62 g; 1.3 mmol).

$^1$H-NMR (DMSO-$d_6$) δ: 7.7 (d, 1H), 7.45 (d, 2H), 7.30 (broad s, 1H), 7.1 (d, 2H), 7.0 (broad d, 1H), 4.7 (s, 2H), 4.35 (broad d, 2H), 3.6-3.4 (broad m, 8H), 2 (s, 3H).

MS: 507 (M+Na).

Example 27a

Compound I Wherein Ar is 4-ClPhenyl, X is O, $R^2$ is 4'-Cl, $R^3$ is H, q is 1, Substitution in ortho Position, Y—$R^1$ is $CH_2CONH_2$.

To a solution of Example 10a (3.5 g; 10.2 mmol) in acetic acid (30 mL), a 30% by wt hydrogen peroxide solution (1.36 mL; 13.3 mmol) was added. The mixture was stirred until no more starting material was detected (HPLC), and then concentrated under high vacuum. The residue was triturated in diethyloxide the resulting precipitated solid was filtered off, washed with diethyloxide and dried in vacuo to generate Example 27a as a white powder.

Yield=93% (3.4 g; 9.5 mmol).

$^1$H-NMR (DMSO-$d_6$) δ: 7.7 (broad s, 1H), 7.45 (broad m, 3H), 7.3 (broad s, 1H), 7.25 (broad d, 1H), 7.1 (broad d, 2H), 6.9 (broad s, 1H), 4.30 (d, 1H), 4.05 (d, 1H), 3.75 (d, 1H), 3.5 (d, 1H).

MS: 379.8 (M+Na).

Example 27b

Compound I Wherein Ar is 4-ClPhenyl, X is O, $R^2$ is 4'-Cl, $R^3$ is H, q is 2, Substitution in ortho Position, Y—$R^1$ is $CH_2CONH_2$.

To a solution of Example 27a (0.07 g; 0.2 mmol) in acetic acid (5 mL), a 30% by wt hydrogen peroxide solution (0.085 mL; 0.8 mmol) was added. The mixture was stirred at 55° C. until no more starting material was detected (HPLC), and then cooled to room temperature. The resulting precipitated solid was filtered off, washed with diethyl oxide and dried in vacuo to generate Example 27b as a white powder.

Yield=65% (0.48 g; 0.13 mmol).

$^1$H-NMR (DMSO-$d_6$) δ: 7.8 (broad s, 1H), 7.5 (broad m, 4H), 7.25 (broad d, 1H), 7.1 (broad d, 2H), 6.8 (broad s, 1H), 4.75 (s, 2H), 4.1 (s, 2H).

MS: 396 (M+Na).

G-Synthesis of Compounds I (q is 0, 1, 2)-Scheme B-Route B

Example 28

Compound I Wherein Ar is Phenyl, X is O, q is 1, Substitution in Para Position, Y—$R^1$ is $CH_2$ COOH.

To a solution of Example 4 (4 g; 14.6 mmol) in acetic acid (30 mL) a 30% by wt hydrogen peroxide solution (1.9 mL; 18 mmol) was added. The mixture was stirred until no more starting material was detected (HPLC), concentrated at high vacuum and triturated with ether to give Example 28 as an off-white solid.

Yield=82% (3.5 g; 12 mmol)
R$_f$=0.15 (eluent: 90:10 methylenechloride/methanol)

Example 29

N-Isopropropyl-2-(4-phenoxy-phenylmethanesulfinyl)-acetamide

Compound I Wherein Ar is Phenyl, X is O, q is 1, Substitution in Para Position, Y—R$^1$ is CH$_2$CO NHCH(CH$_3$)$_2$.

To a cooled solution of Example 28 (0.4 g; 1.4 mmol) in CH$_2$Cl$_2$ (25 mL), isopropylamine (0.095 g; 1.6 mmol), EDCI (0.31 g; 1.6 mmol) and HOBT (0.22 g; 1.6 mmol) were added. The reaction mixture was stirred until no more starting material was detected. Methylene chloride (100 mL) was added to the reaction mixture and the organic layer washed with 1N HCl (2×100 mL), water (100 mL), dried (MgSO$_4$) and concentrated in vacuo. The resulting residue was purified by column chromatography (eluent: methylenechloride/methanol (93/7) to generate Example 29 as a powder.

Yield=63% (0.35 g; 1 mmol).
$^1$H-NMR (DMSO-d$_6$) δ: 8.15 (d, 1H), 7.45 (broad t, 2H), 7.35 (broad d, 2H), 7.15 (broad t, 1H),7.0 (broad t, 4H), 4.2 (d, 1H), 3.95 (d, 1H), 3.85 (m, 1H), 3.55 (d, 1H), 3.45 (d, 1H), 1.0 (d, 6H).
MS: 354 (M+Na).

Example 30

[4-(3,4-dichloro-phenoxy)-phenylmethanesulfinyl]-acetic acid

Compound I Wherein Ar is 3,4-DiClPhenyl, X is O, q is 1, Substitution in Para Position, Y—R$^1$ is CH$_2$ COOH.

To a solution of Example 1 (0.94 g; 2.7 mmol) in acetic acid (20 mL) a 30% by wt hydrogen peroxide solution (0.32 mL; 3.2 mmol) was added. The mixture was stirred until no more starting material was detected (HPLC), concentrated at high vacuum and triturated with ether to give Example 30 as an off-white solid.

Yield=57% (0.55 g; 1.53 mmol)
$^1$H-NMR (DMSO-d$_6$) δ: 7.7 (d, 1H), 7.4-7.3 (m, 3H), 7.35 (broad, 2H), 7.1 (d, 2H), 7.0 (broad d, 1H), 4.2 (d, 1H), 4.1 (d, 1H), 3.8 (d, 1H), 3.6 (d, 1H).
MS: 381 (M+Na).

Example 30a

[2-(3,4-Dichloro-phenoxy)-phenylmethanesulfinyl]-acetic acid

Compound I Wherein Ar is 3,4-DiClPhenyl, X is O, q is 1, Substitution in Ortho Postion, Y—R1 is CH$_2$ COOH.

To a solution of Example 2 (20.58 g, 60 mmol) in glacial acetic acid (60 mL) was added 35% aqueous hydrogen peroxide (6.6 mL) at room temperature.The mixture was stirred until no more starting material was detected (TLC). After 2 h of stirring, the sulfoxyde precipitated; the precipitate was filtered, washed with water and diisopropyl oxide successively, dried under vacuum to yield Example 30a (white powder; 18.36 g)

Yield=85%.
R$_t$: 12.25 min.
$^1$H-NMR (DMSO) δ (ppm): 7.65 (d, 1H) 7.45 (d, 1H), 7.4 (t, 1H), 7.3-7.15 (m, 2H), 7.05-6.9 (m, 2H), 4.25 (d, 1H), 4.1 (d, 1H), 3.9 (d, 1H), 3.65 (d, 1H).

Example 30b

[2-(3,4-Dichloro-phenoxy)-phenylmethanesulfonyl]-acetic acid

Compound I Wherein Ar is 3,4-DiClPhenyl, X is O, q is 2, Substitution in Ortho Position, Y—R1 is CH$_2$ COOH.

To a suspension of Example 30a (1.79 g, 5 mmol) in glacial acetic acid (5 mL) at room temperature was added 35% aqueous hydrogen peroxide (1.5 mL). The mixture was heated to 50° C. for 4 h until no more starting material was detected (HPLC). After concentration, the residue was triturated in water to give a precipitate that was filtered, washed with water and diisopropyl ether successively, dried under vacuum to yield Example 30b (white powder; 0.78 g)

Yield=42%.
R$_t$: 13.5 min.
$^1$H-NMR (DMSO) δ (ppm): 7.6 (d, 1H) 7.5 (d, 1H), 7.4 (t, 1H), 7.3-7.2 (m, 2H), 7.05-6.9 (m, 2H), 4.7 (s, 2H), 4.25 (s, 2H).
MS: 373 (M–H); 749 (2M+H)

Example 30c

Compound I Wherein Ar is 3,4-DiClPhenyl, X is O, q is 0, Substitution in Ortho Position, Y—R1 is CH$_2$ COO (1R,2S,5R)Menthyl.

To a stirred solution of Example 2 (5 g; 14.6 mmol) in DMF (30 mL), TBTU (o-Benzotriazol-1-yl-N,N,N',N'-tetramethyluronium tetrafluoroborate) (7 g; 21.8 mmol), N-methyl morpholine (2.45 mL; 22.2 mmol) and (1R, 2S, 5R) (−) menthol were added. The reaction mixture was stirred for fifteen hours, and then ethyl acetate (200 mL) and brine (200 mL) were added into it. The resulting organic layer was evaporated and the residue was purified by flash chromatography (eluent:cyclohexane/ethyl acetate (95/5) to afford Example 30c as a yellow oil.

Yield=60% (4.2 g; 8.7 mmol).
$^1$H-NMR (DMSO-d$_6$) δ: 7.7 (broad d, 1H), 7.45 (broad d, 1H), 7.30 (broad t, 1H), 7.2 (broad, 2H), 6.95 (broad m, 2H), 4.55 (m, 1H), 3.8 (s, 2H), 3.25 (s, 2H), 1.8 (broad m, 2H), 1.7 (broad m, 2H), 1.45 (broad, 1H), 1.30 (broad t, 1H), 1.0 (broad, 1H), 0.85 (broad t, 8H), 0.70 (d, 3H).

Example 30d

Compound I Wherein Ar is 3,4-DiClPhenyl, X is O, q is 1, Substitution in ortho Position, Y—R1is CH$_2$ COOH, enantiomer (−).

To a solution of Example 30c (2.09 g; 4.35 mmol) in acetic acid (25 mL), a 30% by wt hydrogen peroxide solution (0.39 mL; 4.4 mmol) was added. The mixture was stirred at room temperature until no more starting material was detected (HPLC), and then the solvent was evaporated. The residue was purified by flash chromatography (eluent: cyclohexane/ethyl acetate (8/2) to afford a mixture of two diastereoisomers which were separated by LC Preparative. The HPLC analysis was performed as described here:

Column AGP-Chiral (5 μm, 150×4. mm)
Mobile phase: (aqueous ammonium acetate 0.1M)/n-Butanol: 98.5/1.5
Flow rate 0.8 mL/min
UV detection 230 nm
Results: Diastereoisomer 1: retention time 8.1 min,
Diastereosomer 2: retention time 9.7 min.

To a solution of diastereoisomer 2 in methanol (28 mL) and tetrahydrofuran (75 mL), barium hydroxide octahydrate (0.25 g; 0.8 mmol) was added. The mixture was stirred at room temperature until no more starting material was detected (HPLC), and then the solvent was evaporated. Methylene chloride (50 mL) was added into it. The organic layer was washed with water (1×50 mL), dried over $MgSO_4$ and concentrated in vacuo. The resulting residue was washed with ether to afford a white powder. To a mixture of this powder in water (17 mL) and ethanol (5 mL), an aqueous hydrochloric acid solution (3 mL, 0.5N) was added. The mixture was stirred at room temperature for 6 hours. The resulting precipitated solid was filtered off, washed with water and dried in vacuo to generate Example 30d as a white powder.

Yield=20% (0.317 g; 0.89 mmol).

$^1$H-NMR (DMSO-$d_6$) δ: 7.7 (broad d, 1H), 7.45 (broad d, 1H), 7.30 (broad t, 1H), 7.25 (broad m, 2H), 7.0 (broad t, 2H), 4.25 (d, 1H), 4.1 (d, 1H), 3.95 (s, 1H), 3.7 (s, 1H).

Optical rotation $[\alpha_D]^{20}$=−49.

Enantiomeric excess >98%.

Example 30e

Compound I Wherein Ar is 3,4-DiClPhenyl, X is O, q is 1, Substitution in )rtho Position, Y—R1 is $CH_2$ COOH, enantiomer (+).

To a solution of diastereoisomer 1 (isolated during the synthesis of Example 30d) in ethanol (5 mL) and water (7.5 mL), sodium hydroxide was added. The mixture was stirred at room temperature until no more starting material was detected (HPLC). Aqueous hydrochloric acid solution (10 mL, 0.5N) and methylene chloride (50 mL) were added into it. The organic layer was washed with water (1×50 mL), dried over $MgSO_4$ and concentrated in vacuo. The resulting residue was triturated in diethyl oxide and the precipitated solid was filtered off, washed with diethyl oxide and dried in vacuo to generate Example 30e as a white powder.

Yield=16% (0.255 g; 0.71 mmol).

$^1$H-NMR (DMSO-$d_6$) δ: 7.7 (broad d, 1H), 7.45 (broad d, 1H), 7.30 (broad t, 1H), 7.25 (broad m, 2H), 7.0 (broad t, 2H), 4.25 (d, 1H), 4.1 (d, 1H), 3.95 (s, 1H), 3.7 (s, 1H).

Optical rotation $[\alpha_D]^{20}$=+46.

Enantiomeric excess >98%.

Example 30f

[2-(3,4-Dichloro-phenoxy)-phenylmethanesulfanyl]-N,N-dimethyl-acetamide

Compound I Wherein Ar is 3,4-DiClPhenyl, X is O, q is 0, Substitution in Ortho Postion, Y—R1is $CH_2$ CON$(CH_3)_2$ To a cooled (ice-bath) solution of Example 2 (3.43 g, 10 mmol) in $CH_2Cl_2$ (60 mL), was added successively dimethylamine (0.495 g, 1.25 mL, 11 mmol), EDCI (2.1 g, 11 mmol) and HOBT (1.48 g, 11 mmol). The cooling bath was removed and the reaction mixture was stirred at room temperature for one night. It was then diluted with $CH_2Cl_2$ (40ml), washed successively with water (60 ml), aqueous $NaHCO_3$, water (60ml) and dried over $Na_2SO_4$. On concentration, the solution generated an orange oil that was triturated in diisopropyl ether to yield the title compound Example 30f (2.9 g; beige powder).

Yield=78%.

$R_f$ ($CH_2Cl_2/CH_3OH$ 9/1)=0.65.

$R_t$: 15.86 min.

Example 30 g

[2-(3,4-Dichloro-phenoxy)-phenylmethanesulfinyl]-N,N-dimethyl-acetamide

Compound I Wherein Ar is 3,4-DiClPhenyl, X is O, q is 1, Substitution in Ortho Postion, Y—R1 is $CH_2$ CON$(CH_3)_2$ To a suspension of Example 30f (2.91 g, 7.9 mmol) in glacial acetic acid (10 mL) at room temperature was added 35% aqueous hydrogen peroxide (0.87 mL). The mixture was stirred for 3 h until no more starting material was detected (HPLC). After concentration, the residue was triturated in diisopropyl ether to give a solid that was filtered, washed with diisopropyl ether and dried under vacuum to yield Example 30 g (slightly beige powder; 0.78 g).

Yield=86%.

$R_t$: 12.32 min.

$^1$H-NMR (DMSO) δ (ppm): 7.65 (d, 1H) 7.45 (d, 1H), 7.4 (t, 1H), 7.25-7.2 (m, 2H), 7 (dd, 2H), 4.25 (d, 1H), 4.15 (d, 1H), 3.95 (s, 2H), 2.95 (s, 3H), 2.75 (s, 3H).

MS:408 (M+Na).

Compounds 31 through 112 were prepared following the same multistep general method as described in scheme B utilizing the appropriate substituted amine —$NR^{12}R^{13}$ in steps 5 or 6. The analytical data is presented by each compounds molecular formula and masse spectrum (M+H) or (M+Na) as shown in the following Table 2.

TABLE 2

| Example N° | Molecular Formula | Peak | Mass |
|---|---|---|---|
| Scheme B, route A | | | |
| 31 | $C_{19}H_{21}NO_3S$ | M + H | 344 |
| 32 | $C_{15}H_{15}NO_3S$ | M + H | 290 |
| 33 | $C_{17}H_{19}NO_3S$ | M + H | 318 |
| 34 | $C_{18}H_{21}NO_3S$ | M + H | 332 |
| 35 | $C_{21}H_{24}N_2O_4S$ | M + H | 401 |
| 36 | $C_{16}H_{17}NO_4S$ | M + Na | 342 |
| 37 | $C_{22}H_{26}N_2O_5S$ | M + Na | 453 |
| 38 | $C_{20}H_{24}N_2O_4S.C_4H_4O_4$ | M + H | 389 |
| 39 | $C_{15}H_{13}Cl_2NO_3S$ | M + Na | 380 |
| 40 | $C_{21}H_{22}Cl_2N_2O_4S$ | M + H | 469 |
| 41 | $C_{20}H_{21}Cl_2N_3O_4S$ | M + H | 470 |
| 42 | $C_{16}H_{17}NO_4S$ | M + Na | 342 |
| 43 | $C_{15}H_{14}ClNO_3S$ | M + Na | 346 |
| 44 | $C_{15}H_{15}NO_4S$ | M + Na | 328 |
| 45 | $C_{15}H_{14}ClNO_3S$ | M + H | 324 |
| 46 | $C_{21}H_{23}ClN_2O_4S$ | M + Na | 457 |
| 47 | $C_{19}H_{21}ClN_2O_3S.C_4H_4O_4$ | M + H | 393 |
| 48 | $C_{21}H_{23}FN_2O_4S$ | M + H | 419 |
| 49 | $C_{21}H_{23}FN_2O_4S$ | M + H | 419 |
| 50 | $C_{15}H_{14}FNO_3S$ | M + Na | 330 |
| 51 | $C_{15}H_{14}FNO_3S$ | M + Na | 330 |
| 52 | $C_{19}H_{17}NO_3S$ | M + Na | 362 |
| 53 | $C_{26}H_{27}NO_4S$ | M + Na | 473 |
| 54 | $C_{19}H_{17}NO_3S$ | M + Na | 362 |
| 55 | $C_{21}H_{19}NO_3S$ | M + Na | 388 |
| 56 | $C_{21}H_{19}NO_3S$ | M + H | 366 |
| 57 | $C_{21}H_{23}ClN_2O_4S$ | M + H | 435 |
| 58 | $C_{25}H_{26}N_2O_4S$ | M + Na | 473 |
| 59 | $C_{27}H_{28}N_2O_4S$ | M + H | 477 |
| 60 | $C_{27}H_{28}N_2O_4S$ | M + Na | 499 |
| 61 | $C_{21}H_{23}ClN_2O_4S$ | M + Na | 457 |
| 62 | $C_{21}H_{26}N_3O_4S.HCl$ | M + H | 403 |
| 63 | $C_{22}H_{24}Cl_2N_2O_5S$ | M + H | 499 |
| 64 | $C_{21}H_{25}FN_2O_4S.HCl$ | M + H | 421 |
| 65 | $C_{21}H_{24}Cl_2N_2O_4S.HCl$ | M + H | 471 |
| 66 | $C_{20}H_{23}FN_2O_3S.HCl$ | M + H | 391 |
| 67 | $C_{15}H_{14}ClNO_3S$ | M + Na | 346 |
| 68 | $C_{22}H_{25}FN_2O_5S$ | M + H | 449 |
| 69 | $C_{23}H_{28}N_2O_6S$ | M + Na | 483 |
| 70 | $C_{22}H_{25}ClN_2O_4S_2$ | M + Na | 503 |

TABLE 2-continued

| Example N° | Molecular Formula | Peak | Mass |
|---|---|---|---|
| 71 | $C_{22}H_{25}ClN_2O_5S_2$ | M + Na | 519 |
| 72 | $C_{22}H_{24}Cl_2N_2O_5S$ | M + Na | 521 |
| 73 | $C_{19}H_{21}ClN_2O_2S_2$ | M + H | 409 |
| 74 | $C_{21}H_{22}Cl_2N_2O_4S$ | M + Na | 491 |
| 75 | $C_{21}H_{22}Cl_2N_2O_4S$ | M + Na | 491 |
| 76 | $C_{15}H_{13}Cl_2NO_3S$ | M + Na | 380 |
| 77 | $C_{15}H_{13}Cl_2NO_3S$ | M + Na | 380 |
| 78 | $C_{21}H_{22}Cl_2N_2O_4S$ | M + Na | 491 |
| 79 | $C_{21}H_{22}Cl_2N_2O_4S$ | M + H | 469 |
| 80 | $C_{15}H_{13}Cl_2NO_3S$ | M + Na | 380 |
| 81 | $C_{15}H_{13}Cl_2NO_3S$ | M + H | 358 |
| 82 | $C_{21}H_{22}Cl_2N_2O_4S$ | M + H | 469 |
| 83 | $C_{21}H_{22}Cl_2N_2O_4S$ | M + H | 469 |
| 84 | $C_{15}H_{13}Cl_2NO_3S$ | M + Na | 380 |
| 85 | $C_{15}H_{13}Cl_2NO_3S$ | M + H | 358 |
| 86 | $C_{21}H_{22}Cl_2N_2O_4S$ | M + H | 469 |
| 87 | $C_{21}H_{22}Cl_2N_2O_3S_2$ | M + H | 485 |
| 88 | $C_{15}H_{13}Cl_2NO_3S$ | M + Na | 380 |
| 89 | $C_{15}H_{13}Cl_2NO_2S_2$ | M + Na | 396 |
| 90 | $C_{21}H_{22}Cl_2N_2O_4S$ | M + Na | 491 |
| 91 | $C_{21}H_{22}Cl_2N_2O_4S$ | M + Na | 491 |
| 92 | $C_{15}H_{13}Cl_2NO_3S$ | M + Na | 380 |
| 93 | $C_{15}H_{13}Cl_2NO_4S$ | M + Na | 396 |
| 94 | $C_{15}H_{13}Cl_2NO_3S$ | M + Na | 380 |
| 95 | $C_{21}H_{23}FN_2O_5S$ | M + Na | 457 |
| 96 | $C_{21}H_{22}Cl_2N_2O_5S$ | M + Na | 507 |
| 97 | $C_{15}H_{15}NO_3S$ | M + H | 290 |
| 98 | $C_{19}H_{21}NO_3S$ | M + H | 344 |
| 99 | $C_{17}H_{19}NO_3S$ | M + H | 318 |
| 100 | $C_{17}H_{19}NO_3S$ | M + H | 318 |
| 101 | $C_{19}H_{21}NO_3S$ | M + H | 344 |
| 102 | $C_{15}H_{15}NO_3S$ | M + Na | 312 |
| 103 | $C_{17}H_{16}N_2O_3S$ | M + Na | 351 |
| 104 | $C_{18}H_{21}NO_3S$ | M + H | 332 |
| 105 | $C_{19}H_{23}NO_3S$ | M + H | 346 |
| 106 | $C_{20}H_{23}NO_4S$ | M + H | 374 |
| 107 | $C_{21}H_{24}N_2O_4S$ | M + Na | 423 |
| 108 | $C_{17}H_{19}NO_4S$ | M + H | 334 |
| 109 | $C_{20}H_{23}NO_4S$ | M + H | 374 |
| 109a | $C_{15}H_{14}ClNO_3S$ | M + Na | 346 |
| 109b | $C_{15}H_{13}ClFNO_3S$ | M + Na | 364 |
| 109c | $C_{15}H_{13}ClFNO_3S$ | M + Na | 364 |
| 109d | $C_{15}H_{13}ClFNO_4S$ | M + Na | 380 |
| 109e | $C_{15}H_{12}ClF2NO_3S$ | M + Na | 381.8 |
| 109f | $C_{15}H_{13}Cl_2NO_4S$ | M + Na | 395.7 |
| Scheme B, route B | | | |
| 110 | $C_{21}H_{24}N_2O_4S$ | M + Na | 423 |
| 111 | $C_{17}H_{19}NO_4S$ | M + Na | 356 |
| 112 | $C_{20}H_{23}NO_4S$ | M + Na | 396 |
| 112a | $C_{16}H_{15}Cl_2NO_3S$ | M + Na | 394 |
| | | 2M + Na | 766 |
| 112b | $C_{19}H_{21}Cl_2NO_3S$ | M + Na | 436 |
| | | 2M + Na | 851 |

II-Compounds Prepared According to Scheme C.

Examples 113 to 149 were synthesized according to Scheme C.

A-Preparation of Compound J

Compound 12

Compound J wherein Y—$R^1$ is $CH_2$ $COOCH_3$, $NO_2$ is in ortho position, $R^2$ and $R^3$ are H.

To a stirred solution of 2-nitrobenzyl bromide (43.2 g; 200 mmol) in dry acetone (200 mL), methylthioglycolate (19 ml; 212 mmol), potassium iodide (0.2 g; 1.2 mmol) and potassium carbonate (27.6 g; 200 nmmol) were added. The reaction mixture was refluxed for 4 hours and then the solvent removed. The resulting residue was taken into a mixture of water (500 mL) and ether (500 mL). The organic layer was washed with water, dried over $MgSO_4$ and concentrated in vacuo to give compound 12 as an orange oil.

Yield: 100% (48.2 g; 199.9 mmol)

$R_f$=0.55 (eluent: methylenechloride)

Compound 13

Compound J wherein Y—$R^1$ is $CH_2$ COOH, $NO_2$ is in ortho position, $R^2$ and $R^3$ are H.

To a stirred solution of 2-nitrobenzyl bromide (25 g; 116 mmol) in dry acetone (100 mL), thioglycolic acid (8.5 mL; 122 mmol), potassium iodide (0.09 g; 0.5 mmol) and potassium carbonate (17.5 g; 127 mmol) were added. The reaction mixture. was refluxed overnight and the solvent was removed. The resulting residue was taken into water (500 mL) and the cooled aqueous mixture acidified with hydrochloric acid 4N to pH 2. The precipitate was extracted with ethylacetate (500 mL) and the organic layer washed with water (2×200 mL), dried over MgSO4 and concentrated in vacuo to furnish an oil that was purified by column chromatography (eluent: methylenechloride/methanol (9/1) to afford compound 13 as a yellow powder after solvent evaporation.

Yield: 76% (19.9 g; 88 mmol).

$R_f$=0.35 (eluent: 9:1 methylenechloride:methanol).

Compound 13a

Compound J wherein Y—$R^1$ is $CH_2$ $COOCH_3$, $NO_2$ is in para position, $R^2$ and $R^3$ are H.

To a stirred solution of 4-nitrobenzyl bromide (43.2 g; 200 mmol) in dry acetone (200 mL), methylthioglycolate (19 mL; 212 mmol), potassium iodide (0.2 g; 1.2 mmol) and potassium carbonate (27.6 g; 200 mmol) were added. The reaction mixture was refluxed for 4 hours and then the solvent removed. The resulting residue was taken into a mixture of water (500 mL) and ether (500 mL). The organic layer was washed with water, dried over $MgSO_4$ and concentrated in vacuo to give compound 13a as an orange oil.

Yield: 100% (48.2 g; 199.9 mmol)

$R_f$=0.95 (eluent: 9:1 methylenechloride/methanol)

B-Preparation of Compound K

Compound 14

Compound K wherein Y—$R^1$ is $CH_2CONH_2$, $NO_2$ is in ortho position, $R^2$ and $R^3$ are H.

To a stirred solution of compound 12 (20 g, 82.9 mmol) in methanol (50 mL), 28% $NH_4OH$ (50 mL) was added. The reaction mixture was stirred overnight, the methanol evaporated and water (250 mL) added into the mixture. The precipitated solid was filtered off, washed with water and dried in vacuo to generate compound 14 as a yellow powder.

Yield: 81% (15.1 g; 67 mmol)

$R_f$=0.28 (eluent: 95:5 methylenechloride/methanol)

Compound 15

Compound K wherein Y—$R^1$ is $CH_2CO$-1-(yl)-piperazinyl, $NO_2$ is in ortho position, $R^2$ and $R^3$ are H.

To a cooled solution of compound 13 (12 g, 53 mmol) in $CH_2Cl_2$ (200 mL), N-acetylpiperazine (7.3 g; 57 mmol), EDCI (10.9 g; 57 mmol) and HOBT (7.8 g; 58 mmol) were added. The reaction mixture was stirred until no more starting material was detected. The organic layer was washed with 1N HCl (2×100 mL), water (100 mL), dried ($MgSO_4$) and concentrated in vacuo. Trituration of the resulting residue with $Et_2O$, filtration and drying under vacuum gave compound 15 as an off-white solid.

Yield: 92% (16.4 g; 49 mmol).

$R_f$=0.23 (eluent: 97:3 methylenechloride/methanol).

Compound 15a

Compound K wherein Y—$R^1$ is $CH_2CONH_2$, $NO_2$ is in para position, $R^2$ and $R^3$ are H.

To a stirred solution of compound 13a (48.2 g, 200 mmol) in methanol (250 mL), 28% $NH_4OH$ (250 mL) was added. The reaction mixture was stirred overnight, the methanol evaporated and water (700 mL) added into the mixture. The precipitated solid was filtered off, washed with water and dried in vacuo to generate compound 15a as an orange powder.

Yield: 78% (35.5 g; 157 mmol)

$R_f$=0.55 (eluent: 9:1 methylenechloride/methanol).

C-Preparation of Compound L

Compound 16

Compound L wherein Y—$R^1$ is $CH_2CONH_2$, q is 1, $NO_2$ is in ortho position, $R^2$ and $R^3$ are H.

To a solution of compound 14 (8 g; 35.4 mmol) in acetic acid (120 mL), a 30% by wt hydrogen peroxide solution (4.5 mL; 40 mmol) was added. The reaction mixture was stirred overnight and concentrated under high vacuum. Trituration of the resulting residue with ethylacetate, filtration and drying under vacuum gave compound 16 as a yellow powder.

Yield: 90% (7.86 g; 32 mmol).

$R_f$=0.34 (eluent: 9:1 methylenechloride/methanol).

Compound 17

Compound L wherein Y—$R^1$ is $CH_2CO$-1-(4-acetyl)-piperazinyl, q is 1, $NO_2$ is in ortho position, $R^2$ and $R^3$ are H.

To a solution of compound 15 (8.2 g; 24.3 mmol) in acetic acid (60 mL), a 30% by wt hydrogen peroxide solution (2.8 mL; 28 mmol) was added. The reaction mixture was stirred for two hours and concentrated at high vacuum. The resulting residue was purified by column chromatography (eluent: with methylenechloride/methanol (9/1) to afford compound 17 as a yellow powder.

Yield: 74% (6.4 g; 18 mmol).

$R_f$=0.40 (eluent: 9:1 methylenechloride/methanol).

D-Preparation of Compound M'

Compound 17a

Compound M wherein Y—$R^1$ is $CH_2CONH_2$, q is 0, $NH_2$ is in para position, $R^2$ and $R^3$ are H.

To a stirred solution of compound 15a (5.5 g, 24 mmol) in acetic acid (60 mL) and water (120 mL), iron (6.7 g, 120 mmol) was added. The reaction mixture was refluxed for 15 minutes. The iron was removed by filtration on a pad of Celite, and the filtrate was evaporated. The resulting residue was purified by column chromatography (eluent: methylenechloride/methanol (9/1) to generate compound 17a as a grey powder.

Yield: 71% (3.36 g; 17 mmol).

$R_f$=0.46 (eluent: 9:1 methylenechloride/methanol).

E-Preparation of Compound M

Compound 18

Compound M wherein Y—$R^1$ is $CH_2CONH_2$, q is 1, $NH_2$ is in ortho position, $R^2$ and $R^3$ are H.

Compound 16 wherein (7.86 g, 32.5 mmol) in a mixture of DMF (50 mL) and MeOH (50 mL) was reduced in the presence of 10% Pd/C (1.6 g) in an autoclave under hydrogen pressure (50 PSI) for 12 hours. The catalyst was removed by filtration on a pad of Celite, and the filtrate was evaporated. Trituration of the resulting residue with ethylacetate, filtration and drying under vacuum gave compound 18 as an off-white solid.

Yield: 80% (5.6 g; 26 mmol).

$R_f$=0.25 (eluent: 5.6 g; 26 mmol).

Compound 19

Compound M wherein Y—$R^1$ is $CH_2CO$-1-(4-acetyl)-piperazinyl, q is 1, $NH_2$ is in ortho position, $R^2$ and $R^3$ are H.

Compound 17 (2.1 g, 5.9 mmol) in MeOH (50 mL) was reduced in the presence of 10% Pd/C (0.2 g) in an autoclave under an hydrogen pressure (50 PSI) for 18 hours. The catalyst was removed by filtration on a pad of Celite, and the filtrate was evaporated. The resulting residue was purified by column chromatography (eluent: methylenechloride/methanol (96/4) to generate compound 19 as a white powder.

Yield: 68% (1.3 g; 4 mmol).

$R_f$=0.29 (eluent: 9:1 methylenechloride/methanol).

Compound 19a

Compound M wherein Y—$R^1$ is $CH_2CONH_2$, q is 1, $NH_2$ is in para position, $R^2$ and $R^3$ are H.

To a solution of compound 17a (1 g; 5.09 mmol) in acetic acid (15 mL), a 30% by wt hydrogen peroxide solution (0.6 mL; 5.9 mmol) was added. The reaction mixture was stirred for three hours and then diethyloxide was added into the mixture. The precipitated solid was filtered off, washed with diethyloxide and dried in vacuo to generate compound 19a as an yellow powder.

Yield: 65% (0.7 g; 3.3 mmol).

$R_f$=0.20 (eluent: 9:1 methylenechloride/methanol).

F-Preparation of Compound I

Example 113

N-(2-carbamoylmethanesulfinylmethyl-phenyl)-4-chloro-benzamide

Compound I wherein Ar is 4-ClPhenyl, X is CONH, q is 1, substitution in ortho postion, $R^2$ and $R^3$ are H, Y—$R^1$ is $CH_2CONH_2$.

To a stirred solution of compound 18 (1 g; 4.7 mmol) in $CH_2Cl_2$ (50 mL) were added pyridine (0.76 mL; 9.4 mmol) and 4-chlorobenzoylchloride (0.6 mL; 4.7 mmol). The reaction mixture was stirred for one hour and filtered. The resulting solid was washed with water and methylenechloride and dried under vacuum to give Example 113 as a solid.

Yield: 81% (1.32 g; 3.8 mmol).

$^1$H-NMR (DMSO-$d_6$) δ: 10.6 (s, 1H), 8.0 (broad d, 2H), 7.75 (broad, 2H), 7.6 (broad d, 2H), 7.4 (broad, 3H), 7.25 (broad, 1H), 4.55 (d, 1H), 4.3 (d, 1H), 3.8 (d, 1H).

MS: 373 (M+Na).

The following examples were prepared according to the procedure as described for Example 113.

Example 114

N-(2-Carbamoylmethanesulfinylmethyl-phenyl)-3,4-dimethoxy-benzamide

Compound I wherein Ar is 3,4-DiOCH$_3$Phenyl, X is CONH, q is 1, substitution in ortho position, $R^2$ and $R^3$ are H, Y—$R^1$ is $CH_2CONH_2$.

Reagents: compound 18 (1 g; 4.7 mmol) and 3,4-dimethoxybenzoyl chloride (0.94 g; 4.7 mmol). Example 114 is a solid.

Yield: 49% (0.87 g; 2.3 mmol).

$^1$H-NMR (DMSO-$d_6$) δ: 10.5 (s, 1H), 7.8 (d, 1H), 7.75 (broad, 1H), 7.6 (d, 1H), 7.55 (broad, 1H), 7.35 (broad, 3H), 7.2 (t, 1H), 7.1 (d, 1H), 4.5 (d, 1H), 4.3 (d, 1H), 3.85 (s, 6H), 3.75 (d, 1H).

MS: 399 (M+Na)

Example 115

Naphtalene-2-carboxylic acid (2-carbamoylmethanesulfinylmethyl-phenyl)-amide

Compound I wherein Ar is 2-Naphthyl, X is CONH, q is 1, substitution in ortho postion, $R^2$ and $R^3$ are H, Y—$R^1$ is $CH_2CONH_2$.

Reagents: compound 18 (1 g; 4.7 mmol) and 2-naphthoyl-chloride (0.92 g; 4.7 mmol). Example 115 is a solid.

Yield: 58% (1 g; 2.7 mmol)

$^1$H-NMR (DMSO-$d_6$) δ: 10.75 (s, 1H), 8.7 (s, 1H), 8.1 (m, 3H), 8.05 (d, 1H), 7.8 (d, 1H), 7.75 (s, 1H), 7.60 (m, 2H), 7.45 (m, 3H), 7.30 (t, 1H), 4.55 (d, 1H), 4.30 (d, 1H), 3.8 (d, 1H), 3.55 (d, 1H).

MS: 367 (M+H).

Example 116

N-{2-[2-(4-Acetyl-piperazin-1-yl)-2-oxo-ethanesulfinylmethyl]-phenyl}-4-chloro-benzamide Compound I wherein Ar is 4-ClPh, X is CONH, q is 1, substitution in ortho postion, $R^2$ and $R^3$ are H, Y—$R^1$ is $CH_2CO$-1-(4-acetyl)-piperazinyl.

To a stirred solution of compound 19 (1 g; 3.7 mmol) in $CH_2Cl_2$ (40 mL), pyridine (0.76 mL; 9.4 mmol) and 4-chlorobenzoylchloride (0.6 mL; 4.7 mmol) were added. The reaction mixture was stirred for one hour and then the solvent was removed. Trituration of the resulting residue with ethylacetate, filtration and drying under vacuum gave Example 116 as a powder.

Yield: 65% (0.92 g; 2 mmol).

$^1$H-NMR (DMSO-$d_6$) δ: 10.55 (s, 1H), 8.0 (d, 2H), 7.75 (d, 1H), 7.65 (dd, 2H), 7.45 (m, 2H), 7.25 (t, 1H), 4.45 (m, 1H), 4.35 (m, 1H), 4.2 (d, 1H), 4.1 (d, 1H), 3.45 (broad, 8H), 2.0 (s, 3H).

MS: 484 (M+Na).

Examples 117 through 129 were prepared following the same multistep general method as described for Example 116 utilizing the appropriate substituted amine —$NR^{12}R^{13}$ and the appropriate benzoyl chloride in step 4. The analytical data is presented by each compounds molecular formula and masse spectrum (M+H) or (M+Na) as shown in the following Table 3.

TABLE 3

| Example N° | Molecular Formula | Peak | Mass |
|---|---|---|---|
| 117 | $C_{16}H_{14}F_2N_2O_3S$ | M + H | 353 |
| 118 | $C_{18}H_{20}N_2O_5S$ | M + H | 377 |
| 119 | $C_{19}H_{22}N_2O_6S$ | M + H | 407 |
| 120 | $C_{18}H_{20}N_2O_5S$ | M + H | 377 |
| 121 | $C_{24}H_{29}N_3O_6S$ | M + H | 488 |
| 122 | $C_{24}H_{29}N_3O_6S$ | M + H | 488 |
| 123 | $C_{22}H_{24}FN_3O_4S$ | M + H | 446 |
| 124 | $C_{22}H_{23}Cl_2N_3O_4S$ | M + H | 496 |
| 125 | $C_{18}H_{20}N_2O_5S$ | M + H | 377 |
| 126 | $C_{16}H_{15}FN_2O_3S$ | M + H | 335 |
| 127 | $C_{16}H_{14}Cl_2N_2O_3S$ | M + Na | 407 |
| 128 | C22H23Cl2N3O4S | M + Na | 518 |
| 129 | C22H24FN3O4S | M + Na | 468 |

Example 130

N-{2-[2-(4-Acetyl-piperazin-1-yl)-2-oxo-ethanesulfinylmethyl]-phenyl}-3,4-dichloro-benzenesul Compound I wherein Ar is 3,4-DiClPh, X is $SO_2NH$, q is 1, substitution in ortho postion, $R^2$ and $R^3$ are H, Y—$R^1$ is $CH_2CO$-1-(4-acetyl)-piperazinyl.

To a stirred solution of compound 19 (1 g; 3.1 mmol) in $CH_2Cl_2$ (30 mL), pyridine (0.5 mL; 6.2 mmol) and 3,4-Dichlorobenzenesulfonylchloride (0.48 mL; 3.1 mmol) were added. The reaction mixture was stirred for twelve hours and then, methylene chloride (200 mL) were added into it. The resulting mixture was washed with an aqueous hydrochloric acid solution 1N (1×150 mL) and evaporated. The resulting residue was purified by column chromatography (eluent: methylenechloride/methanol 9/1) to generate Example 130 as a white powder.

Yield: 91% (1.5 g; 2.8 mmol).

$R_f$=0.46 (eluent: 9:1 methylenechloride/methanol).

$^1$H-NMR (DMSO-$d_6$) δ: 10.1 (s, 1H), 7.85 (broad d, 2H), 7.70 (broad d, 1H), 7.40-7.30 (m, 3H), 7.00 (broad m, 1H), 4.30 (d, 1H), 4.20-4.00 (broad m, 3H), 3.60-3.40 (broad, 8H), 2.0 (s, 3H).

MS: 554 (M+Na).

Examples 131 through 133 were prepared following the same multistep general method as described for Example 130 utilizing the appropriate substituted amine —$NR^{12}R^{13}$ and the appropriate sulfonylchloride in step 4. The analytical data is presented by each compounds molecular formula and masse spectrum (M+H) or (M+Na) as shown in the following Table 4:

TABLE 4

| Example N° | Molecular Formula | Peak | Mass |
|---|---|---|---|
| 131 | $C_{21}H_{24}FN_3O_5S_2$ | M + Na | 504 |
| 132 | $C_{21}H_{24}ClN_3O_5S_2$ | M-1(ESI-) | 496 |
| 133 | $C_{21}H_{23}Cl_2N_3O_5S_2$ | M + Na | 554 |

Example 134

1-(4-Acetyl-piperazin-1-yl)-2-[2-(4-methoxy-phenylamino)-phenylmethanesulfinyl]-ethanone Compound I wherein Ar is 4-$OCH_3$Ph, X is NH, q is 1, substitution in ortho postion, $R^2$ and $R^3$ are H, Y—$R^1$ is $CH_2CO$-1-(4-acetyl)-piperazinyl.

To a stirred mixture of 4-methoxyphenyl boronic acid (1 g; 6.6 mmol), myristic acid (0.3 g; 1.3 mmol) and copper(II) acetate anhydrous (0.12 g; 0.66 mmol) in $CH_2Cl_2$ (10 mL) were added compound 19 (1.4 g; 4.3 mmol) in $CH_2Cl_2$ (10 mL) and 2,6-lutidine (0.52 mL; 4.5 mmol). The reaction mixture was stirred for two days. The catalyst was removed by filtration on a pad of Celite, and the filtrate was evaporated. The resulting residue was purified by column chromatography (eluent: methylenechloride/methanol 96/4) to generate Example 134 as a beige powder.

Yield: 49 g; 2.1 mmol).

$R_f$=0.49 (eluent: 9:1 methylenechloride/methanol).

$^1$H-NMR (DMSO-$d_6$) δ: 7.70 (s, 1H), 7.20-7.10 (m, 2H), 7.05 (broad d, 1H), 6.90 (broad d, 2H), 6.85-6.70 (m, 3H), 4.30 (broad dd, 1H), 4.20 (broad d, 1H), 4.05 (broad m, 2H), 3.50 (broad, 8H), 2.00 (s, 3H).

MS: 452 (M+Na).

Examples 135 trough 141 were prepared following the same multistep general method as desribed for Example 134 utilizing the appropriate substituted amine —NR$^{12}$R$^{13}$ and the appropriate substituted boronic acid in step 4. The analytical data is presented by each compounds molecular formula and masse spectrum (M+H) or (M+Na) as shown in the following Table 5.

TABLE 5

| Example N° | Molecular Formula | Peak | Mass |
|---|---|---|---|
| 135 | $C_{21}H_{25}N_3O_3S$ | M + Na | 422 |
| 136 | $C_{21}H_{25}N_3O_3S$ | M + Na | 422 |
| 137 | $C_{22}H_{27}N_3O_4S$ | M + Na | 452 |
| 138 | $C_{21}H_{24}FN_3O_3S$ | M + Na | 440 |
| 139 | $C_{21}H_{24}ClN_3O_3S$ | M + Na | 456 |
| 140 | $C_{21}H_{24}FN_3O_3S$ | M + Na | 440 |
| 141 | $C_{21}H_{23}Cl_2N_3O_3S$ | M + Na | 490 |

Example 142

Thiophene-2-carboxylic acid {2-[2-(4-acetyl-piperazin-1-yl)-2-oxo-ethanesulfinylmethyl]-phenyl}-amide Compound I wherein Ar is 2-Thienyl, X is CONH, q is 1, substitution in ortho postion, R$^2$ and R$^3$ are H, Y—R$^1$ is CH$_2$CO-1-(4-acetyl)-piperazinyl.

To a stirred solution of compound 19 (1 g; 3.1 mmol) in CH$_2$Cl$_2$ (30 mL), pyridine (0.5 mL; 6.2 mmol) and 2-thiophenecarbonyl chloride (0.46 g; 3.1 mmol) were added. The reaction mixture was stirred for twelve hours and then, methylene chloride (100 mL) were added into it. The resulting mixture was washed with an aqueous hydrochloric acid solution 1N (2×100 mL) and evaporated. The resulting residue was purified by column chromatography (eluent: methylenechloride/methanol 9/1) to generate Example 142 as a white powder.

Yield: 86% (1.16 g; 2.7 mmol).

$R_f$=0.50 (eluent: 9:1 methylenechloride/methanol).

$^1$H-NMR (DMSO-$d_6$) δ: 10.55 (s, 1H), 7.80 (broad d, 2H), 7.75 (broad d, 1H), 7.45-7.30 (m, 2H), 7.25-7.15 (m, 2H), 4.45 (broad, 2H), 4.20-4.00 (broad m, 2H), 3.50-3.40 (broad, 8H), 2.0 (s, 3H).

MS: 456 (M+Na).

Example 143 was prepared following the same multistep general method as described for Example 142 utilizing the appropriate substituted amine —NR$^{12}$R$^{13}$ and the appropriate carbonyl chloride in step 4. The molecular formula and masse spectrum (M+H) or (M+Na) are presented for Example 143 in Table 6.

TABLE 6

| Example N° | Molecular Formula | Peak | Mass |
|---|---|---|---|
| 143 | $C_{20}H_{23}N_3O_5S$ | M + Na | 440 |

Example 144

1-(4-acetyl-piperazin-1-yl)-2-{2-[(thiophen-2-ylmethyl)-amino]-phenylmethanesulfinyl}-ethanon Compound I wherein Ar is 2-thienyl, X is CH$_2$NH, q is 1, substitution in ortho postion, R$^2$ and R$^3$ are H, Y—R$^1$ is CH$_2$CO-1-(4-acetyl)-piperazinyl.

To a cooled solution of compound 19 (0.65 g; 2 mmol) in 1,2-dichloroethane (10 mL), 2-thiophene carboxaldehyde (0.29 g; 2.6 mmol), sodium triacetoxy borohydride (0.57 g; 2.7 mmol) and acetic acid (0.15 mL) were added. The reaction mixture was stirred under nitrogen for three hours and then, ethylacetate (100 mL) were added into it. The resulting mixture was washed with an aqueous sodium hydrogenocarbonate (1×100 mL), aqueous solution (1×100 mL) and evaporated. The resulting residue was purified by column chromatography (eluent: methylenechloride/methanol 9/1) to generate Example 144 as a white powder.

Yield: 71% (0.6 g; 1.4 mmol).

$R_f$=0.45 (eluent: 9:1 methylenechloride/methanol).

$^1$H-NMR (DMSO-$d_6$) δ: 7.40 (broad d, 1H), 7.20-7.00 (m, 3H), 6.85-6.95 (broad m, 1H), 6.7-6.6 (broad m, 2H), 6.30 (broad, 1H), 4.50 (broad d, 1H), 4.30 (broad d, 1H), 4.20-4.00 (broad m, 3H), 3.55-3.45 (broad, 8H), 2.00 (s, 3H).

MS: 442 (M+Na).

Example 145 was prepared following the same multistep general method as described for Example 144 utilizing the appropriate substituted amine —NR$^{12}$R$^{13}$ and the appropriate aldehyde in step 4. The molecular formula and masse spectrum (M+H) or (M+Na) is presented for Example 145 in Table 7.

TABLE 7

| Example N° | Molecular Formula | Peak | Mass |
|---|---|---|---|
| 145 | $C_{20}H_{25}N_3O_4S$ | M + Na | 426 |

Example 146

1-(4-acetyl-piperazin-1-yl)-2-[2-(3,4-dichloro-benzylamino)-phenylmethanesulfinyl]-ethanone Compound I wherein Ar is 3,4-DiClPh, X is CH$_2$NH, q is 1, substitution in ortho postion, R$^2$ and R$^3$ are H, Y—R$^1$ is CH$_2$CO-1-(4-acetyl)-piperazinyl.

To a stirred solution of compound 19 (1 g; 3.1 mmol) in DMF (25 mL), diisopropylethylamine (0.6 mL; 3.4 mmol) and 3,4-dichlorobenzyl bromide (0.74 g; 3.1 mmol) were added. The reaction mixture was stirred for twelve hours and then, ethylacetate (250 mL) were added into it. The resulting mixture was washed with brine (2×200 mL) and evaporated. The resulting residue was purified by column chromatography (eluent: methylenechloride/methanol 9/1) to generate Example 146 as a white powder.

Yield: 51% (0.76 g; 1.6 mmol).

$R_f$=0.47 (eluent: 9:1 methylenechloride/methanol).

$^1$H-NMR (DMSO-d$_6$) δ: 7.70 (broad s, 1H), 7.60 (broad d, 1H), (broad m, 1H), 7.4 (broad d, 1H), 7.10 (broad m, 2H), 6.6 (broad t, 1H), 6.5 (broad d, 1H), 6.3 (broad m, 1H), 4.4-4.3 (broad m, 3H), 4.2-4.0 (broad, 3H), 3.55-3.35 (broad, 8H), 2.0 (s, 3H).

MS: 504 (M+Na).

Examples 147 through 149 were prepared following the same multistep general method as described for Example 146 utilizing the appropriate substituted amine —NR$^{12}$R$^{13}$ and the appropriate benzyl halide in step 4. The molecular formula and masse spectrum (M+H) or (M+Na) are presented for each Examples in Table 8.

TABLE 8

| Example N° | Molecular Formula | Peak | Mass |
|---|---|---|---|
| 147 | C$_{22}$H$_{26}$FN$_3$O$_3$S | M + Na | 454 |
| 148 | C$_{22}$H$_{25}$Cl$_2$N$_3$O$_3$S | M + Na | 504 |
| 149 | C$_{22}$H$_{26}$FN$_3$O$_3$S | M + Na | 454 |

Example 149a

Compound I wherein Ar is 3,4-DiClPhenyl, X is CONH, q is 1, substitution in para position, R$^2$ and R$^3$ are H, Y—R$^1$ is CH$_2$ CO NH$_2$.

To a stirred solution of compound 19a (0.7 g; 3.3 mmol) in CH$_2$Cl$_2$ (30 mL) were added pyridine (0.53 mL; 6.6 mmol) and 3,4-dichlorobenzoylchloride (0.69 g; 3.3 mmol). The reaction mixture was stirred for eight days and filtered. The resulting solid was washed with water, ethyl acetate and ethanol, then dried under vacuum to give Example 149a as a yellow solid.

Yield: 59% (0.75 g; 1.9 mmol).

$^1$H-NMR (DMSO-d$_6$) δ: 10.5 (s, 1H), 8.25 (broad s, 1H), 7.9 (broad d, 1H), 7.8 (broad d, 1H), 7.75 (broad d, 2H), 7.7 (broad s, 1H), 7.3 (broad m, 3H), 4.25 (d, 1H), 4.0 (d, 1H), 3.6 (d, 1H), 3.45 (d, 1H).

MS:407 (M+Na).

III-Compounds Prepared According to Scheme D.

Examples 150 to 153 were synthesized according to Scheme D.

A-Preparation of Compound I

Example 150

Compound I wherein Ar is Ph, X is OCH$_2$, q is 0, substitution in ortho postion, R$^2$ and R$^3$ are H, Y—R$^1$ is CH$_2$COOMe.

A mixture of α,α'-dibromo-o-xylene (7.15 g, 27.1 mmol), methyl glycolate (2.87 g, 27.1 mmol) and K$_2$CO$_3$ (8.25 g, 59 mmol) in DMF (dry, 20 mL) was stirred under argon at room temperature for 4 h. Phenol (2.54 g, 27 mmol) was added to the reaction mixture and stirring was continued overnight. The reaction mixture was filtered and the residue was washed several times with EtOAc. Combined filtrate and washings were washed successively with 0.5N NaOH, water (twice) and brine, dried (magnesium sulfate), and concentrated to generate a crude product. It was purified by flash chromatography (eluent:hexane/ethyl acetate 85/15) to generate example 150 as a viscous oil.

Yield=18% (1.48 g; 4.9 mmol).

$^1$H-NMR (CDCl$_3$): δ7.74-6.81 (a series of m, 9H), 5.20 (s, 2H), 3.96 (s, 2H), 3.66 (s, 3H), 3.31 (s, 2H).

MS: m/e 325 (M+Na).

Example 151

Compound I wherein Ar is Ph, X is OCH$_2$, q is 0, substitution in ortho postion, R$^2$ and R$^3$ are H, Y—R$^1$ is CH$_2$COOH.

A mixture of Example 150 (1.48 g, 4.9 mmol), 1N NaOH (25 mL) and methanol (25 mL) was kept under reflux for 4 h (the mixture became homogenous), cooled, concentrated, and diluted with water. It was then neutralized with conc. HCl. and extracted into ethyl acetate (twice). Combined organic layer was washed with water and brine, dried (MgSO$_4$) and concentrated to generate Example 151 as a viscous oil that was directly used in the next step.

Yield=88% (1.25 g; 4.34 mmol).

$^1$H-NMR (CDCl$_3$): δ7.82-6.80 (a series of m, 9H), 5.20 (s, 2H), 3.98 (s, 2H), 3.14 (s, 2H).

Example 152

Compound I wherein Ar is Ph, X is OCH$_2$, q is 0, substitution in ortho postion, R$^2$ and R$^3$ are H, Y—R$^1$ is CH$_2$COONH$_2$.

A mixture of Example 151 (1.25 g, 4.34 mmol), HOBt.NH$_3$ complex (1.45 g, 9.53 mmol), TBTU (1.70 g, 5.29 mmol) in DMF (15 mL) was stirred at room temperature overnight. It was then diluted with dichloromethane and successively washed with water, 2% citric acid, water, 2% NaHCO$_3$, water and brine, dried (MgSO$_4$), and concentrated to generate a crude product. It was purified by flash chromatography (eluent:hexane/ethyl acetate 1/4) to generate Example 152.

Yield=67% (0.83 g; 2.89 mmol).

$^1$H-NMR (CDCl$_3$): δ7.74-6.96 (a series of m, 9H), 6.52 (br s, 1H), 5.39 (br s, 1H), 5.16 (s, 2H), 3.89 (s, 2H), 3.14 (s, 2H).

Example 153

2-(2-phenoxymethyl-phenylmethanesulfinyl)-acetamide

Compound I wherein Ar is Ph, X is OCH$_2$, q is 1, substitution in ortho postion, R$^2$ and R$^3$ are H, Y—R$^1$ is CH$_2$COONH$_2$.

To a solution of Example 152 (0.82 g, 2.87 mmol) in acetic acid (10 mL) was added hydrogen peroxide (50% in water, 200 μL). The reaction mixture was stirred at room temperature for 4 h, neutralized (carefully) with aq. Na HCO$_3$ solution and extracted into ethyl acetate (twice). Combined organic layer was washed with brine, dried (MgSO$_4$) and concentrated to give a crude product that was purified by flash chromatography (eluent dichloromethane/MeOH 93/7) to generate Example 153.

Yield=70% (0.61 g; 2.01 mmol).

m.p.: 153-154° C.

$^1$H-NMR (DMSO-d$_6$): δ7.71 (s, 1H), 7.52(s, 1H), 7.37-6.93 (a series of m, 9H), 5.21 (s, 2H), 4.39 (d, 1H), 4.17(d, 1H), 3.77 (d, 1H), 3.55 (d, 1H).

MS: 326 (M +Na),

BIOLOGICAL DATA

Methodology: Evaluation of Wake Promoting Activity in Rats

The methodology utilized for evaluating wake promoting activity of test compounds is based on that described by Edgar and Seidel, *Journal of Pharmacology and Experimental Therapeutics*, 283:757-769, 1997, and incorporated herein in its entirety by reference.

Animal Surgery. Adult, male Wistar rats (275-320 g from Charles River Laboratories, Wilmington, Mass.) were anesthetized (Nembutal, 45 mg/kg, ip.) and surgically prepared with implants for recording of chronic EEG (encephalographic) and EMG (electromyographic) recording. The EEG implants were made from commercially available components (Plastics One, Roanoke, Va.). EEG signals were recorded from stainless steel screw electrodes: 2 frontal (+3.0 mm AP from bregma, ±2.0 mm ML), and 2 occipital (−4.0 mm AP from bregma, ±2.0 mm ML). Two Teflon-coated stainless steel wires were positioned under the nuchal trapezoid muscles for EMG recording. All electrode leads were inserted into a connector pedestal and the pedestal affixed to the skull by application dental acrylic. Antibiotic was administered post surgically and antibiotic cream was applied to the wound edges to prevent infection. At least one week elapsed between surgery and recording.

Recording environment. Postsurgically, rats were housed in pairs in an isolated room. Food and water were available ad libitum, ambient temperature was 21° C., and humidity was 55%. At least 24 hrs prior to recording, they were placed in Nalgene containers (31×31×31 cm) with a wire-grid top, and entry to the room was prohibited during the day of recording except for dosing. The containers were placed on a rack with two shelves, 4 containers per shelf. Fluorescent overhead room lights were set to a 24 hr. light/dark cycle (on at 7 AM, off at 7 PM). Light levels inside the containers were 38 and 25 lux for the top and bottom shelves respectively. Background white-noise (68 db inside the containers) was present in the room to mask ambient sounds.

Data acquisition. EEG and EMG signals were led via cables to a commutator (Plastics One) and then to pre-amplifiers (model 1700, A-M Systems, Carlsborg, Wash.). EEG and EMG signals were amplified (10K and 1K respectively) and bandpass filtered between 0.3 and 500 Hz for EEG and between 10 and 500 Hz for EMG. These signals were digitized at 128 samples per second using ICELUS sleep research software (M. Opp, U. Texas; see Opp, Physiology and Behavior 63:67-74, 1998, and Imeri, Mancia, and Opp, *Neuroscience* 92:745-749, 1999, incorporated by reference herein in their entirety) running under Labview 5.1 software and data acquisition hardware (PCI-MIO-16E-4; National Instruments, Austin, Tex.). On the day of dosing, data was recorded for 6 to 10 hours beginning at 11 AM.

Drug administration and study design. Compounds were evaluated on groups of from 4 to 8 rats carried out over one or two separate test sessions. Each animal was tested with a different compound or vehicle for up to 10 weeks with at least 7 days between successive tests. A vehicle group was included in all experiments, and each animal received vehicle every 4$^{th}$ test. Test compounds were suspended in sterile 0.25% methylcellulose (pH=6.2; Upjohn Co., Kalamazoo, Mich.) at 30 mg/mL. Although compounds can be administered at dosages greater than 100 mg/kg and are expected to be active under the selection criteria of data analysis, unless otherwise noted, compounds were administered at a single dose of 100 mg/kg. Dosing was carried out at noon, while the rats were predominantly asleep. Each rat was lifted out of its container, given an intraperitoneal injection in a volume of 5 mL/kg, and replaced. Dosing required approximately 30 sec per rat.

Sleep/wake scoring. Sleep and wake activity were determined manually using ICELUS software. This program displays the EEG and EMG data in blocks of 6 sec along with the EEG frequency spectrum. Arousal state was scored as awake, rapid eye-movement (REM), or slow-wave or non-REM sleep (NREM) according to visual analysis of EEG frequency and amplitude characteristics and EMG activity (Opp and Krueger, 1994; Van Gelder, et al., 1991; Edgar, et al., 1991, 1997; Seidel, et al, 1995, incorporated by reference herein in their entirety). Essentially, waking activity consists of relatively low-amplitude EEG activity with relatively lower power in the frequency band from 0.5-6 Hz, accompanied by moderate to high level EMG activity. In a particular waking state ("theta-waking"), EEG power can be relatively focused in the 6-9 Hz (theta) range, but significant EMG activity is always present. NREM sleep is characterized by relative high-amplitude EEG activity with relatively greater power in the low frequency band from 0.5-6 Hz, accompanied by little or no EMG activity. REM sleep is characterized by moderate and constant amplitude EEG focused in the theta (6-9 Hz) range, similar to waking theta, but with no EMG activity.

Data analysis and statistics. Two basic outcome measures were used to ascertain whether a compound exhibited wake-enhancing activity. The first was the percent time spent awake for each 30 min period following dosing. The second was the total time spent awake in the first 3 hrs following dosing (3 hr AUC; maximum 180 min). For purposes of ascertaining activity of a test compound, wake activity values were compared against corresponding vehicle values. The vehicle values were of two types. The first type was the corresponding within-experiment vehicle, that is, a value for the vehicle group run concurrently with the test compound. A second "reference" vehicle value consisted of the mean 3 hr AUC value calculated from 234 animals in 59 separate experiments carried out during the same time period as the evaluations of the test compounds (mean ±SD =69.22±20.12; 95% confidence limits=66.63-71.81). Two-tailed, unpaired t-tests were performed on the wake time values for drug versus vehicle treated animals, and compounds with $p \leq 0.05$ were deemed significantly wake-promoting. A test compound was considered "active" if it met one of the following three criteria:

(i) The 3 hr AUC value for the test compound was significantly greater ($p \leq 0.05$) than the mean wake value for the reference vehicle group (N=234).

(ii) The 3 hr AUC value for the test compound was significantly greater ($p \leq 0.05$) than the corresponding value for the vehicle group within the same experiment.

(iii) One or more of the half-hour wake time values from 0.5 to 2 hrs after dosing was significantly greater ($p \leq 0.05$) in the test compound group than in the corresponding vehicle group within the same experiment.

Results

Compounds of the invention either have demonstrated or are expected to demonstrate utility for wake promoting activity.

As example, the three-hours AUC value (mean±sem) for the reference vehicle group and for the test compounds are reported Table 9 for Examples 22, 40 and 113. These test compounds were administered by i.p. route at a 100 mg/kg dose and the time-course of the percent of time awake as function of time was estimated from 1 hr prior to 5 hours post dosing.

TABLE 9

Mean $AUC_{0-3h}$ values (± sem) for the reference vehicle group and for test compounds

| | Vehicle | | Test compound | | |
|---|---|---|---|---|---|
| | Mean | sem | Mean | sem | p |
| Example 22 | 67.1 | 5.3 | 162.7 | 6.5 | 0.000 |
| Example 40 | 66.9 | 5.5 | 118.9 | 10.6 | 0.001 |
| Example 113 | 63.5 | 9.1 | 99.0 | 10.4 | 0.022 |

$AUC_{0-3h}$ (% of waiking time × hr) – n = 8 Rats per test compound and 8 rats per control groups.

As compared to the control groups, compounds of Example 22, 40 and 113 produced a significantly greated wakefulness than that observed in the vehicle-treated animals ($p<0.05$).

References

The following references, to the extent that they provide exemplary procedural or other details supplementary to those set forth herein, are specifically incorporated in their entirety herein by reference:

Touret, et al., *Neuroscience Letters*, 189:43-46, 1995.
Van Gelder, R. N. et al., *Sleep* 14:48-55, 1991.
Edgar, D. M., *J. Pharmacol. Exp. Ther*. 282:420-429, 1997.
Edgar and Seidel, *J. Pharmacol. Exp. Ther*., 283:757-69, 1997.
Hernant et al., *Psychopharmacology*, 103:28-32, 1991.
Lin et al., *Brain Research*, 591:319-326, 1992.
Opp and Krueger, *American Journal of Physiology* 266: R688-95, 1994
Panckeri et al., *Sleep*, 19(8):626-631, 1996.
Seidel, W. F., et al., *J. Pharmacol. Exp. Ther*. 275:263-273, 1995.
Shelton et al., *Sleep* 18(10):817-826, 1995.
Welsh, D. K., et al., *Physiol. Behav*. 35:533-538, 1985.

Utility

The present invention provides a method of treating diseases and conditions in a subject in need thereof comprising administering to said subject a therapeutically effective amount of a compound of formula (I). For example, the compounds of the present invention are use in the treatment of diseases, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder ("ADHD"), enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

Dosage and Formulation

The compounds of the present invention can be administered for therapeutic purposes by any means that results in the contact of the active agent with the agent's site of action in a subject. The compounds may be administered by any conventional means available for use in conjunction with pharmaceuticals, either as individual therapeutic agents or in a combination with other therapeutic agents, such as, for example, analgesics, or in combination with antidepressants, including but are not limited to tricyclic antidepressants ("TCAs"), Selective Serotonin Reuptake Inhibitors ("SSRIs"), Serotonin and Noradrenaline Reuptake Inhibitors ("SNRIs"), Dopamine Reuptake Inhibitors ("DRIs"), Noradrenaline Reuptake Inhibitors ("NRUs"), Dopamine, Serotonin and Noradrenaline Reuptake Inhibitors ("DSNRIs") and Monoamine Oxidase Inhibitors ("MAOIs") including reversible inhibitors of monoamine oxidase type A (RIMAs). The compounds of the present invention are preferably administered in therapeutically effective amounts for the treatment of the diseases and disorders described herein.

A therapeutically effective amount can be readily determined by the attending diagnostician, as one skilled in the art, by the use of conventional techniques. The effective dose will vary depending upon a number of factors, including the pharmacodynamics of the active agent, the type and extent of progression of the disease or disorder, the age, weight and health of the particular patient, the formulation of the active and its mode and frequency of administration, and the desired effect with a minimization of side effects. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A typical daily dose for adult humans can range from about 1 to about 1000 mg of the active agent, particularly from about 1 to about 400 mg, and including 25, 50, 85, 100, 150, 170, 200, 255, 250, 255, 340, 400, 425, 500, 600, 700, 750, 800, and 900 mg doses, and equivalent doses for a human child.

The compounds may be administered in one or more unit dose forms, and they may be administered in a single daily dose or in two, three or four doses per day. The unit dose ranges from about 1 to about 1000 mg, particlularly from about 1 to about 400 mg, and including 25, 50, 85, 100, 150, 170, 200, 255, 250, 255, 340, 400, 425, 500, 600, 700, 750, 800, and 900 mg unit doses, and equivalent unit doses for a human child. In particular, the unit dosages range from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The active agent may be present in about 0.5-95% by weight of the composition. The excipients are selected on the basis of the chosen route of administration and standard pharmaceutical practice, as described, for example, in *Remington: The Science and Practice of Pharmacy*, 20$^{th}$ ed.; Gennaro, A. R., Ed.; Lippincott Williams & Wilkins: Philadelphia, Pa., 2000.

The compositions can be prepared for administration by oral means, including tablets, pills, powders, capsules, troches and the like; parenteral means, including intravenous, intramuscular, and subcutaneous means; topical or transdermal means, including patches, creams, ointments, lotions, pastes, gels, solutions, suspensions, aerosols, and powders and the like; transmucosal means, including nasal, rectal, vaginal, sublingual and buccal means; ophthalmic or inhalation means. Preferably the compositions are prepared for oral administration, particularly in the form of tablets, capsules or syrups; parenteral administration, particularly in the form of liquid solutions, suspensions or emulsions; intranasal administration, particularly in the form of powders, nasal drops, or aerosols; or for topical use, such as patches, creams, ointments, and lotions.

For oral administration, the tablets, pills, powders, capsules, troches and the like can contain one or more of the following: diluents or fillers such as starch, or cellulose; binders such as microcrystalline cellulose, gelatins, or polyvinylpyrrolidone; disintegrants such as starch or cellulose derivatives; lubricants such as talc or magnesium stearate; glidants such as colloidal silicon dioxide; sweetening agents such as sucrose or saccharin; and flavoring agents such as peppermint or cherry flavoring. Capsules may contain any of the above ingredients, and may also contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers; suspending agents; thickening agents; and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

The compositions of the present invention may be formulated to control and/or delay the release of the active agent(s). Such controlled-, delayed, sustained-, or extended-release compositions are well-known in the art, and may include, for example, reservoir or matrix diffusion products, as well as dissolution systems. Some compositions may utilize, for example biocompatible, biodegradable lactide polymer, lactide/glycolide copolymer, or polyoxyethylene-polyoxypropylene copolymers as excipients.

Preferred embodiments of the invention include the following:

1. A compound of formula (A):

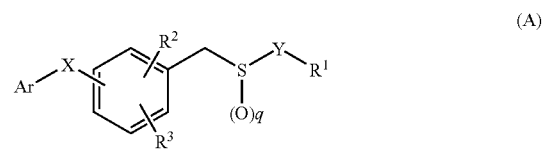

(A)

wherein:

Ar is independantly selected from $C_6$-$C_{10}$ aryl and 5 to 10-membered heteroaryl wherein:
  $C_6$-$C_{10}$ aryl and heteroaryl are optionally substituted with one to three groups selected from F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

X is O, $S(O)_y$, $N(R^{10})$, $OC(R^{22})_2$, $(R^{22})_2CO$, $C(R^{22})_2NR^{21}$, $NR^{21}C(R^{22})_2$, $C(=O)N(R^{21})$, $NR^{21}C(=O)$, $S(O)_2$—$NR^{22}$, $NR^{22}S(O)_2$, $C(R^{22})_2C(R^{22})_2$, $CR^{21}=CR^{21}$, $C\equiv C$;

Y is $C_1$-$C_6$ alkylene; or
  $(C_1$-$C_4$ alkylene$)_m$—Z—$(C_1$-$C_4$ alkylene$)_n$;
wherein said alkylene groups are optionally substituted with one to three $R^{20}$ groups;

Z is O, $NR^{10A}$, $S(O)_y$, $CR^{21}=CR^{21}$, $C\equiv C$, $C_6$-$C_{10}$ arylene, 5-10 membered heteroarylene, $C_3$-$C_6$ cycloalkylene, or 3-6 membered heterocycloalkylene; wherein said arylene, heteroarylene, cycloalkylene, and heterocycloalkylene groups are optionally substituted with one to three $R^{20}$ groups;

$R^1$ is selected from $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;
  wherein said aryl groups are optionally substituted with one to three $R^{20}$ groups;

$R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(O)NR^{23}R^{24}$, $NR^{21}C(=S)R^{22}$, and $S(O)_yR^{22}$;

$R^{10}$ and $R^{10A}$ are each independently selected from H, $C_1$-$C_6$ alkyl, $C_6$-$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_3$-$C_7$ alkyl and $C_6$-$C_{10}$ aryl;
  wherein said alkyl and aryl group are optionally substituted with one to three $R^{20}$ groups;

$R^{12}$ and $R^{13}$ at each occurrence are each independently selected from H, $C_1$-$C_6$ alkyl, or $R^{12}$ and $R^{13}$, together with the nitrogen to which they are attached, form a 3-7 membered heterocyclic ring;

wherein said alkyl group and heterocyclic ring are optionally substituted with one to three $R^{20}$ groups;

$R^{14}$ at each occurrence is independently selected from $C_1$-$C_6$ alkyl, $C_6$-$C_{10}$ aryl, and arylalkyl;
wherein said alkyl, aryl and arylalkyl groups are optionally substituted with one to three $R^{20}$ groups;

$R^{20}$ at each occurrence is independently selected from F, Cl, Br, I, $OR^{22}$, $OR^{25}$, $NR^{23}R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_qR^{22}$;

$R^{21}$ at each occurrence is independently selected from H and $C_1$-$C_6$ alkyl;

$R^{22}$ at each occurrence is independently selected from H, $C_1$-$C_6$ alkyl, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring;

$R^{25}$ at each occurrence is independently the residue of an amino acid after the hydroxyl group of the carboxyl group is removed;

m is 0 or 1;
n is 0 or 1;
q is 0, 1, or 2;
y is 0, 1, or 2;

with the exclusion of the compounds wherein:
Y is $C_2$ alkylene substituted with one to three $C_1$-$C_6$ alkylene and/or $NR^{23}R^{24}$ and/or $NR^{21}CO_2R^{22}$; and
$R^1$ is $C(=O)NR^{12}R^{13}$.

and with the exclusion of the compound:
tetrahydro-2-[[{4-(phenylthio)phenyl]methyl}thio] acetyl]-2H-1,2-oxazine;

and the stereoisomeric forms, mixtures of stereoisomeric forms or pharmaceutically acceptable salts forms thereof.

2. The compound according to embodiment 1, wherein:
Y is $C_1$-$C_6$alkylene;
$(C_1$-$C_4$ alkylene$)_m$—$Z^1$—$(C_1$-$C_4$ alkylene$)_n$;
$C_1$-$C_4$ alkylene-$Z^2$—$C_1$-$C_4$ alkylene;
wherein said alkylene groups are optionally substituted with one to three $R^{20}$ groups;

$Z^1$ is $CR^{21}=CR^{21}$, C≡C, $C_6$-$C_{10}$ arylene, 5-10 membered heteroarylene,
$C_3$-$C_6$ cycloalkylene, or 3-6 membered heterocycloalkylene;
wherein said arylene, heteroarylene, cycloalkylene, and heterocycloalkylene groups are optionally substituted with one to three $R^{20}$ groups;

$Z^2$ is O, $NR^{10A}$, or $S(O)_y$.

3. The embodiment according to any of claims 1 or 2 wherein q is 1.

5. The compound according to any of embodiments 1 to 3 wherein $R^1$ is selected from $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$.

6. The compound according to embodiment 5 wherein $R^1$ is selected from $NR^{12}R^{13}$; $NR^{21}C(=O)R^{14}$; $C(=O)NR^{12}R^{13}$; $C(=NR^{11})NR^{12}R^{13}$; and $NR^{21}C(=O)NR^{12}R^{13}$.

7. The compound according to embodiment 6 wherein $R^1$ is $C(=O)NR^{12}R^{13}$.

8. The compound according to any of the embodiments 5 to 7 wherein $R^{12}$ and $R^{13}$ are each independently selected from H and $C_1$-$C_6$ alkyl.

9. The compound according to any of the embodiments 5 to 7 wherein $R^{12}$ and $R^{13}$ together with the nitrogen to which they are attached, form a 3-7 membered heterocyclic ring, wherein said heterocyclic ring is optionally substituted with one $R^{20}$ group.

10. The compound according to embodiment 5 wherein $R^1$ is selected from $C(=O)R^{14}$, $CO_2R^{11}$, $OC(=O)R^{11}$, $C(=O)NR^{12}R^{13}$, $OC(=O)NR^{12}R^{13}$, $NR^{21}S(O)_2R^{11}$, and $NR^{21}S(O)_2NR^{12}R^{13}$.

11. The compound according to embodiments 1 to 10 wherein X is O, $S(O)_y$, $N(R^{10})$.

12. The compound according to embodiments 1 to 10 wherein X is $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2NR^{22}$, $NR^{22}S(O)_2$, $C(R^{22})_2C(R^{22})_2$.

13. The compound according to embodiment 12 wherein X is $OC(R^{22})_2$, $C(R^{22})_2NR^{21}$, $C(=O)N(R^{21})$, $S(O)_2$—$NR^{22}$.

14. The compound according to any of embodiments 1 to 13 wherein Y is $C_1$-$C_6$ alkylene.

15. The compound according to embodiment 14 wherein Y is $CH_2$.

16. The compound according to any of embodiments 2 to 13 wherein Y is $(C_1$-$C_4$ alkylene$)_m$—$Z^1$—$(C_1$-$C_4$ alkylene$)_n$.

17. The compound according to embodiment 16 wherein $Z^1$ is $C_6$-$C_{10}$ arylene or $C_3$-$C_6$ cycloalkylene.

18. The compound according to embodiment 17 wherein $Z^1$ is phenylene.

19. The compound according to embodiment 16 wherein $Z^1$ is 5-10 membered heteroarylene or 3-6 membered heterocycloalkylene.

20. The compound according to embodiment 16 wherein $Z^1$ is $CR^{21}=CR^{21}$ or C≡C.

21. The compound according to any of embodiments 2 to 13 wherein Y is $C_1$-$C_4$ alkylene-$Z^2$—$C_1$-$C_4$ alkylene.

22. The compound according to embodiment 21 wherein $Z^2$ is O.

23. The compound according to embodiments 1 or 2 with the structure:

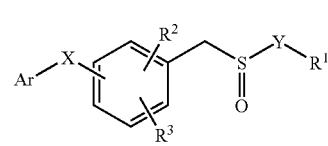

(Ia)

wherein:
Ar is independantly selected from $C_6$-$C_{10}$ aryl and 5 to 10-membered heteroaryl wherein:
$C_6$-$C_{10}$ aryl and heteroaryl are optionally substituted with one to three groups selected from F, Cl, Br, I, $OR^{22}$, $OR^{25}$, $NR^{23}R^{24}$, NHOH, $NO_2$, CN, $C_1$-$C_6$ alkyl, phenyl, arylalkyl, and $C(=O)R^{22}$;

X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2NR^{22}$, $NR^{22}S(O)_2$;

Y is $C_1$-$C_6$ alkylene;
$C_1$-$C_4$ alkylene-$Z^1$—$(C_1$-$C_4$ alkylene$)_n$; or
$C_1$-$C_4$ alkylene-$Z^2$—$C_1$-$C_4$ alkylene;
wherein said alkylene groups are optionally substituted with one to three $R^{20}$ groups;

$Z^1$ is $CR^{21}=CR^{21}$, C≡C, $C_6$-$C_{10}$ arylene, 5-10 membered heteroarylene,
$C_3$-$C_6$ cycloalkylene, or 3-6 membered heterocycloalkylene;

$Z^2$ is O, $NR^{10A}$, or $S(O)_y$;

$R^1$ is selected from $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;

$R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, phenyl, 5 or 6 membered heteroaryl, arylalkyl, $C(=O)R^{22}$;

$R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, phenyl, 5 or 6 membered heteroaryl, arylalkyl, $C(=O)R^{22}$;

$R^{10}$ and $R^{10A}$ are each independently selected from H, $C_1$-$C_6$ alkyl, $C(=O)R^{14}$, and $S(O)_yR^{14}$;
  wherein said alkyl groups are optionally substituted with one to three $R^{20}$ groups;

$R^{11}$ at each occurrence is independently selected from H or $C_3$-$C_7$ alkyl, wherein said alkyl group is optionally substituted with one to three $R^{20}$ groups;

$R^{12}$ and $R^{13}$ at each occurrence are each independently selected from H, and $C_1$-$C_6$ alkyl, or $R^{12}$ and $R^{13}$, together with the nitrogen to which they are attached, form a 3-7 membered heterocyclic ring;
  wherein said alkyl group and heterocyclic ring are optionally substituted with one to three $R^{20}$ groups;

$R^{14}$ at each occurrence is independently selected from $C_1$-$C_6$ alkyl, $C_6$-$C_{10}$ aryl, and arylalkyl;
  wherein said alkyl, aryl and arylalkyl groups are optionally substituted with one to three $R^{20}$ groups;

$R^{20}$ at each occurrence is independently selected from F, Cl, Br, I, $OR^{22}$, $OR^{25}$, $NR^{23}R^{24}$, NHOH, $NO_2$, CN, $CF_3$, phenyl, benzyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from H, $C_1$-$C_6$ alkyl, and $C_6$-$C_{10}$ aryl;

$R^{23}$ and $R^{24}$ at each occurrence are each independently selected from H, and $C_1$-$C_6$ alkyl, or $R^{23}$ and $R^{24}$, together with the nitrogen to which they are attached, form a 3-7 membered heterocyclic ring;

$R^{25}$ at each occurrence is independently the residue of an amino acid after the hydroxyl group of the carboxyl group is removed;

n is 0 or 1;
y is 0, 1, or 2;

and the stereoisomeric forms, mixtures of stereoisomeric forms or pharmaceutically acceptable salts forms thereof.

24. The compound according to embodiment 23 wherein:

Y is $C_1$-$C_6$ alkylene, $C_1$-$C_4$ alkylene-$Z^1$—$C_1$-$C_4$ alkylene, or $C_1$-$C_4$ alkylene-$Z^2$-$C_1$-$c_4$ alkylene, wherein said alkylene groups are optionally substituted with one to three $C_1$-$C_6$ alkyl groups;

$Z^1$ is $CR^{21}=CR^{21}$, C≡C, or phenyl;

$Z^2$ is O, $NR^{10A}$, or $S(O)_y$;

X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2NR^{22}$, $NR^{22}S(O)_2$; and $R^1$ is selected from $NR^{21}C(=O)R^{14}$, $C(=O)R^{14}$, $CO_2R^{11}$, $OC(=O)R^{11}$, and $C(=O)NR^{12}R^{13}$.

25. The compound according to embodiment 24 wherein $R^1$ is $C(=O)NR^{12}R^{13}$.

26. The compound according to embodiment 25 having the structure of formula (Ib):

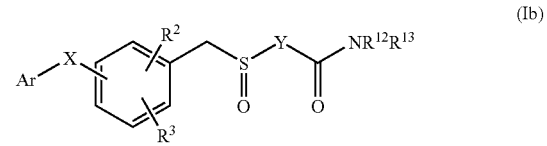

(Ib)

27. The compound according to embodiment 26 wherein X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2$—$NR^{22}$, $NR^{22}S(O)_2$.

28. The compound according to embodiment 27 wherein X is O, $S(O)_y$, NH.

29. The compound according to embodiment 27 wherein X is $OCH_2$, $CH_2O$, $CH_2NH$, $NHCH_2$, $C(=O)NH$, $NHC(=O)$, $S(O)_2NH$, $NHS(O)_2$.

30. The compound according to any of embodiments 27 wherein X is NH, O—$CH_2$, $CH_2NH$, $C(=O)NH$, $S(O)_2$—NH.

31. The compound according to any of emdodiments 1 to 30 wherein $R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, phenyl, 5 or 6 membered heteroaryl, arylalkyl, $C(=O)R^{22}$.

32. The compound according to any of embodiments 26 to 31 wherein Y is $C_1$-$C_6$ alkylene.

33. The compound according to embodiment 32 wherein Y is $CH_2$.

34. The compound according to any of embodiments 26 to 31 wherein Y is $(C_1$-$C_4$ alkylene$)_n$-$Z^1$—$C_1$-$C_4$ alkylene and $Z^1$ is phenyl, 5-6 membered heteroarylene, $CR^{21}=CR^{21}$, or C≡C.

35. The compound according to embodiment 1 selected in accordance with the following table, wherein:

TABLE 1

| Ex. n° | Ar | X | Position* | $R^2$ | $R^3$ | q | Y—$R^1$ |
|---|---|---|---|---|---|---|---|
| 13 | 3,4-DiClPh | O | para | H | H | 0 | $CH_2$CO-N-piperazinyl-N-Boc |
| 14 | 3,4-DiClPh | O | para | H | H | 0 | $CH_2$CO-N-piperazinyl |
| 19 | 3,4-DiClPh | O | para | H | H | 1 | $CH_2$CO-N-piperazinyl |

TABLE 1-continued $$\text{Ar}-X-\text{(benzene with } R^2, R^3\text{)}-CH_2-S(O)_q-Y-R^1$$

| Ex. n° | Ar | X | Position* | R² | R³ | q | Y—R¹ |
|---|---|---|---|---|---|---|---|
| 16 | 4-ClPh | S | para | H | H | 0 | CH₂CO-1-(4-acetyl)-piperazinyl |
| 23 | 4-ClPh | S | para | H | H | 1 | CH₂CO-1-(4-acetyl)-piperazinyl |
| 24 | 4-ClPh | SO | para | H | H | 1 | CH₂CO-1-(4-acetyl)-piperazinyl |
| 29 | Ph | O | para | H | H | 1 | CH₂CONHCHMe₂ |
|  | Ph | O | meta | H | H | 0 | CH₂CO-N-pyrrolidinyl |
| 31 | Ph | O | meta | H | H | 1 | CH₂CO-N-pyrrolidinyl |
|  | Ph | O | meta | H | H | 0 | CH₂CONH₂ |
| 32 | Ph | O | meta | H | H | 1 | CH₂CONH₂ |
|  | Ph | O | meta | H | H | 0 | CH₂CONMe₂ |
| 33 | Ph | O | meta | H | H | 1 | CH₂CONMe₂ |
|  | Ph | O | meta | H | H | 0 | CH₂CONHCHMe₂ |
| 34 | Ph | O | meta | H | H | 1 | CH₂CONHCHMe₂ |
|  | Ph | O | meta | H | H | 0 | CH₂CO-1-(4-acetyl)-piperazinyl |
| 35 | Ph | O | meta | H | H | 1 | CH₂CO-1-(4-acetyl)-piperazinyl |
|  | 4-OCH₃Ph | O | para | H | H | 0 | CH₂CONH₂ |
| 36 | 4-OCH₃Ph | O | para | H | H | 1 | CH₂CONH₂ |
|  | 4-OCH₃Ph | O | para | H | H | 0 | CH₂CO-1-(4-acetyl)-piperazinyl |
| 37 | 4-OCH₃Ph | O | para | H | H | 1 | CH₂CO-1-(4-acetyl)-piperazinyl |
|  | 4-OCH₃Ph | O | para | H | H | 0 | CH₂CO-N-piperazinyl |
| 38 | 4-OCH₃Ph | O | para | H | H | 1 | CH₂CO-N-piperazinyl |
|  | 3,4-DiClPh | O | para | H | H | 0 | CH₂CONH₂ |
| 39 | 3,4-DiClPh | O | para | H | H | 1 | CH₂CONH₂ |
| 11 | 3,4-DiClPh | O | para | H | H | 0 | CH₂CO-1-(4-acetyl)-piperazinyl |
| 22 | 3,4-DiClPh | O | para | H | H | 1 | CH₂CO-1-(4-acetyl)-piperazinyl |
| 27 | 3,4-DiClPh | O | para | H | H | 2 | CH₂CO-1-(4-acetyl)-piperazinyl |
| 30 | 3,4-DiClPh | O | para | H | H | 1 | CH₂COOH |
| 15 | 3,4-DiClPh | O | ortho | H | H | 0 | CH₂CONH₂ |
| 20 | 3,4-DiClPh | O | ortho | H | H | 1 | CH₂CONH₂ |
|  | 3,4-DiClPh | O | ortho | H | H | 0 | CH₂CO-1-(4-acetyl)-piperazinyl |
| 40 | 3,4-DiClPh | O | ortho | H | H | 1 | CH₂CO-1-(4-acetyl)-piperazinyl |
|  | 3,4-DiClPh | O | para | H | H | 0 | CH₂CO-1-(4-carboxamide)-piperazinyl |
| 41 | 3,4-DiClPh | O | para | H | H | 1 | CH₂CO-1-(4-carboxamide)-piperazinyl |
|  | 4-OCH₃Ph | O | ortho | H | H | 0 | CH₂CONH₂ |
| 42 | 4-OCH₃Ph | O | ortho | H | H | 1 | CH₂CONH₂ |
|  | 2-ClPh | O | para | H | H | 0 | CH₂CONH₂ |
| 43 | 2-ClPh | O | para | H | H | 1 | CH₂CONH₂ |
|  | 4-OHPh | O | ortho | H | H | 0 | CH₂CONH₂ |
| 44 | 4-OHPh | O | ortho | H | H | 1 | CH₂CONH₂ |
|  | 2-ClPh | O | ortho | H | H | 0 | CH₂CONH₂ |
| 45 | 2-ClPh | O | ortho | H | H | 1 | CH₂CONH₂ |
|  | 2-ClPh | O | para | H | H | 0 | CH₂CO-1-(4-acetyl)-piperazinyl |
| 46 | 2-ClPh | O | para | H | H | 1 | CH₂CO-1-(4-acetyl)-piperazinyl |
|  | 2-ClPh | O | para | H | H | 0 | CH₂CO-N-piperazinyl |
| 47 | 2-ClPh | O | para | H | H | 1 | CH₂CO-N-piperazinyl |
|  | 4-FPh | O | para | H | H | 0 | CH₂CO-1-(4-acetyl)-piperazinyl |
| 48 | 4-FPh | O | para | H | H | 1 | CH₂CO-1-(4-acetyl)-piperazinyl |

TABLE 1-continued

![Structure: Ar-X-(phenyl with R2, R3)-CH2-S(O)q-Y-R1]

| Ex. n° | Ar | X | Position* | R² | R³ | q | Y—R¹ |
|---|---|---|---|---|---|---|---|
| 95 | 4-FPh | O | para | H | H | 2 | CH₂CO-1-(4-acetyl)-piperazinyl |
| 96 | 4-FPh | O | para | H | H | 1 | CH₂COOH |
|  | 4-FPh | O | ortho | H | H | 0 | CH₂CO-1-(4-acetyl)-piperazinyl |
| 49 | 4-FPh | O | ortho | H | H | 1 | CH₂CO-1-(4-acetyl)-piperazinyl |
|  | 4-FPh | O | para | H | H | 0 | CH₂CONH₂ |
| 50 | 4-FPh | O | para | H | H | 1 | CH₂CONH₂ |
|  | 4-FPh | O | ortho | H | H | 0 | CH₂CONH₂ |
| 51 | 4-FPh | O | ortho | H | H | 1 | CH₂CONH₂ |
|  | 2-Naphthyl | O | ortho | H | H | 0 | CH₂CONH₂ |
| 52 | 2-Naphthyl | O | ortho | H | H | 1 | CH₂CONH₂ |
|  | 2-Naphthyl | O | ortho | H | H | 0 | CH₂CO-1-(4-acetyl)-piperazinyl |
| 53 | 2-Naphthyl | O | ortho | H | H | 1 | CH₂CO-1-(4-acetyl)-piperazinyl |
|  | 2-Naphthyl | O | para | H | H | 0 | CH₂CONH₂ |
| 54 | 2-Naphthyl | O | para | H | H | 1 | CH₂CONH₂ |
|  | 2-BiPh | O | para | H | H | 0 | CH₂CONH₂ |
| 55 | 2-BiPh | O | para | H | H | 1 | CH₂CONH₂ |
|  | 2-BiPh | O | ortho | H | H | 0 | CH₂CONH₂ |
| 56 | 2-BiPh | O | ortho | H | H | 1 | CH₂CONH₂ |
|  | 2-ClPh | O | ortho | H | H | 0 | CH₂CO-1-(4-acetyl)-piperazinyl |
| 57 | 2-ClPh | O | ortho | H | H | 1 | CH₂CO-1-(4-acetyl)-piperazinyl |
|  | 2-Naphthyl | O | para | H | H | 0 | CH₂CO-1-(4-acetyl)-piperazinyl |
| 58 | 2-Naphthyl | O | para | H | H | 1 | CH₂CO-1-(4-acetyl)-piperazinyl |
|  | 2-BiPh | O | ortho | H | H | 0 | CH₂CO-1-(4-acetyl)-piperazinyl |
| 59 | 2-BiPh | O | ortho | H | H | 1 | CH₂CO-1-(4-acetyl)-piperazinyl |
|  | 2-BiPh | O | para | H | H | 0 | CH₂CO-1-(4-acetyl)-piperazinyl |
| 60 | 2-BiPh | O | para | H | H | 1 | CH₂CO-1-(4-acetyl)-piperazinyl |
|  | 4-ClPh | O | para | H | H | 0 | CH₂CO-1-(4-acetyl)-piperazinyl |
| 61 | 4-ClPh | O | para | H | H | 1 | CH₂CO-1-(4-acetyl)-piperazinyl |
|  | 4-OCH₃Ph | O | para | H | H | 0 | CH₂CO-1-(4-methyl)-piperazinyl |
| 62 | 4-OCH₃Ph | O | para | H | H | 1 | CH₂CO-1-(4-methyl)-piperazinyl |
|  | 3,4-DiClPh | O | para | H | H | 0 | CH₂CO-1-(4-ethylcarboxylate)-piperazinyl |
| 63 | 3,4-DiClPh | O | para | H | H | 1 | CH₂CO-1-(4-ethylcarboxylate)-HHpiperazinyl |
|  | 4-FPh | O | para | H | H | 0 | CH₂CO-1-(4-hydroxyethyl)-piperazinyl |
| 64 | 4-FPh | O | para | H | H | 1 | CH₂CO-1-(4-hydroxyethyl)-piperazinyl |
|  | 3,4-DiClPh | O | ortho | H | H | 0 | CH₂CO-1-(4-hydroxyethyl)-piperazinyl |
| 65 | 3,4-DiClPh | O | ortho | H | H | 1 | CH₂CO-1-(4-hydroxyethyl)-piperazinyl |
|  | 4-FPh | O | para | H | H | 0 | CH₂CO-1-(4-methyl)-piperazinyl |

TABLE 1-continued

[Structure: Ar−X−(phenyl with R2, R3)−CH2−S(O)q−Y−R1]

| Ex. n° | Ar | X | Position* | R² | R³ | q | Y—R¹ |
|---|---|---|---|---|---|---|---|
| 66 | 4-FPh | O | para | H | H | 1 | CH₂CO-1-(4-methyl)-piperazinyl |
|  | 4-ClPh | O | para | H | H | 0 | CH₂CONH₂ |
| 67 | 4-ClPh | O | para | H | H | 1 | CH₂CONH₂ |
|  | 4-FPh | O | para | H | H | 0 | CH₂CO-1-(4-ethylcarboxylate)-piperazinyl |
| 68 | 4-FPh | O | para | H | H | 1 | CH₂CO-1-(4-ethylcarboxylate)-piperazinyl |
|  | 4-OCH₃Ph | O | para | H | H | 0 | CH₂CO-1-(4-ethylcarboxylate)-piperazinyl |
| 69 | 4-OCH₃Ph | O | para | H | H | 1 | CH₂CO-1-(4-ethylcarboxylate)-piperazinyl |
|  | 4-ClPh | S | para | H | H | 0 | CH₂CO-1-(4-ethylcarboxylate)-piperazinyl |
| 70 | 4-ClPh | S | para | H | H | 1 | CH₂CO-1-(4-ethylcarboxylate)-piperazinyl |
| 71 | 4-ClPh | SO | para | H | H | 1 | CH₂CO-1-(4-ethylcarboxylate)-piperazinyl |
|  | 3,4-DiClPh | O | ortho | H | H | 0 | CH₂CO-1-(4-ethylcarboxylate)-piperazinyl |
| 72 | 3,4-DiClPh | O | ortho | H | H | 1 | CH₂CO-1-(4-ethylcarboxylate)-piperazinyl |
|  | Ph | O | ortho | H | H | 0 | CH₂CONH₂ |
| 97 | Ph | O | ortho | H | H | 1 | CH₂CONH₂ |
|  | Ph | O | ortho | H | H | 0 | CH₂CO-N-pyrrolidinyl |
| 98 | Ph | O | ortho | H | H | 1 | CH₂CO-N-pyrrolidinyl |
|  | Ph | O | ortho | H | H | 0 | CH₂CONMe₂ |
| 99 | Ph | O | ortho | H | H | 1 | CH₂CONMe₂ |
|  | Ph | O | para | H | H | 0 | CH₂CONMe₂ |
| 100 | Ph | O | para | H | H | 1 | CH₂CONMe₂ |
|  | Ph | O | para | H | H | 0 | CH₂CO-N-pyrrolidinyl |
| 101 | Ph | O | para | H | H | 1 | CH₂CO-N-pyrrolidinyl |
|  | Ph | O | para | H | H | 0 | CH₂CONH₂ |
| 102 | Ph | O | para | H | H | 1 | CH₂CONH₂ |
|  | Ph | O | ortho | H | H | 0 | CH₂CONHCH₂CN |
| 103 | Ph | O | ortho | H | H | 1 | CH₂CONHCH₂CN |
|  | Ph | O | ortho | H | H | 0 | CH₂CONHCHMe₂ |
| 104 | Ph | O | ortho | H | H | 1 | CH₂CONHCHMe₂ |
|  | Ph | O | ortho | H | H | 0 | CH₂CONHCMe₃ |
| 105 | Ph | O | ortho | H | H | 1 | CH₂CONHCMe₃ |
|  | Ph | O | ortho | H | H | 0 | CH₂CO-1-(4-hydroxy)-piperidinyl |
| 106 | Ph | O | ortho | H | H | 1 | CH₂CO-1-(4-hydroxy)-piperidinyl |
| 12 | Ph | O | ortho | H | H | 0 | CH₂CONH(CH₂)₂OH |
| 21 | Ph | O | ortho | H | H | 1 | CH₂CONH(CH₂)₂OH |
|  | Ph | O | ortho | H | H | 0 | CH₂CO-1-(4-acetyl)-piperazinyl |
| 107 | Ph | O | ortho | H | H | 1 | CH₂CO-1-(4-acetyl)-piperazinyl |
|  | Ph | O | meta | H | H | 0 | CH₂CONH(CH₂)₂OH |
| 108 | Ph | O | meta | H | H | 1 | CH₂CONH(CH₂)₂OH |
|  | Ph | O | meta | H | H | 0 | CH₂CO-1-(4-hydroxy)-piperidinyl |
| 109 | Ph | O | meta | H | H | 1 | CH₂CO-1-(4-hydroxy)-piperidinyl |

TABLE 1-continued

| Ex. n° | Ar | X | Position* | R² | R³ | q | Y—R¹ |
|---|---|---|---|---|---|---|---|
| 110 | Ph | O | para | H | H | 1 | CH₂CO-1-(4-acetyl)-piperazinyl |
| 111 | Ph | O | para | H | H | 1 | CH₂CONH(CH₂)₂OH |
| 112 | Ph | O | para | H | H | 1 | CH₂CO-1-(4-hydroxy)-piperidinyl |
| 113 | 4-ClPh | CONH | ortho | H | H | 1 | CH₂CONH₂ |
| 114 | 3,4-DiOCH₃Ph | CONH | ortho | H | H | 1 | CH₂CONH₂ |
| 115 | 2-Naphthyl | CONH | ortho | H | H | 1 | CH₂CONH₂ |
| 116 | 4-ClPh | CONH | ortho | H | H | 1 | CH₂CO-1-(4-acetyl)-piperazinyl |
| 117 | 3,4DiFPh | CONH | ortho | H | H | 1 | CH₂CONH₂ |
| 118 | 2,4-DiOCH₃Ph | CONH | ortho | H | H | 1 | CH₂CONH₂ |
| 119 | 3,4,5-TriOCH₃Ph | CONH | ortho | H | H | 1 | CH₂CONH₂ |
| 120 | 3,4-DiOCH₃Ph | CONH | meta | H | H | 1 | CH₂CONH₂ |
| 121 | 2,4-DiOCH₃Ph | CONH | ortho | H | H | 1 | CH₂CO-1-(4-acetyl)-piperazinyl |
| 122 | 3,4-DiOCH₃Ph | CONH | ortho | H | H | 1 | CH₂CO-1-(4-acetyl)-piperazinyl |
| 123 | 4-FPh | CONH | ortho | H | H | 1 | CH₂CO-1-(4-acetyl)-piperazinyl |
| 124 | 3,4-DiClPh | CONH | ortho | H | H | 1 | CH₂CO-1-(4-acetyl)-piperazinyl |
| 125 | 2,4-DiOCH₃Ph | CONH | meta | H | H | 1 | CH₂CONH₂ |
| 126 | 4-FPh | CONH | meta | H | H | 1 | CH₂CONH₂ |
| 127 | 3,4-DiClPh | CONH | meta | H | H | 1 | CH₂CONH₂ |
| 7 | 4-ClPh | O | para | H | H | 0 | CH₃ |
| 8 | 4-ClPh | O | para | H | H | 1 | CH₃ |
| 9 | 4-ClPh | O | para | H | H | 1 | CH₂[4(4-ClPhenoxy)phenyl] |
|  | 3,4-DiClPh | O | para | H | H | 0 | CH₃ |
| 10 | 3,4-DiClPh | O | para | H | H | 1 | CH₃ |
|  | 4-ClPh | S | ortho | H | H | 0 | CH₂CO-N-piperazinyl |
| 73 | 4-ClPh | S | ortho | H | H | 1 | CH₂CO-N-piperazinyl |
|  | 2,3-DiClPh | O | ortho | H | H | 0 | CH₂CO-1-(4-acetyl)-piperazinyl |
| 74 | 2,3-DiClPh | O | ortho | H | H | 1 | CH₂CO-1-(4-acetyl)-piperazinyl |
|  | 2,5-DiClPh | O | ortho | H | H | 0 | CH₂CO-1-(4-acetyl)-piperazinyl |
| 75 | 2,5-DiClPh | O | ortho | H | H | 1 | CH₂CO-1-(4-acetyl)-piperazinyl |
|  | 2,5-DiClPh | O | ortho | H | H | 0 | CH₂CONH₂ |
| 76 | 2,5-DiClPh | O | ortho | H | H | 1 | CH₂CONH₂ |
|  | 2,3-DiClPh | O | ortho | H | H | 0 | CH₂CONH₂ |
| 77 | 2,3-DiClPh | O | ortho | H | H | 1 | CH₂CONH₂ |
|  | 2,4-DiClPh | O | para | H | H | 0 | CH₂CO-1-(4-acetyl)-piperazinyl |
| 78 | 2,4-DiClPh | O | para | H | H | 1 | CH₂CO-1-(4-acetyl)-piperazinyl |
|  | 2,4-DiClPh | O | ortho | H | H | 0 | CH₂CO-1-(4-acetyl)-piperazinyl |
| 79 | 2,4-DiClPh | O | ortho | H | H | 1 | CH₂CO-1-(4-acetyl)-piperazinyl |
|  | 2,4-DiClPh | O | para | H | H | 0 | CH₂CONH₂ |
| 80 | 2,4-DiClPh | O | para | H | H | 1 | CH₂CONH₂ |
|  | 2,4-DiClPh | O | ortho | H | H | 0 | CH₂CONH₂ |
| 81 | 2,4-DiClPh | O | ortho | H | H | 1 | CH₂CONH₂ |
|  | 3,5-DiClPh | O | ortho | H | H | 0 | CH₂CO-1-(4-acetyl)-piperazinyl |
| 82 | 3,5-DiClPh | O | ortho | H | H | 1 | CH₂CO-1-(4-acetyl)-piperazinyl |
|  | 3,5-DiClPh | O | para | H | H | 0 | CH₂CO-1-(4-acetyl)-piperazinyl |
| 83 | 3,5-DiClPh | O | para | H | H | 1 | CH₂CO-1-(4-acetyl)-piperazinyl |
|  | 3,5-DiClPh | O | para | H | H | 0 | CH₂CONH₂ |
| 84 | 3,5-DiClPh | O | para | H | H | 1 | CH₂CONH₂ |
|  | 3,5-DiClPh | O | ortho | H | H | 0 | CH₂CONH₂ |

TABLE 1-continued

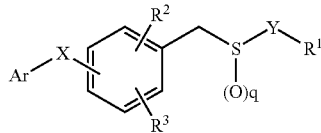

| Ex. n° | Ar | X | Position* | R² | R³ | q | Y—R¹ |
|---|---|---|---|---|---|---|---|
| 85 | 3,5-DiClPh | O | ortho | H | H | 1 | CH₂CONH₂ |
|  | 2,5-DiClPh | O | para | H | H | 0 | CH₂CO-1-(4-acetyl)-piperazinyl |
| 86 | 2,5-DiClPh | O | para | H | H | 1 | CH₂CO-1-(4-acetyl)-piperazinyl |
|  | 3,4-DiClPh | S | para | H | H | 0 | CH₂CO-1-(4-acetyl)-piperazinyl |
| 87 | 3,4-DiClPh | S | para | H | H | 1 | CH₂CO-1-(4-acetyl)-piperazinyl |
|  | 2,5-DiClPh | S | para | H | H | 0 | CH₂CONH₂ |
| 88 | 2,5-DiClPh | S | para | H | H | 1 | CH₂CONH₂ |
|  | 3,4-DiClPh | S | para | H | H | 0 | CH₂CONH₂ |
| 89 | 3,4-DiClPh | S | para | H | H | 1 | CH₂CONH₂ |
|  | 2,3-DiClPh | O | para | H | H | 0 | CH₂CO-1-(4-acetyl)-piperazinyl |
| 90 | 2,3-DiClPh | O | para | H | H | 1 | CH₂CO-1-(4-acetyl)-piperazinyl |
|  | 2,6-DiClPh | O | para | H | H | 0 | CH₂CO-1-(4-acetyl)-piperazinyl |
| 91 | 2,6-DiClPh | O | para | H | H | 1 | CH₂CO-1-(4-acetyl)-piperazinyl |
|  | 2,6-DiClPh | O | para | H | H | 0 | CH₂CONH₂ |
| 92 | 2,6-DiClPh | O | para | H | H | 1 | CH₂CONH₂ |
|  | 2,3-DiClPh | O | para | H | H | 0 | CH₂CONH₂ |
| 93 | 2,3-DiClPh | O | para | H | H | 1 | CH₂CONH₂ |
| 94 | 2,3-DiClPh | O | para | H | H | 2 | CH₂CONH₂ |
| 135 | Ph | NH | ortho | H | H | 1 | CH₂CO-1-(4-acetyl)-piperazinyl |
| 136 | Ph | NH | para | H | H | 1 | CH₂CO-1-(4-acetyl)-piperazinyl |
| 134 | 4-OCH₃Ph | NH | ortho | H | H | 1 | CH₂CO-1-(4-acetyl)-piperazinyl |
| 131 | 4-FPh | SO₂NH | para | H | H | 1 | CH₂CO-1-(4-acetyl)-piperazinyl |
| 137 | 4-OCH₃Ph | NH | para | H | H | 1 | CH₂CO-1-(4-acetyl)-piperazinyl |
| 138 | 4-FPh | NH | para | H | H | 1 | CH₂CO-1-(4-acetyl)-piperazinyl |
| 139 | 4-ClPh | NH | para | H | H | 1 | CH₂CO-1-(4-acetyl)-piperazinyl |
| 140 | 4-FPh | NH | para | H | H | 1 | CH₂CO-1-(4-acetyl)-piperazinyl |
| 128 | 3,4-DiClPh | CONH | para | H | H | 1 | CH₂CO-1-(4-acetyl)-piperazinyl |
| 129 | 4-FPh | CONH | para | H | H | 1 | CH₂CO-1-(4-acetyl)-piperazinyl |
| 141 | 3,4-DiClPh | NH | para | H | H | 1 | CH₂CO-1-(4-acetyl)-piperazinyl |
| 132 | 4-ClPh | SO₂NH | para | H | H | 1 | CH₂CO-1-(4-acetyl)-piperazinyl |
| 147 | 4-FPh | CH₂NH | para | H | H | 1 | CH₂CO-1-(4-acetyl)-piperazinyl |
| 133 | 3,4-DiClPh | SO₂NH | para | H | H | 1 | CH₂CO-1-(4-acetyl)-piperazinyl |
| 148 | 3,4-DiClPh | CH₂NH | para | H | H | 1 | CH₂CO-1-(4-acetyl)-piperazinyl |
| 149 | 4-FPh | CH₂NH | ortho | H | H | 1 | CH₂CO-1-(4-acetyl)-piperazinyl |
| 146 | 3,4-DiClPh | CH₂NH | ortho | H | H | 1 | CH₂CO-1-(4-acetyl)-piperazinyl |
| 130 | 3,4-DiClPh | SO₂NH | ortho | H | H | 1 | CH₂CO-1-(4-acetyl)-piperazinyl |
| 145 | 2-Furyl | CH₂NH | ortho | H | H | 1 | CH₂CO-1-(4-acetyl)-piperazinyl |
| 144 | 2-Thienyl | CH₂NH | ortho | H | H | 1 | CH₂CO-1-(4-acetyl)-piperazinyl |
| 142 | 2-Thienyl | CONH | ortho | H | H | 1 | CH₂CO-1-(4-acetyl)-piperazinyl |

TABLE 1-continued

| Ex. n° | Ar | X | Position* | $R^2$ | $R^3$ | q | Y—$R^1$ |
|---|---|---|---|---|---|---|---|
| 143 | 2-Furyl | CONH | ortho | H | H | 1 | $CH_2CO$-1-(4-acetyl)-piperazinyl |
| 152 | Ph | $OCH_2$ | ortho | H | H | 0 | $CH_2CONH_2$ |
| 153 | Ph | $OCH_2$ | ortho | H | H | 1 | $CH_2CONH_2$ |
| 17 | 4-ClPh | O | para | 2'-Cl | H | 0 | $CH_2CO$-1-(4-acetyl)-piperazinyl |
| 18 | 4-ClPh | O | para | 2'-Cl | H | 0 | $CH_2CONH_2$ |
| 25 | 4-ClPh | O | para | 2'-Cl | H | 1 | $CH_2CO$-1-(4-acetyl)-piperazinyl |
| 26 | 4-ClPh | O | para | 2'-Cl | H | 1 | $CH_2CONH_2$ |
| 149a | 3,4-DiClPh | CONH | para | H | H | 1 | $CH_2CONH_2$ |
| 109a | 4-ClPh | O | ortho | H | H | 1 | $CH_2CONH_2$ |
| 109b | 3-Cl-4-FPh | O | ortho | H | H | 1 | $CH_2CONH_2$ |
| 109c | 4-Cl-3-FPh | O | ortho | H | H | 1 | $CH_2CONH_2$ |
| 109d | 3-Cl-4-FPh | O | ortho | H | H | 2 | $CH_2CONH_2$ |
| 10a | 4-ClPh | O | ortho | 4'-Cl | H | 0 | $CH_2COOH$ |
| 18a | 4-ClPh | O | ortho | 4'-Cl | H | 0 | $CH_2CONH_2$ |
| 27a | 4-ClPh | O | ortho | 4'-Cl | H | 1 | $CH_2CONH_2$ |
| 27b | 4-ClPh | O | ortho | 4'-Cl | H | 2 | $CH_2CONH_2$ |
| 109e | 3,4-DiFPh | O | ortho | 4'-Cl | H | 1 | $CH_2CONH_2$ |
| 109f | 3,4-DiClPh | O | ortho | H | H | 2 | $CH_2CONH_2$ |
| 30a | 3,4-DiClPh | O | ortho | H | H | 1 | $CH_2COOH$ |
| 30d | 3,4-DiClPh | O | ortho | H | H | 0 | $CH_2COOMenthyl$ (1R,2S,5R) |
| 30e | 3,4-DiClPh | O | ortho | H | H | 1 | $CH_2COOH$ (−) |
| 30f | 3,4-DiClPh | O | ortho | H | H | 1 | $CH_2COOH$ (+) |
| 20a | 3,4-DiClPh | O | ortho | H | H | 1 | $CH_2CONH_2$ (−) |
| 20b | 3,4-DiClPh | O | ortho | H | H | 1 | $CH_2CONH_2$ (+) |
| 30b | 3,4-DiClPh | O | ortho | H | H | 2 | $CH_2COOH$ |
| 112a | 3,4-DiClPh | O | ortho | H | H | 1 | $CH_2CONHCH_3$ |
| 112b | 3,4-DiClPh | O | ortho | H | H | 1 | $CH_2CON(C_2H_5)_2$ |
| 30f | 3,4-DiClPh | O | ortho | H | H | 0 | $CH_2CON(CH_3)_2$ |
| 30g | 3,4-DiClPh | O | ortho | H | H | 1 | $CH_2CON(CH_3)_2$ |

Ph = phenyl, ClPh = chlorophenyl, DiClPh = di-chlorophenyl, FPh = Fluoprophenyl.
*Position: the position refers to the position of the ArX lateral side chain as compared to —$CH_2$—$S(O)_q$—Y—$R^1$ group on the central benzyl ring.

Ortho is position 2', meta is position 3' and para is position 4'.

36. A use of a compound of formula (A)

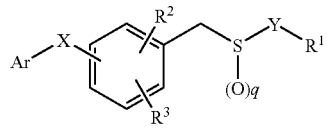

(A)

wherein:

Ar is independantly selected from $C_6$-$C_{10}$ aryl and 5 to 10-membered heteroaryl wherein:

$C_6$-$C_{10}$ aryl and heteroaryl are optionally substituted with one to three groups selected from F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)$ $R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

X is O, $S(O)_y$, $N(R^{10})$, $OC(R^{22})_2$, $(R^{22})_2C$—O, $C(R^{22})_2$ $NR^{21}$, $NR^{21}C(R^{22})_2$, $C(=O)N(R^{21})$, $NR^{21}C(=O)$, $S(O)_2$—$NR^{22}$, $NR^{22}S(O)_2$, $C(R^{22})_2C(R^{22})_2$, $CR^{22}=CR^{21}$, $C\equiv C$;

Y is $C_1$-$C_6$ alkylene; or
($C_1$-$C_4$ alkylene)$_m$—Z—($C_1$-$C_4$ alkylene)$_n$;
wherein said alkylene groups are optionally substituted with one to three $R^{20}$ groups;

Z is O, $NR^{10A}$, $S(O)_y$, $CR^{21}=CR^{21}$, $C\equiv C$, $C_6$-$C_{10}$ arylene, 5-10 membered heteroarylene, $C_3$-$C_6$ cycloalkylene, or 3-6 membered heterocyclo-alkylene; wherein said arylene, heteroarylene, cycloalkylene, and heterocycloalkylene groups are optionally substituted with one to three $R^{20}$ groups;

$R^1$ is selected from $C_6$-$C_{10}$ aryl, $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;
wherein said aryl groups are optionally substituted with one to three $R^{20}$ groups;

$R^2$ and $R^3$ are each independently selected from frem H, F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

$R^{10}$ and $R^{10A}$ are each independently selected from H, $C_1$-$C_6$ alkyl, $C_6$-$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_1$-$C_6$ alkyl, and $C_6$-$C_{10}$ aryl; wherein said alkyl and aryl groups are optionally substituted with one to three $R^{20}$ groups;

$R^{12}$ and $R^{13}$ at each occurrence are each independently selected from H, $C_1$-$C_6$ alkyl, and $C_6$-$C_{10}$ aryl, or $R^{12}$ and $R^{13}$, together with the nitrogen to which they are attached, form a 3-7 membered heterocyclic ring; wherein said alkyl and aryl groups and heterocyclic ring are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;

$R^{20}$ at each occurrence is independently selected from F, Cl, Br, I, $OR^{22}$, $OR^{25}$, $NR^{23}R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from H, $C_1$-$C_6$ alkyl, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring;

$R^{25}$ at each occurrence is independently the residue of an amino acid after the hydroxyl group of the carboxyl group is removed;

m is 0 or 1;
n is 0 or 1;
q is 0, 1, or 2;
y is 0, 1, or 2;

and the stereoisomeric forms, mixtures of stereoisomeric forms or pharmaceutically acceptable salts forms thereof, for the manufacture of a medicament useful for treating a disease or a disorder selected from the group consisting of sleepiness associated with narcolepsy, obstructive sleep apnea or shift work disorder; Parkinson's disease; Alzheimer's disease; attention deficit disorder; attention deficit hyperactivity disorder; depression; and fatigue.

37. The use according to embodiment 36 for the manufacture of a medicament useful for the treatment of sleepiness associated with narcolepsy.

38. A use of a compound of formula (A)

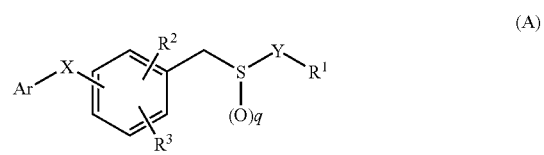

(A)

wherein:
Ar is independantly selected from $C_6$-$C_{10}$ aryl and 5 to 10-membered heteroaryl wherein:
$C_6$-$C_{10}$ aryl and heteroaryl are optionally substituted with one to three groups selected from F, Cl, Br, I, $R^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

X is O, $S(O)_y$, $N(R^{10})$, $OC(R^{22})_2$, $(R^{22})_2C-O$, $C(R^{22})_2NR^{21}$, $NR^{21}C(R^{22})_2$, $C(=O)N(R^{21})$, $NR^{21}C(=O)$, $S(O)_2-NR^{22}$, $NR^{22}S(O)_2$, $C(R^{22})_2$, $C(R^{22})_2$, $CR^{21}=CR^{21}$, $C\equiv C$;

Y is $C_1$-$C_6$ alkylene; or
$(C_1$-$C_4$ alkylene$)_m$—Z—$(C_1$-$C_4$ alkylene$)_n$;
wherein said alkylene groups are optionally substituted with one to three $R^{20}$ groups;

Z is O, $NR^{10A}$, $S(O)_y$, $CR^{21}=CR^{21}$, $C\equiv C$, $C_6$-$C_{10}$ arylene, 5-10 membered heteroarylene, $C_3$-$C_6$ cycloalkylene, or 3-6 membered heterocyclo-alkylene; wherein said arylene, heteroarylene, cycloalkylene, and heterocycloalkylene groups are optionally substituted with one to three $R^{20}$ groups;

$R^1$ is selected from $C_6$-$C_{10}$ aryl, $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;
wherein said aryl groups are optionally substituted with one to three $R^{20}$ groups;

$R^2$ and $R^3$ are each independently selected from frem H, F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ membered heterocycloalkyl, phenyl, 5 or 6 membered heteroaryl, arylalkyl, $C(=O)R^{22}$, $R^{10}$ and $R^{10A}$ are each independently selected from H, $C_1$-$C_6$ alkyl, $C_6$-$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_1$-$C_6$ alkyl, and $C_6$-$C_{10}$ aryl; wherein said alkyl and aryl groups are optionally substituted with one to three $R^{20}$ groups;

$R^{12}$ and $R^{13}$ at each occurrence are each independently selected from H, $C_1$-$C_6$ alkyl, and $C_6$-$C_{10}$ aryl, or $R^{12}$ and $R^{13}$, together with the nitrogen to which they are attached, form a 3-7 membered heterocyclic ring; wherein said alkyl and aryl groups and heterocyclic ring are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;

$R^{20}$ at each occurrence is independently selected from F, Cl, Br, I, $OR^{22}$, $OR^{25}$, $NR^3R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$, $R^{21}$ at each occurrence is independently selected from H and $C_1$-$C_6$ alkyl;

$R^{22}$ at each occurrence is independently selected from H, $C_1$-$C_6$ alkyl, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring;

$R^{25}$ at each occurrence is independently the residue of an amino acid after the hydroxyl group of the carboxyl group is removed;

m is 0 or 1;

n is 0 or 1;

q is 0, 1, or 2;

y is 0, 1, or 2;

and the stereoisomeric forms, mixtures of stereoisomeric forms or pharmaceutically acceptable salts forms thereof, for the manufacture of a medicament useful for the treatment of a sleep-affecting disease or disorder in order to promote wakefulness.

39. A use of a compound of formula (A)

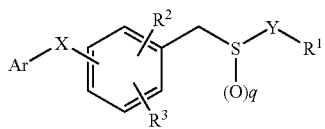

(A)

wherein:

Ar is independantly selected from $C_6$-$C_{10}$ aryl and 5 to 10-membered heteroaryl wherein:

$C_6$-$C_{10}$ aryl and heteroaryl are optionally substituted with one to three groups selected from F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

X is O, $S(O)_y$, $N(R^{10})$, $OC(R^{22})_2$, $(R^{22})_2C$—O, $C(R^{22})_2NR^{21}$, $NR^{21}C(R^{22})_2$, $C(=O)N(R^{21})$, $NR^{21}C(=O)$, $S(O)_2$—$NR^{22}$, $NR^{22}S(O)_2$, $C(R^{22})_2C(R^{22})_2$, $CR^{21}=CR^{21}$, $C\equiv C$;

Y is $C_1$-$C_6$ alkylene; or $(C_1$-$C_4$ alkylene$)_m$—Z—$(C_1$-$C_4$ alkylene$)_n$;

wherein said alkylene groups are optionally substituted with one to three $R^{20}$ groups;

Z is O, $NR^{10A}$, $S(O)_y$, $CR^{21}=CR^{21}$, $C\equiv C$, $C_6$-$C_{10}$ arylene, 5-10 membered heteroarylene, $C_3$-$C_6$ cycloalkylene, or 3-6 membered heterocyclo-alkylene; wherein said arylene, heteroarylene, cycloalkylene, and heterocycloalkylene groups are optionally substituted with one to three $R^{20}$ groups;

$R^1$ is selected from $C_6$-$C_{10}$ aryl, $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;

wherein said aryl groups are optionally substituted with one to three $R^{20}$ groups;

$R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

$R^{10}$ and $R^{10A}$ are each independently selected from H, $C_1$-$C_6$ alkyl, $C_6$-$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently selected from H, $C_1$-$C_6$ alkyl, and $C_6$-$C_{10}$ aryl; wherein said alkyl and aryl groups are optionally substituted with one to three $R^{20}$ groups;

$R^{12}$ and $R^{13}$ at each occurrence are each independently selected from H, $C_1$-$C_6$ alkyl, and $C_6$-$C_{10}$ aryl, or $R^{12}$ and $R^{13}$, together with the nitrogen to which they are attached, form a 3-7 membered heterocyclic ring;

wherein said alkyl and aryl groups and heterocyclic ring are optionally substituted with one to three $R^{20}$ groups;

$R^{14}$ at each occurrence is independently selected from $C_1$-$C_6$ alkyl, $C_6$-$C_{10}$ aryl, and arylalkyl;

wherein said alkyl, aryl and arylalkyl groups are optionally substituted with one to three $R^{20}$ groups;

$R^{20}$ at each occurrence is independently selected from F, Cl, Br, I, $OR^{22}$, $OR^{25}$, $NR^{23}R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from H, $C_1$-$C_6$ alkyl, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring;

$R^{25}$ at each occurrence is independently the residue of an amino acid after the hydroxyl group of the carboxyl group is removed;

m is 0 or 1;

n is 0 or 1;

q is 0, 1, or 2;

y is 0, 1, or 2;

and the stereoisomeric forms, mixtures of stereoisomeric forms or pharmaceutically acceptable salts forms thereof, for the manufacture of a medicament useful for treating a neurological disease or disorder selected from Parkinson's disease; Alzheimer disease; attention deficit disorder; attention deficit hyperactivity disorder; depression; and fatigue associated with a neurological disease or disorder.

40. A pharmaceutical composition comprising a compound of formula (A)

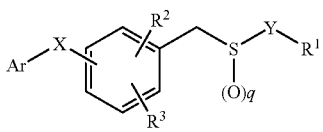

(A)

wherein:
Ar is independantly selected from $C_6$-$C_{10}$ aryl and 5 to 10-membered heteroaryl wherein:
  $C_6$-$C_{10}$ aryl and heteroaryl are optionally substituted with one to three groups selected from F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
X is O, $S(O)_y$, $N(R^{10})$, $OC(R^{22})_2$, $(R^{22})_2C-O$, $C(R^{22})_2NR^{21}$, $NR^{21}C(R^{22})_2$, $C(=O)N(R^{21})$, $NR^{21}C(=O)$, $S(O)_2-NR^{22}$, $NR^{22}S(O)_2$, $C(R^{22})_2C(R^{22})_2$, $CR^{21}=CR^{21}$, $C\equiv C$;
Y is $C_1$-$C_6$ alkylene; or
$(C_1$-$C_4$ alkylene$)_m$—Z—$(C_1$-$C_4$ alkylene$)_n$;
  wherein said alkylene groups are optionally substituted with one to three $R^{20}$ groups;
Z is O, $NR^{10A}$, $S(O)_y$, $CR^{21}=CR^{21}$, $C\equiv C$, $C_6$-$C_{10}$ arylene, 5-10 membered heteroarylene, $C_3$-$C_6$ cycloalkylene, or 3-6 membered heterocyclo-alkylene; wherein said arylene, heteroarylene, cycloalkylene, and heterocycloalkylene groups are optionally substituted with one to three $R^{20}$ groups;
$R^1$ is selected from $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;
  wherein said aryl groups are optionally substituted with one to three $R^{20}$ groups;
$R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
$R^{10}$ and $R^{10A}$ are each independently selected from H, $C_1$-$C_6$ alkyl, $C_6$-$C_{10}$ aryl, $C(=O)R^{14}$, and $S(O)_xR^{14}$; wherein said alkyl and aryl groups are optionally substituted with one to three $R^{20}$ groups;
$R^{11}$ at each occurrence is independently selected from H, $C_1$-$C_6$ alkyl, and $C_6$-$C_{10}$ aryl;
  wherein said alkyl and aryl groups are optionally substituted with one to three $R^{20}$ groups;
$R^{12}$ and $R^{13}$ at each occurrence are each independently selected from H, $C_1$-$C_6$ alkyl, or $R^{12}$ and $R^{13}$, together with the nitrogen to which they are attached, form a 3-7 membered heterocyclic ring;
  wherein said alkyl group and heterocyclic ring are optionally substituted with one to three $R^{20}$ groups;
$R^{14}$ at each occurrence is independently selected from $C_1$-$C_6$ alkyl, $C_6$-$C_{10}$ aryl, and arylalkyl;
  wherein said alkyl, aryl and arylalkyl groups are optionally substituted with one to three R groups;

$R^{20}$ at each occurrence is independently selected from F, Cl, Br, I, $OR^{22}$, $OR^{25}$, $NR^{23}R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
$R^{21}$ at each occurrence is independently selected from H and $C_1C_6$ alkyl;
$R^{22}$ at each occurrence is independently selected from H $C_1$-$C_6$ alkyl, and $C_6$-$C_{10}$ aryl;
$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocyclic ring;
$R^{25}$ at each occurrence is independently the residue of an amino acid after the hydroxyl group of the carboxyl group is removed;
m is 0 or 1;
n is 0 or 1;
q is 0, 1, or 2;
y is 0, 1, or 2;

and the stereoisomeric forms, mixtures of stereoisomeric forms or pharmaceutically acceptable salts forms thereof,
in admixture with one or more pharmaceutically acceptable excipients.

41. A method for preparing a compound of embodiments 1 to 35, comprising the steps of:
  i) reacting a thiouronium compound (E) with a reactant of structure $LG$-$YR^1$ to form a compound of formula (I):

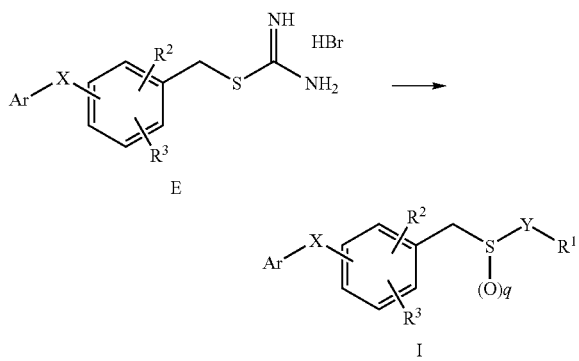

wherein Ar, X, $R^2$, $R^3$, Y, $R^1$ are as defined in embodiment 1, q=0 and LG represents a leaving group; and optionally
  ii) isolating the formed compound of formula (I).

42. The method of embodiment 41, wherein step i) comprises:
  a) converting the compound of formula (E) into the corresponding thiol compound; and
  b) reacting the obtained thiol compound with the reactant LG-Y—$R^1$.

43. The method of embodiments 41 or 42, wherein the compound (E) is formed by reacting the compound (D) with thiourea and a suitable acid HA:

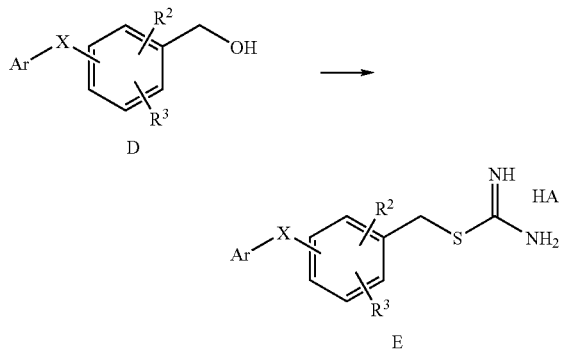

wherein Ar, X, $R^2$, $R^3$ are as defined in embodiment 1.

44. The method of embodiment 43, wherein the compound (D) is formed by reacting a compound (C) with a suitable reducing agent:

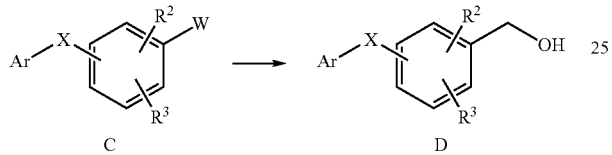

wherein Ar, X, $R^2$, $R^3$ are as defined in embodiment 1 and W is C(=O)H or COOH.

45. The method according to embodiment 44, wherein compound (C) is formed by reacting a compound (A) with a compound (B):

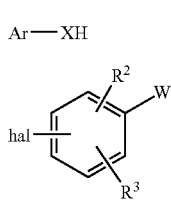

46. The method according to any of embodiments 41 to 45, wherein the compound formed at step i) is a compound of formula (I) wherein q is 0, $R^1$ is COOR, and R represents H or $(C_1-C_6)$ alkyl:

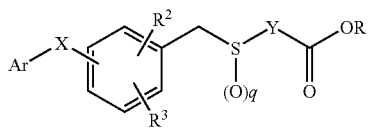

47. The method according to embodiment 46 further comprising:
 a1) reacting the carboxylic acid or ester of formula (I) with an appropriate amine of general structure $NHR^{12}R^{13}$, wherein $R^{12}$ and $R^{13}$ are as defined in embodiment 1; and optionally
 b1) isolating the obtained compound of formula (I) wherein $R^1$ is $C(=O)NR^{12}R^{13}$.

48. The method of any of embodiments 46 or 47 further comprising:
 a2) oxidizing the compound of formula (I) wherein q is 0; and optionally
 b2) isolating the obtained compound of formula (I) wherein q is 1 or 2.

Although the present invention has been described in considerable detail, those skilled in the art will appreciate that numerous changes and modifications may be made to the embodiments and preferred embodiments of the invention and that such changes and modifications may be made without departing from the spirit of the invention. It is therefore intended that the appended embodiments cover all equivalent variations as fall within the scope of the invention.

What is claimed is:
1. A compound of formula (A):

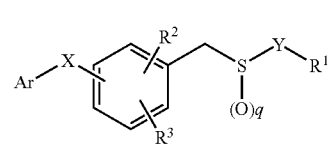

(A)

wherein:
 Ar is $C_6-C_{10}$ aryl wherein:
  $C_6-C_{10}$aryl is optionally substituted with one to three groups selected from F, Cl, Br, I, $OR^{22}$, $OR^{25}$, $NR^{23}R^{24}$, NHOH, $NO_2$, CN, $CF_3$, $C_1-C_6$ alkyl, $C_2-C_6$ alkenyl, $C_2-C_6$ alkynyl, $C_3-C_7$ cycloalkyl, phenyl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
 X is O, $S(O)_y$, $N(R^{10})$, $OC(R^{22})_2$, $(R^{22})_2CO$, $C(R^{22})_2NR^{21}$, $NR^{21}C(R^{22})_2$, $C(=O)N(R^{21})$, $NR^{21}C(=O)$, $S(O)_2-NR^{22}$, $NR^{22}S(O)_2$, $C(R^{22}C(R^{22})_2$, $CR^{21}=CR^{21}$, C≡C;
 Y is $C_1-C_6$ alkylene; or $(C_1-C_4$ alkylene$)_m$-$Z$-$(C_1-C_4$ alkylene$)_n$; wherein said alkylene groups are optionally substituted with one to three $R^{20}$ groups;
 Z is O, $NR^{10A}$, $S(O)_y$, $CR^{21}=CR^{21}$, C≡C, $C_6-C_{10}$ arylene, or $C_3-C_6$ cycloalkylene, wherein said arylene, and cycloalkylene groups are optionally substituted with one to three $R^{20}$ groups;
 $R^1$ is selected from $NR^{12}R^{13}$, $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$; wherein said aryl groups are optionally substituted with one to three $R^{20}$ groups;
 $R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1-C_6$ alkyl, $C_2-C_6$ alkenyl, $C_2-C_6$ alkynyl, $C_3-C_7$ cycloalkyl, phenyl, arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
 $R^{10}$ and $R^{10A}$ are each independently selected from H, $C_1-C_6$ alkyl, $C_6-C_{10}$ aryl, $C(=O)R^{14}$, and $S(O)_yR^{14}$; wherein said alkyl and aryl groups are optionally substituted with one to three groups;
 $R^{11}$ at each occurrence is independently selected from H, $C_3-C_7$ alkyl and $C_6-C_{10}$ aryl; wherein said alkyl and aryl group are optionally substituted with one to three $R^{20}$ groups;

$R^{12}$ and $R^{13}$ at each occurrence are each independently selected from H, $C_1$-$C_6$ alkyl;
  wherein said alkyl group is optionally substituted with one to three $R^{20}$ groups;
$R^{14}$ at each occurrence is independently selected from $C_1$-$C_6$ alkyl, $C_6$-$C_{10}$ aryl, and arylalkyl;
  wherein said alkyl, aryl and arylalkyl groups are optionally substituted with one to three $R^{20}$ groups;
$R^{20}$ at each occurrence is independently selected from F, Cl, Br, I, $OR^{22}$, $OR^{25}$, $NR^{23}R^{24}$, NHOH, $NO_2$, CN, $CF_3$, $C_1$-$C_6$ alkyl optionally substituted by one to three OH, $C_2$-$C_6$ alkenyl, $C_2$-$C_6$ alkynyl, $C_3$-$C_7$ cycloalkyl, phenyl, 5 membered arylalkyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
$R^{21}$ at each occurrence is independently selected from H and $C_1$-$C_6$ alkyl;
$R^{22}$ at each occurrence is independently selected from H, $C_1$-$C_6$ alkyl, and $C_6$-$C_{10}$ aryl;
$R^{23}$ and $R^{24}$ at each occurrence are each independently selected from H, $C_1$-$C_6$ alkyl, and $C_6$-$C_{10}$ aryl;
$R^{25}$ at each occurrence is independently the residue of an amino acid after the hydroxyl group of the carboxyl group is removed;
m is 0 or 1;
n is 0 or 1;
q is 1 or 2;
y is 0, 1, or 2;
Ar—X is positioned ortho or para to —$CH_2$—$S(O)_n$—Y—$R^1$;
with the exclusion of the compounds wherein:
  Y is $C_2$ alkylene substituted with one to three $C_1$-$C_6$ alkylene and/or $NR^{23}R^{24}$
  and/or $NR^{21}CO_2R^{22}$; and
  $R^1$ is $C(=O)NR^{12}R^{13}$
and the stereoisomeric forms, mixtures of stereoisomeric forms or pharmaceutically acceptable salts forms thereof.

2. The compound according to claim 1, wherein:
Y is $C_1$-$C_6$ alkylene;
($C_1$-$C_4$ alkylene)$_m$-$Z^1$-($C_1$-$C_4$ alkylene)$_n$;
$C_1$-$C_4$ alkylene-$Z^2$-$C_1$-$C_4$ alkylene;
wherein said alkylene groups are optionally substituted with one to three $R^{20}$ groups;
$Z^1$ is $CR^{21}=CR^{21}$, $C≡C$, $C_6$-$C_{10}$ arylene, or $C_3$-$C_6$ cycloalkylene; wherein said arylene, and cycloalkylene groups are optionally substituted with one to three $R^{22}$ groups;
$Z^2$ is O, $NR^{10A}$, or $S(O)_y$.

3. The compound according to claim 1 wherein q is 1.

4. The compound according to claim 1 wherein $R_1$ is selected from $NR^{12}R^{13}$, $NR^{21}C(=O)R^{14}$, $C(O=)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$; and $NR^{21}S(O)_2NR^{12}R^{13}$.

5. The compound according to claim 1 wherein $R^1$ is selected from $NR^{12}R^{13}$; $NR^{21}C(=O)R^{14}$; $C(=O)NR^{12}R^{13}$; $C(=NR^{11})NR^{12}R^{13}$; and $NR^{21}C(=O)NR^{12}R^{13}$.

6. The compound according to claim 5 wherein $R^1$ is $C(=O)NR^{12}R^{13}$.

7. The compound according to claim 6 wherein $R^{12}$ and $R^{13}$ are each independently selected from H and $C_1$-$C_6$ alkyl.

8. The compound according to claim 4 wherein $R^1$ is selected from $C(=O)R^{14}$, $CO_2R^{11}$, $OC(=O)R^{11}$, $C(=O)NR^{12}R^{13}$, $OC(=O)NR^{12}R^{13}$, $NR^{21}S(O)_2R^{11}$, and $NR^{21}S(O)_2NR^{12}R^{13}$.

9. The compound according to claim 1 wherein X is O, $S(O)_y$, $N(R^{10})$.

10. The compound according to claim 1 wherein X is $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2NR^{22}$, $NR^{22}S(O)_2$, $C(R^{22})_2C(R^{22})_2$.

11. The compound according to claim 10 wherein X is $OC(r^{22})_2$, $C(R^{22})_2NR^{21}$, $C(=O)N(R^{21})$, $S(O)_2$—$NR^{22}$.

12. The compound according to claim 1 wherein Y is $C_1$-$C_6$ alkylene.

13. The compound according to claim 12 wherein Y is $CH_2$.

14. The compound according to claim 2 wherein Y is ($C_1$-$C_4$ alkylene)$_m$-$Z^1$-($C_1$-$C_4$ alkylene)$_n$.

15. The compound according to claim 14 wherein $Z^1$ is $C_6$-$C_{10}$ arylene or $C_3$-$C_6$ cycloalkylene.

16. The compound according to claim 15 wherein $Z^1$ is phenylene.

17. The compound according to claim 14 wherein $Z^1$ is $CR^{21}=CR^{21}$ or $C≡C$.

18. The compound according to claim 2 wherein Y is $C_1$-$C_4$ alkylene-$Z^2$-$C_1$-$C_4$alkylene.

19. The compound according to claim 18 wherein $Z^2$ is O.

20. The compound according to claim 1 with the structure:

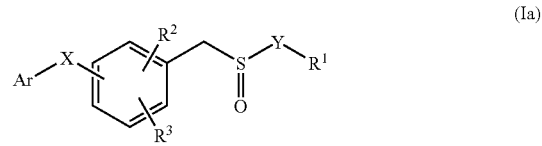

(Ia)

wherein:
Ar is optionally substituted with one to three groups selected from F, Cl, Br, I, $OR^{22}$, $OR^{25}$, $NR^{23}R^{24}$, NHOH, $NO_2$, CN, $C_1$-$C_6$ alkyl, phenyl, arylalkyl, and $C(=O)R^{22}$;
X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(O)$, $S(O)_2NR^{22}$, $NR^{22}S(O)_2$;
Y is $C_1$-$C_6$ alkylene;
  $C_1$-$C_4$ alkylene-$Z^1$—($C_1$-$C_4$ alkylene)$_m$, or
  $C_1$-$C_4$ alkylene-$Z^2$—$C_1$-$C_4$ alkylene;
  wherein said alkylene groups are optionally substituted with one to three $R^{20}$ groups;
$Z^1$ is $CR^{21}=CR^{21}$, $C≡C$, $C_6$-$C_{10}$ arylene, or $C_3$-$C_6$ cycloalkylene
$Z^2$ is O, $NR^{10A}$, or $S(O)_y$;
$R^1$ is selected from $NR^{21}C(=O)R^{14}$, $C(=O)R^{14}$, $CO_2R^{11}$, $OC(=O)R^{11}$, $C(=O)NR^{12}R^{13}$, $C(=NR^{11})NR^{12}R^{13}$, $OC(=O)NR^{12}R^{13}$, $NR^{21}S(O)_2R^{11}$, $NR^{21}C(=O)NR^{12}R^{13}$, and $NR^{21}S(O)_2NR^{12}R^{13}$;
$R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, phenyl, arylalkyl, $C(=O)R^{22}$;
$R^{10}$ and $R^{10A}$ are each independently selected from H, $C_1$-$C_6$ alkyl, $C(=O)R^{14}$, and $S(O)_yR^{14}$; wherein said alkyl groups are optionally substituted with one to three $R^{20}$ groups;
$R^{11}$ at each occurrence is independently selected from H or $C_3$-$C_7$ alkyl, wherein said alkyl group is optionally substituted with one to three $R^{20}$ groups;

$R^{12}$ and $R^{13}$ at each occurrence are each independently selected from H, and $C_1$-$C_6$ alkyl; wherein said alkyl group is are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;

$R^{20}$ at each occurrence is independently selected from F, Cl, Br, I, $OR^{22}$, $OR^{25}$, $NR^{22}R^{24}$, NHOH, $NO_2$, CN, $CF_3$, phenyl, benzyl, $C(=O)R^{22}$, $CO_2R^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;

$R^{21}$ at each occurrence is independently selected from H and $C_1$-$C_6$ alkyl; and $R^{22}$ at each occurrence is independently selected from H, $C_1$-$C_6$ alkyl, and $C_6$-$C_{10}$ aryl;

$R^{23}$ and $R^{24}$ at each occurrence are each independently selected from H, and $C_1$-$C_6$ alkyl;

$R^{25}$ at each occurrence is independently the residue of an amino acid after the hydroxyl group of the carboxyl group is removed;

n is 0 or 1;

y is 0, 1, or 2;

and the stereoisomeric forms, mixtures of stereoisomeric forms or pharmaceutically acceptable salts forms thereof.

21. The compound according to claim 20 wherein: Y is $C_1$-$C_6$ alkylene, $C_1$-$C_4$ alkylene-$Z^1$—$C_1$-$C_4$ alkylene, or $C_1$-$C_4$ alkylene-$Z^2$—$C_1$-$C_4$ alkylene, wherein said alkylene groups are optionally substituted with one to three $C_1$-$C_6$ alkyl groups;

$Z^1$ is $CR^{21}=CR^{21}$, $C\equiv C$, or phenyl;

$Z^2$ is O, $NR^{10A}$, or $S(O)_y$;

X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2NR^{22}$, $NR^{22}S(O)_2$; and $R^1$ is selected from $NR^{21}C(=O)R^{14}$, $C(=O)R^{14}$, $CO_2R^{11}$, $OC(=O)R^{11}$, and $C(=)NR^{12}R^{13}$.

22. The compound according to claim 21 wherein $R^1$ is $C(=O)NR^{12}R^{13}$.

23. The compound according to claim 22 having the structure of formula (Ib):

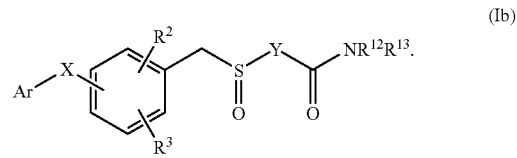

(Ib)

24. The compound according to claim 23 wherein X is O, $S(O)_y$, $N(R^{10})$, $OC(R^{22})_2$, $C(R^{22})_2O$, $C(R^{22})_2NR^{21}$, $NR^{21}C(R^{22})_2$, $C(=O)N(R^{21})$, $NR^{21}C(=O)$, $S(O)_2$—$NR^{22}$, $NR^{22}S(O)_2$.

25. The compound according to claim 24 wherein X is O, $S(O)_y$, NH.

26. The compound according to claim 24 wherein X is $OCH_2$, $CH_2O$, $CH_2NH$, $NHCH_2$, $C(=O)NH$, $NHC(=O)$, $S(O)_2NH$, $NHS(O)_2$.

27. The compound according to claim 24 wherein X is NH, O—$CH_2$, $CH_2NH$, $C(=O)NH$, or $S(O)_2$—NH.

28. The compound according to any of claims 1, 20, or 23 wherein $R^2$ and $R^3$ are each independently selected from H, F, Cl, Br, I, $OR^{22}$, $OR^{25}$, $NR^{23}R^{24}$, NHOH, $NO_2$, CN, $CF_3$, $C_1$-$C_6$ alkyl, phenyl, arylalkyl, $C(=O)R^{22}$.

29. The compound according to claim 23 wherein Y is $C_1$-$C_6$ alkylene.

30. The compound according to claim 29 wherein Y is $CH_2$.

31. The compound according to claim 23 wherein Y is $(C_1$-$C_4$ alkylene)$_n$-$Z^1$—$C_1$-$C_4$ alkylene and $Z^1$ is phenyl, $CR^{21}=CR^{21}$, or $C\equiv C$.

32. A compound selected in accordance with the following table, wherein:

TABLE 1

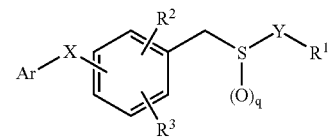

| Ex. No. | Ar | X | Position* | $R^2$ | $R^3$ | q | Y—$R^1$ |
|---|---|---|---|---|---|---|---|
| 29 | Ph | O | para | H | H | 1 | $CH_2CONHCHMe_2$ |
|  | Ph | O | meta | H | H | 0 | $CH_2CONH_2$ |
| 32 | Ph | O | meta | H | H | 1 | $CH_2CONH_2$ |
|  | Ph | O | meta | H | H | 0 | $CH_2CONMe_2$ |
| 33 | Ph | O | meta | H | H | 1 | $CH_2CONMe_2$ |
|  | Ph | O | meta | H | H | 0 | $CH_2CONHCHMe_2$ |
| 34 | Ph | O | meta | H | H | 1 | $CH_2CONHCHMe_2$ |
|  | 4-$OCH_3$Ph | O | para | H | H | 0 | $CH_2CONH_2$ |
| 36 | 4-$OCH_3$Ph | O | para | H | H | 1 | $CH_2CONH_2$ |
|  | 3,4-DiClPh | O | para | H | H | 0 | $CH_2CONH_2$ |
| 39 | 3,4-DiClPh | O | para | H | H | 1 | $CH_2CONH_2$ |
| 30 | 3,4-DiClPh | O | para | H | H | 1 | $CH_2COOH$ |
| 15 | 3,4-DiClPh | O | ortho | H | H | 0 | $CH_2CONH_2$ |
| 20 | 3,4-DiClPh | O | ortho | H | H | 1 | $CH_2CONH_2$ |
|  | 4-$OCH_3$Ph | O | ortho | H | H | 0 | $CH_2CONH_2$ |
| 42 | 4-$OCH_3$Ph | O | ortho | H | H | 1 | $CH_2CONH_2$ |
|  | 2-ClPh | O | para | H | H | 0 | $CH_2CONH_2$ |
| 43 | 2-ClPh | O | para | H | H | 1 | $CH_2CONH_2$ |
|  | 4-OHPh | O | ortho | H | H | 0 | $CH_2CONH_2$ |

TABLE 1-continued

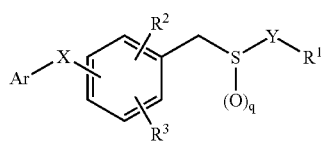

| Ex. No. | Ar | X | Position* | R² | R³ | q | Y—R¹ |
|---|---|---|---|---|---|---|---|
| 44 | 4-OHPh | O | ortho | H | H | 1 | CH₂CONH₂ |
|  | 2-ClPh | O | ortho | H | H | 0 | CH₂CONH₂ |
| 45 | 2-ClPh | O | ortho | H | H | 1 | CH₂CONH₂ |
| 96 | 4-FPh | O | para | H | H | 1 | CH₂COOH |
|  | 4-FPh | O | para | H | H | 0 | CH₂CONH₂ |
| 50 | 4-FPh | O | para | H | H | 1 | CH₂CONH₂ |
|  | 4-FPh | O | ortho | H | H | 0 | CH₂CONH₂ |
| 51 | 4-FPh | O | ortho | H | H | 1 | CH₂CONH₂ |
|  | 2-Naphthyl | O | ortho | H | H | 0 | CH₂CONH₂ |
| 52 | 2-Naphthyl | O | ortho | H | H | 1 | CH₂CONH₂ |
|  | 2-Naphthyl | O | para | H | H | 0 | CH₂CONH₂ |
| 54 | 2-Naphthyl | O | para | H | H | 1 | CH₂CONH₂ |
|  | 2-BiPh | O | para | H | H | 0 | CH₂CONH₂ |
| 55 | 2-BiPh | O | para | H | H | 1 | CH₂CONH₂ |
|  | 2-BiPh | O | ortho | H | H | 0 | CH₂CONH₂ |
| 56 | 2-BiPh | O | ortho | H | H | 1 | CH₂CONH₂ |
|  | 4-ClPh | O | para | H | H | 0 | CH₂CONH₂ |
| 67 | 4-ClPh | O | para | H | H | 1 | CH₂CONH₂ |
|  | Ph | O | ortho | H | H | 0 | CH₂CONH₂ |
| 97 | Ph | O | ortho | H | H | 1 | CH₂CONH₂ |
|  | Ph | O | ortho | H | H | 0 | CH₂CONMe₂ |
| 99 | Ph | O | ortho | H | H | 1 | CH₂CONMe₂ |
|  | Ph | O | para | H | H | 0 | CH₂CONMe₂ |
| 100 | Ph | O | para | H | H | 1 | CH₂CONMe₂ |
|  | Ph | O | para | H | H | 0 | CH₂CONH₂ |
| 102 | Ph | O | para | H | H | 1 | CH₂CONH₂ |
|  | Ph | O | ortho | H | H | 0 | CH₂CONHCH₂CN |
| 103 | Ph | O | ortho | H | H | 1 | CH₂CONHCH₂CN |
|  | Ph | O | ortho | H | H | 0 | CH₂CONHCHMe₂ |
| 104 | Ph | O | ortho | H | H | 1 | CH₂CONHCHMe₂ |
|  | Ph | O | ortho | H | H | 0 | CH₂CONHCMe₃ |
| 105 | Ph | O | ortho | H | H | 1 | CH₂CONHCMe₃ |
| 12 | Ph | O | ortho | H | H | 0 | CH₂CONH(CH₂)₂OH |
| 21 | Ph | O | ortho | H | H | 1 | CH₂CONH(CH₂)₂OH |
|  | Ph | O | meta | H | H | 0 | CH₂CONH(CH₂)₂OH |
| 108 | Ph | O | meta | H | H | 1 | CH₂CONH(CH₂)₂OH |
| 111 | Ph | O | para | H | H | 1 | CH₂CONH(CH₂)₂OH |
| 113 | 4-ClPh | CONH | ortho | H | H | 1 | CH₂CONH₂ |
| 114 | 3,4-DiOCH₃Ph | CONH | ortho | H | H | 1 | CH₂CONH₂ |
| 115 | 2-Naphthyl | CONH | ortho | H | H | 1 | CH₂CONH₂ |
| 117 | 3,4-DiFPh | CONH | ortho | H | H | 1 | CH₂CONH₂ |
| 118 | 2,4-DiOCH₃Ph | CONH | ortho | H | H | 1 | CH₂CONH₂ |
| 119 | 3,4,5-TriOCH₃Ph | CONH | ortho | H | H | 1 | CH₂CONH₂ |
| 120 | 3,4-DiOCH₃Ph | CONH | meta | H | H | 1 | CH₂CONH₂ |
| 125 | 2,4-DiOCH₃Ph | CONH | meta | H | H | 1 | CH₂CONH₂ |
| 126 | 4-FPh | CONH | meta | H | H | 1 | CH₂CONH₂ |
| 127 | 3,4-DiClPh | CONH | meta | H | H | 1 | CH₂CONH₂ |
|  | 2,5-DiClPh | O | ortho | H | H | 0 | CH₂CONH₂ |
| 76 | 2,5-DiClPh | O | ortho | H | H | 1 | CH₂CONH₂ |
|  | 2,3-DiClPh | O | ortho | H | H | 0 | CH₂CONH₂ |
| 77 | 2,3-DiClPh | O | ortho | H | H | 1 | CH₂CONH₂ |
|  | 2,4-DiClPh | O | para | H | H | 0 | CH₂CONH₂ |
| 80 | 2,4-DiClPh | O | para | H | H | 1 | CH₂CONH₂ |
|  | 2,4-DiClPh | O | ortho | H | H | 0 | CH₂CONH₂ |
| 81 | 2,4-DiClPh | O | ortho | H | H | 1 | CH₂CONH₂ |
|  | 3,5-DiClPh | O | para | H | H | 0 | CH₂CONH₂ |
| 84 | 3,5-DiClPh | O | para | H | H | 1 | CH₂CONH₂ |
|  | 3,5-DiClPh | O | ortho | H | H | 0 | CH₂CONH₂ |
| 85 | 3,5-DiClPh | O | ortho | H | H | 1 | CH₂CONH₂ |
|  | 2,5-DiClPh | S | para | H | H | 0 | CH₂CONH₂ |
| 88 | 2,5-DiClPh | S | para | H | H | 1 | CH₂CONH₂ |
|  | 3,4-DiClPh | S | para | H | H | 0 | CH₂CONH₂ |
| 89 | 3,4-DiClPh | S | para | H | H | 1 | CH₂CONH₂ |
|  | 2,6-DiClPh | O | para | H | H | 0 | CH₂CONH₂ |
| 92 | 2,6-DiClPh | O | para | H | H | 1 | CH₂CONH₂ |
|  | 2,3-DiClPh | O | para | H | H | 0 | CH₂CONH₂ |
| 93 | 2,3-DiClPh | O | para | H | H | 1 | CH₂CONH₂ |

TABLE 1-continued

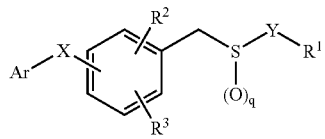

| Ex. No. | Ar | X | Position* | R² | R³ | q | Y—R¹ |
|---|---|---|---|---|---|---|---|
| 94 | 2,3-DiClPh | O | para | H | H | 2 | CH₂CONH₂ |
| 152 | Ph | OCH₂ | ortho | H | H | 0 | CH₂CONH₂ |
| 153 | Ph | OCH₂ | ortho | H | H | 1 | CH₂CONH₂ |
| 18 | 4-ClPh | O | para | 2'-Cl | H | 0 | CH₂CONH2 |
| 26 | 4-ClPh | O | para | 2'-Cl | H | 1 | CH₂CONH₂ |
| 149a | 3,4-DiClPh | CONH | para | H | H | 1 | CH₂CONH₂ |
| 109a | 4-ClPh | O | ortho | H | H | 1 | CH₂CONH₂ |
| 109b | 3-Cl-4-FPh | O | ortho | H | H | 1 | CH₂CONH₂ |
| 109c | 4-Cl-3-FPh | O | ortho | H | H | 1 | CH₂CONH₂ |
| 109d | 3-Cl-4-FPh | O | ortho | H | H | 2 | CH₂CONH₂ |
| 10a | 4-ClPh | O | ortho | 4'-Cl | H | 0 | CH₂COOH |
| 18a | 4-ClPh | O | ortho | 4'-Cl | H | 0 | CH₂CONH₂ |
| 27a | 4-ClPh | O | ortho | 4'-Cl | H | 1 | CH₂CONH₂ |
| 27b | 4-ClPh | O | ortho | 4'-Cl | H | 2 | CH₂CONH₂ |
| 109e | 3,4-DiFPh | O | ortho | 4'-Cl | H | 1 | CH₂CONH₂ |
| 109f | 3,4-DiClPh | O | ortho | H | H | 2 | CH₂CONH₂ |
| 30a | 3,4-DiClPh | O | ortho | H | H | 1 | CH₂COOH |
| 30d | 3,4-DiClPh | O | ortho | H | H | 0 | CH₂COOMenthyl (1R,2S,5R) |
| 30e | 3,4-DiClPh | O | ortho | H | H | 1 (−) | CH₂COOH |
| 30f | 3,4-DiClPh | O | ortho | H | H | 1 (+) | CH₂COOH |
| 20a | 3,4-DiClPh | O | ortho | H | H | 1 (−) | CH₂CONH₂ |
| 20b | 3,4-DiClPh | O | ortho | H | H | 1 (+) | CH₂CONH₂ |
| 30b | 3,4-DiClPh | O | ortho | H | H | 2 | CH₂COOH |
| 112a | 3,4-DiClPh | O | ortho | H | H | 1 | CH₂CONHCH3 |
| 112b | 3,4-DiClPh | O | ortho | H | H | 1 | CH₂CON(C₂H₅)₂ |
| 30f | 3,4-DiClPh | O | ortho | H | H | 0 | CH₂CON(CH₃)₂ |
| 30g | 3,4-DiClPh | O | ortho | H | H | 1 | CH₂CON(CH₃)₂ |

Ph = phenyl, ClPh = chlorophenyl, DiClPh = di-chlorophenyl, FPh = Fluorophenyl;
*Position: the position refers to the position of the ArX lateral side chain as compared to
—CH₂—S(O)$_q$—Y—R¹ group on the central benzyl ring;
Ortho is position 2', meta is position 3' and para is position 4' and the stereoisomeric forms, mixtures of stereoisomeric forms or pharmaceutically acceptable salts forms thereof.

33. A method of treating a disease or a disorder selected from the group consisting of sleepiness associated with narcolepsy; obstructive sleep apnea; shift work disorder, attention deficit disorder; attention deficit; hyperactivity disorder; depression; and fatigue, comprising administering to a patient in need thereof a compound of claim 1 or a stereoisomeric form, mixture of stereoisomeric forms, or a pharmaceutically acceptable salts form thereof.

34. The method according to claim 33 wherein the disease or disorder is sleepiness associated with narcolepsy.

35. A method for the treatment of a sleep-affecting disease, or disorder in order to promote wakefulness comprising administering to a patient in need thereof a compound according to claim 1 or a stereoisomeric form, mixture of stereoisomeric forms, or a pharmaceutically acceptable salt form thereof.

36. A pharmaceutical composition comprising a compound of claim 1 and the stereoisomeric forms, mixtures of stereoisomeric forms or pharmaceutically acceptable salts forms thereof, in admixture with one or more pharmaceutically acceptable excipients.

37. A method for preparing a compound of claim 1, comprising the steps of:
i.) reacting a thiouronium compound (E) with a reactant of structure LG-YR¹ to form a compound of formula (I):

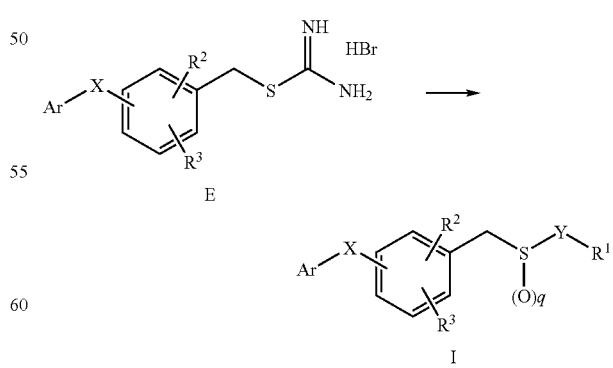

wherein Ar, X, R², R³, Y, R¹ are as defined in claim 1, q=0 and LG represents a leaving group; and optionally
ii) isolating the formed compound of formula (I).

38. The method of claim 37, wherein step i) comprises:

a) converting the compound of formula (E) into the corresponding thiol compound; and b) reacting the obtained thiol compound with the reactant LG-Y-R$^1$.

39. The method of claim 38, wherein the compound (E) is formed by reacting the compound (D) with thiourea and a suitable acid HA:

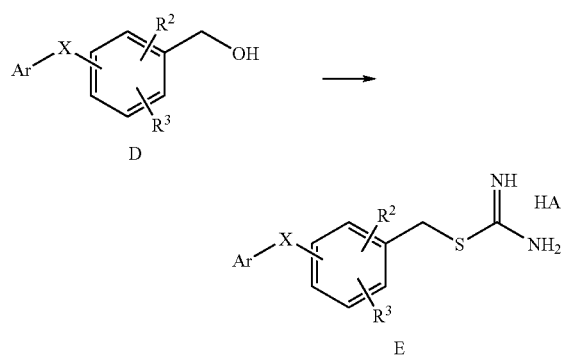

wherein Ar, X, R$^2$, R$^3$ are as defined in claim 1.

40. The method of claim 39, wherein the compound (D) is formed by reacting a compound (C) with a suitable reducing agent:

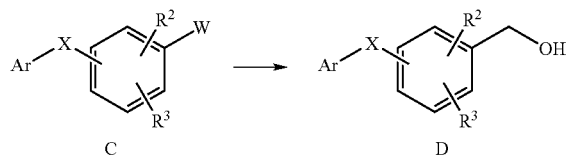

wherein Ar, X, R$^2$, R$^3$ are as defined in claim 1 and W is C(=O)H or COOH.

41. The method according to claim 40, wherein compound (C) is formed by reacting a compound (A) with a compound (B):

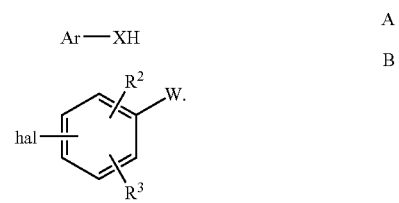

42. The method according to claim 41, wherein the compound formed at step i) is a compound of formula (I) wherein q is 0, R$^1$ is COOR, and R represents H or (C$_1$-C$_6$) alkyl

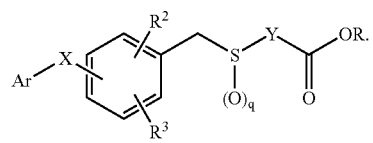

43. The method according to claim 42 further comprising:

a1) reacting the carboxylic acid or ester of formula (I) with an appropriate amine of general structure NHR$^{12}$R$^{13}$, wherein R$^{12}$ and R$^{13}$ are as defined in claim 1; and optionally b1) isolating the obtained compound of formula (I) wherein R$^1$ is C(=O)NR$^{12}$R$^{13}$.

44. The method of claim 42 or 43 further comprising:

a2) oxidizing the compound of formula (I) wherein q is 0; and optionally b2) isolating the obtained compound of formula (I) wherein q is 1 or 2.

45. A compound according to claim 1, wherein:

Ar is C$_6$-C$_{10}$ aryl wherein:

C$_6$-C$_{10}$ aryl is optionally substituted with one to three groups selected from Cl, Br, I, OR$^{22}$, OR$^{25}$, NR$^{23}$R$^{24}$, NHOH, NO$_2$, CN, CF$_3$, C$_1$-C$_6$ alkyl, C$_2$-C$_6$ alkenyl, C$_2$-C$_6$ alkynyl, C$_3$-C$_7$ cycloalkyl, phenyl, arylalkyl, C(=O)R$^{22}$, CO$_2$R$^{22}$, OC(=O)R$^{22}$, C(=O)NR$^{23}$R$^{24}$, NR$^{21}$C(=O)R$^{22}$, NR$^{21}$CO$_2$R$^{22}$, OC(=O)NR$^{23}$R$^{24}$, NR$^{21}$C(=S)R$^{22}$, and S(O)$_y$R$^{22}$.

46. The compound according to claim 32 selected in accordance with the following table, wherein:

TABLE 1

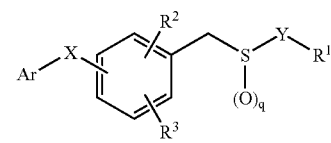

| Ex. No. | Ar | X | Position* | R$^2$ | R$^3$ | q | Y—R$^1$ |
|---|---|---|---|---|---|---|---|
| 29 | Ph | O | para | H | H | 1 | CH$_2$CONHCHMe$_2$ |
|  | Ph | O | meta | H | H | 0 | CH$_2$CONH$_2$ |
| 32 | Ph | O | meta | H | H | 1 | CH$_2$CONH$_2$ |
|  | Ph | O | meta | H | H | 0 | CH$_2$CONMe$_2$ |
| 33 | Ph | O | meta | H | H | 0 | CH$_2$CONMe$_2$ |
|  | Ph | O | meta | H | H | 0 | CH$_2$CONHCHMe$_2$ |
| 34 | Ph | O | meta | H | H | 1 | CH$_2$CONHCHMe$_2$ |
|  | 4-OCH$_3$Ph | O | para | H | H | 0 | CH$_2$CONH$_2$ |
| 36 | 4-OCH$_3$Ph | O | para | H | H | 1 | CH$_2$CONH$_2$ |
|  | 3,4-DiClPh | O | para | H | H | 0 | CH$_2$CONH$_2$ |
| 39 | 3,4-DiClPh | O | para | H | H | 1 | CH$_2$CONH$_2$ |

TABLE 1-continued

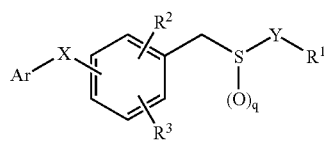

| Ex. No. | Ar | X | Position* | R² | R³ | q | Y—R¹ |
|---|---|---|---|---|---|---|---|
| 30 | 3,4-DiClPh | O | para | H | H | 1 | CH₂COOH |
| 15 | 3,4-DiClPh | O | ortho | H | H | 0 | CH₂CONH₂ |
| 20 | 3,4-DiClPh | O | ortho | H | H | 1 | CH₂CONH₂ |
|  | 4-OCH₃Ph | O | ortho | H | H | 0 | CH₂CONH₂ |
| 42 | 4-OCH₃Ph | O | ortho | H | H | 1 | CH₂CONH₂ |
|  | 2-ClPh | O | para | H | H | 0 | CH₂CONH₂ |
| 43 | 2-ClPh | O | para | H | H | 1 | CH₂CONH₂ |
|  | 4-OHPh | O | ortho | H | H | 0 | CH₂CONH₂ |
| 44 | 4-OHPh | O | ortho | H | H | 1 | CH₂CONH₂ |
|  | 2-ClPh | O | ortho | H | H | 0 | CH₂CONH₂ |
| 45 | 2-ClPh | O | ortho | H | H | 1 | CH₂CONH₂ |
|  | 2-Naphthyl | O | ortho | H | H | 0 | CH₂CONH₂ |
| 52 | 2-Naphthyl | O | ortho | H | H | 1 | CH₂CONH₂ |
|  | 2-Naphthyl | O | para | H | H | 0 | CH₂CONH₂ |
| 54 | 2-Naphthyl | O | para | H | H | 1 | CH₂CONH₂ |
|  | 2-BiPh | O | para | H | H | 0 | CH₂CONH₂ |
| 55 | 2-BiPh | O | para | H | H | 1 | CH₂CONH₂ |
|  | 2-BiPh | O | ortho | H | H | 0 | CH₂CONH₂ |
| 56 | 2-BiPh | O | ortho | H | H | 1 | CH₂CONH₂ |
|  | 4-ClPh | O | para | H | H | 0 | CH₂CONH₂ |
| 67 | 4-ClPh | O | para | H | H | 1 | CH₂CONH₂ |
|  | Ph | O | ortho | H | H | 0 | CH₂CONH₂ |
| 97 | Ph | O | ortho | H | H | 1 | CH₂CONH₂ |
|  | Ph | O | ortho | H | H | 0 | CH₂CONMe₂ |
| 99 | Ph | O | ortho | H | H | 1 | CH₂CONMe₂ |
|  | Ph | O | para | H | H | 0 | CH₂CONMe₂ |
| 100 | Ph | O | para | H | H | 1 | CH₂CONMe₂ |
|  | Ph | O | para | H | H | 0 | CH₂CONH₂ |
| 102 | Ph | O | para | H | H | 1 | CH₂CONH₂ |
|  | Ph | O | ortho | H | H | 0 | CH₂CONHCH₂CN |
| 103 | Ph | O | ortho | H | H | 1 | CH₂CONHCH₂CN |
|  | Ph | O | ortho | H | H | 0 | CH₂CONHCHMe₂ |
| 104 | Ph | O | ortho | H | H | 1 | CH₂CONHCHMe₂ |
|  | Ph | O | ortho | H | H | 0 | CH₂CONHCMe₃ |
| 105 | Ph | O | ortho | H | H | 1 | CH₂CONHCMe₃ |
| 12 | Ph | O | ortho | H | H | 0 | CH₂CONH(CH₂)₂OH |
| 21 | Ph | O | ortho | H | H | 1 | CH₂CONH(CH₂)₂OH |
|  | Ph | O | meta | H | H | 0 | CH₂CONH(CH₂)₂OH |
| 108 | Ph | O | meta | H | H | 1 | CH₂CONH(CH₂)₂OH |
| 111 | Ph | O | para | H | H | 1 | CH₂CONH(CH₂)₂OH |
| 113 | 4-ClPh | CONH | ortho | H | H | 1 | CH₂CONH₂ |
| 114 | 3,4-DiOCH₃Ph | CONH | ortho | H | H | 1 | CH₂CONH₂ |
| 115 | 2-Naphthyl | CONH | ortho | H | H | 1 | CH₂CONH₂ |
| 118 | 2,4-DiOCH₃Ph | CONH | ortho | H | H | 1 | CH₂CONH₂ |
| 119 | 3,4,5-TriOCH₃Ph | CONH | ortho | H | H | 1 | CH₂CONH₂ |
| 120 | 3,4-DiOCH₃Ph | CONH | meta | H | H | 1 | CH₂CONH₂ |
| 125 | 2,4-DiOCH₃Ph | CONH | meta | H | H | 1 | CH₂CONH₂ |
| 127 | 3,4-DiClPh | CONH | meta | H | H | 1 | CH₂CONH₂ |
|  | 2,5-DiClPh | O | ortho | H | H | 0 | CH₂CONH₂ |
| 76 | 2,5-DiClPh | O | ortho | H | H | 1 | CH₂CONH₂ |
|  | 2,3-DiClPh | O | ortho | H | H | 0 | CH₂CONH₂ |
| 77 | 2,3-DiClPh | O | ortho | H | H | 1 | CH₂CONH₂ |
|  | 2,4-DiClPh | O | para | H | H | 0 | CH₂CONH₂ |
| 80 | 2,4-DiClPh | O | para | H | H | 1 | CH₂CONH₂ |
|  | 2,4-DiClPh | O | ortho | H | H | 0 | CH₂CONH₂ |
| 81 | 2,4-DiClPh | O | ortho | H | H | 1 | CH₂CONH₂ |
|  | 3,5-DiClPh | O | para | H | H | 0 | CH₂CONH₂ |
| 84 | 3,5-DiClPh | O | para | H | H | 1 | CH₂CONH₂ |
|  | 3,5-DiClPh | O | ortho | H | H | 0 | CH₂CONH₂ |
| 85 | 3,5-DiClPh | O | ortho | H | H | 1 | CH₂CONH₂ |
|  | 2,5-DiClPh | S | para | H | H | 0 | CH₂CONH₂ |
| 88 | 2,5-DiClPh | S | para | H | H | 1 | CH₂CONH₂ |
|  | 3,4-DiClPh | S | para | H | H | 0 | CH₂CONH₂ |
| 89 | 3,4-DiClPh | S | para | H | H | 1 | CH₂CONH₂ |
|  | 2,6-DiClPh | O | para | H | H | 0 | CH₂CONH₂ |
| 92 | 2,6-DiClPh | O | para | H | H | 1 | CH₂CONH₂ |
|  | 2,3-DiClPh | O | para | H | H | 0 | CH₂CONH₂ |

TABLE 1-continued

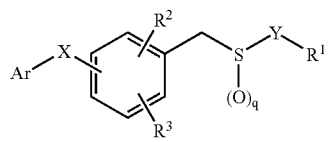

| Ex. No. | Ar | X | Position* | $R^2$ | $R^3$ | q | Y—$R^1$ |
|---|---|---|---|---|---|---|---|
| 93 | 2,3-DiClPh | O | para | H | H | 1 | $CH_2CONH_2$ |
| 94 | 2,3-DiClPh | O | para | H | H | 2 | $CH_2CONH_2$ |
| 152 | Ph | $OCH_2$ | ortho | H | H | 0 | $CH_2CONH_2$ |
| 153 | Ph | $OCH_2$ | ortho | H | H | 1 | $CH_2CONH_2$ |
| 18 | 4-ClPh | O | para | 2'-Cl | H | 0 | $CH_2CONH_2$ |
| 26 | 4-ClPh | O | para | 2'-Cl | H | 1 | $CH_2CONH_2$ |
| 149a | 3,4-DiClPh | CONH | para | H | H | 1 | $CH_2CONH_2$ |
| 109a | 4-ClPh | O | ortho | H | H | 1 | $CH_2CONH_2$ |
| 10a | 4-ClPh | O | ortho | 4'-Cl | H | 0 | $CH_2COOH$ |
| 18a | 4-ClPh | O | ortho | 4'-Cl | H | 0 | $CH_2CONH_2$ |
| 27a | 4-ClPh | O | ortho | 4'-Cl | H | 1 | $CH_2CONH_2$ |
| 27b | 4-ClPh | O | ortho | 4'-Cl | H | 2 | $CH_2CONH_2$ |
| 109f | 3,4-DiClPh | O | ortho | H | H | 2 | $CH_2CONH_2$ |
| 30a | 3,4-DiClPh | O | ortho | H | H | 1 | $CH_2COOH$ |
| 30d | 3,4-DiClPh | O | ortho | H | H | 0 | $CH_2COO$Menthyl (1R,2S,5R) |
| 30e | 3,4-DiClPh | O | ortho | H | H | 1 | $CH_2COOH$ (−) |
| 30f | 3,4-DiClPh | O | ortho | H | H | 1 | $CH_2COOH$ (+) |
| 20a | 3,4-DiClPh | O | ortho | H | H | 1 | $CH_2CONH_2$ (−) |
| 20b | 3,4-DiClPh | O | ortho | H | H | 1 | $CH_2CONH_2$ (+) |
| 30b | 3,4-DiClPh | O | ortho | H | H | 2 | $CH_2COOH$ |
| 112a | 3,4-DiClPh | O | ortho | H | H | 1 | $CH_2CONHCH_3$ |
| 112b | 3,4-DiClPh | O | ortho | H | H | 1 | $CH_2CON(C_2H_5)_2$ |
| 30f | 3,4-DiClPh | O | ortho | H | H | 0 | $CH_2CON(CH_3)_2$ |
| 30g | 3,4-DiClPh | O | ortho | H | H | 1 | $CH_2CON(CH_3)_2$ |

Ph = phenyl, ClPh = chlorophenyl, DiClPh = di-chlorophenyl;
*Position: the position refers to the position of the ArX lateral side chain as compared to —$CH_2$—$S(O)_q$—Y—$R^1$ group on the central benzyl ring;
Ortho is position 2', meta is position 3' and para is position 4';

and the stereoisomeric forms, mixtures of stereoisomeric forms or pharmaceutically acceptable salts forms thereof.

* * * * *